(12) United States Patent
Egbertson et al.

(10) Patent No.: US 7,279,487 B2
(45) Date of Patent: Oct. 9, 2007

(54) HYDROXYNAPHTHYRIDINONE CARBOXAMIDES USEFUL AS HIV INTEGRASE INHIBITORS

(75) Inventors: Melissa Egbertson, Ambler, PA (US); Jeffrey Y. Melamed, Warminster, PA (US); H. Marie Langford, Lansdale, NJ (US); Steven D. Young, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 342 days.

(21) Appl. No.: 10/500,972

(22) PCT Filed: Jan. 13, 2003

(86) PCT No.: PCT/US03/00813

§ 371 (c)(1),
(2), (4) Date: Jul. 2, 2004

(87) PCT Pub. No.: WO03/062204

PCT Pub. Date: Jul. 31, 2003

(65) Prior Publication Data

US 2005/0119482 A1 Jun. 2, 2005

Related U.S. Application Data

(60) Provisional application No. 60/349,775, filed on Jan. 17, 2002.

(51) Int. Cl.
*A61K 31/44* (2006.01)
*C07F 5/02* (2006.01)
*C07D 471/02* (2006.01)

(52) U.S. Cl. .................. 514/300; 546/13; 546/122; 546/123

(58) Field of Classification Search ............... 514/300; 546/113, 122, 123, 13
See application file for complete search history.

(56) References Cited

U.S. PATENT DOCUMENTS

| | | | | |
|---|---|---|---|---|
| 4,125,611 A | * | 11/1978 | Yamade et al. | ............. 514/201 |
| 4,226,863 A | * | 10/1980 | Yamada et al. | ............. 514/201 |
| 4,996,213 A | | 2/1991 | Mendes et al. | |
| 5,294,620 A | | 3/1994 | Ratcliffe et al. | |
| 5,413,999 A | | 5/1995 | Vacca et al. | |
| 5,519,021 A | | 5/1996 | Young et al. | |
| 5,801,183 A | | 9/1998 | Keana et al. | |
| 5,945,431 A | * | 8/1999 | Jin et al. | .................... 514/300 |

FOREIGN PATENT DOCUMENTS

| | | |
|---|---|---|
| EP | 1541558 A1 | 8/2003 |
| WO | WO95/00511 A1 | 1/1995 |
| WO | WO96/11198 A1 | 4/1996 |
| WO | WO96/11199 A1 | 4/1996 |
| WO | WO96/22990 A2 | 8/1996 |
| WO | WO98/11073 A | 3/1998 |
| WO | WO99/10347 A1 | 3/1999 |
| WO | WO 02/04443 A2 | 1/2002 |
| WO | WO 02/30930 A2 | 4/2002 |
| WO | WO 2004/024693 A | 3/2004 |

OTHER PUBLICATIONS

Ratner, L., et al., "Complete Nucleotide Sequence of the AIDS Virus, HTLV-III", Nature, vol. 313, pp. 277-284, (1985).
Toh, H., et al., "Close Structural Resemblance Between Putative Polymerase of a Drosphila Transposable Genetic Element 17.6 and Pol Gene Product of Moloney Murine Leukaemia Virus", EMBO Journal, vol. 4, pp. 1267-1272, (1985).
Power, M.D., et al., "Nucleotide Sequence of SRV-1, a Type D Simian Acquired Immune Deficiency Syndrome Retrovirus", Science, vol. 231, pp. 1567-1572, (1986).
Pearl, L.H., et al., "A Structural Model for the Retroviral Proteases", Nature, vol. 329, pp. 351-354, (1987).
Hart, E.P., J. "Naphthyridine. Part I. The Chemisry of 1:5-Naphthyridine", Journal of the Chemical Society, 1879-1882, (1954).

(Continued)

*Primary Examiner*—Rebecca Anderson
*Assistant Examiner*—Susannah Chung
(74) *Attorney, Agent, or Firm*—Kenneth R. Walton; Sheldon O. Heber

(57) ABSTRACT

Hydroxynaphthyridinone carboxamides of formula:

are described as inhibitors of HIV integrase and inhibitors of HIV replication, wherein L, $R^{1a}$, $R^{1b}$, $R^{1c}$, $R^{2a}$, $R^{2b}$, $R^3$, $R^4$, and $R^5$ are defined herein. These compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines. Methods of preventing, treating or delaying the onset of AIDS and methods of preventing or treating infection by HIV are also described.

19 Claims, No Drawings

OTHER PUBLICATIONS

Oakes, V., et al., "Polyazanaphthalenes. Part V. Some 2:4-Disubstituted 1:5 Naphthyridines", Journal of the Chemical Society, pp. 204-208, (1958).

McCaustland, D.J., et al., "1,5-Naphthyridines. Synthesis of 7-Chloro-4-(4-diethylamino-1-methybutylamino)-2-methoxy-1,5-naphthyridine and Related Compounds", vol. 7, pp. 467-463, (1970).

Buckle, D.R., et al., "4-Hydroxy-3-nitro-2 quinolones and Related Compounds as Inhibitors of Allergic Reactions", vol. 18, pp. 726-732, (1975).

Dunn, A.D., "The Sythesis of Novel Naphthrydines", Z. Chem., vol. 30, pp. 20-21, (1990).

Chen, J.L., et al., "Synthesis of Some Benzofuronaphthyridines and Benzofuronaphthyridine Derivatives", Journal of Heterocyclic Chemistry, vol. 30, pp. 909-912 (1993).

Zografos, A.L., et al., "Chemoselective Cyclization of Aminonicotinic Acid Derivatives to 1,8-Naphthyridin-2-ones via a Potential Intramolecular Azadiene-Ketene Electrocyclization Reaction", Journal of Organic Chemistry, vol. 66, pp. 4413-4415, (2001).

Bohn, B., et al., "Hammick Cyclizations Studies on the Mechanism of the Hammick Reaction", Heterocycles, vol. 37, Issue 3, pp. 1731-1746, (1994).

LaFemina, R. L., et al., "Requirement of Active Human Immunodeficiency Virus Type 1 Integrase Enzyme for Productive Infection of Human T-Lymphoid Cells", Journal of Virology, vol. 66, No. 12, pp. 7414-7419 (1992).

Hazuda, H. J., et al., "Inhibitors of Strand Transfer That Prevent Integration and Inhibit HIV-1 Replication Cells", Science, vol. 287, pp. 646-650 (2000).

Young, S. D., et al., "L-743,726 (DMP-266): A Novel, Highly Potent Nonnucleoside Inhibitor of the Human Immunodeficiency Virus Type 1 Reverse Transcriptase", Antimicrobial Agents and Chemotherapy, vol. 39, No. 12, pp. 2602-2605 (1995).

Vacca, J. P., et al., "L-735,524: An Orally Bioavailable Human Immunodeficiency Virus Type 1 Protease Inhibitor", Proc. Natl. Acad. Sci. USA, vol. 91, pp. 4096-4100 (1994).

Fauci, A. S., et al., "NIH Conference. Acquired Immunodeficiency Syndrome: Epidemiologic, Clinical, Immunologic, and Therapeutic Considerations", Annals of Internal Medicine, vol. 100, pp. 92-106 (1984).

The Medical Letter on Drugs and Therapeutics, "Diagnostic Tests for HIV", vol. 39, No. 1008, pp. 81-84 (1997).

Dean, M., et al., "Genetic Restriction of HIV-1 Infection and Progession to AIDS by a Deletion Allele of the CKR5 Structural Gene", Science, vol. 273, pp. 1856-1862 (1996).

Mylonakis, E., et al., "Laboratory Testing for Infection with the HumanImmunodeficiency Virus: Established and Novel Approaches", American Journal of Medicine, vol. 109, pp. 568-576 (2000).

Constantine, N. T., "Serologic Tests For The Retroviruses—Approaching A Decade Of Evolution", AIDS, vol. 7, pp. 1-13 (1993).

Mellors, J. W., et al., "Plasma Viral Load and CD4+ Lymphocytes as Prognostic Markers of HIV-1 Infection", Annals of Internal Medicine, vol. 126, No. 12, pp. 946-954 (1997).

* cited by examiner

HYDROXYNAPHTHYRIDINONE CARBOXAMIDES USEFUL AS HIV INTEGRASE INHIBITORS

This application is the National Stage of International Application No. PCT/U503/000813, filed on Jan. 13, 2003, which claims the benefit of U.S. Provisional Application No. 60/349,775, filed Jan. 17, 2002.

FIELD OF THE INVENTION

The present invention is directed to 4-hydroxy-2-oxo-1,2-dihydro-1,5-naphthyridine-3-carboxamides and pharmaceutically acceptable salts thereof, their synthesis, and their use as inhibitors of the HIV integrase enzyme. The compounds of the present invention and their pharmaceutically acceptable salts are useful for preventing or treating infection by HIV and for treating, delaying the onset of, or preventing AIDS.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3'termini of the linear proviral DNA; covalent joining of the recessed 3'OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, integrase and an HIV protease [Toh et al., *EMBO J.* 1985, 4: 1267; Power et al., *Science* 1986, 231: 1567; Pearl et al., *Nature* 1987, 329: 351]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhbitors such as indinavir and nelfinavir. The compounds of this invention are inhibitors of HIV integrase and inhibitors of HIV replication. The inhibition of integrase in vitro and of HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

Hart, *J. Chem. Soc.* 1954, 1879-1882 describes the amination, hydroxylation, oxidation and chlorination of 1,5-naphthyridine.

Oakes et al., *J. Chem. Soc.* 1958, 204-208 discloses the preparation of certain 2,4-disubstituted 1,5-naphthyridines including 2,4-dihydroxy-1,5-naphthyridine.

McCaustland et al., *J. Heterocyclic Chem.* 1970, 7: 467-473 discloses the preparation of 7-chloro-2,4-dihydroxy-1,5-naphthyridine.

Buckle et al., *J. Med. Chem.* 1975, 18: 726-732 discloses the preparation of 4-hydroxy-3-nitro-1,5-naphthyridin-2(1H)-one by direct nitration of the corresponding ketoamide.

Dunn, *Z. Chem.* 1990, 30: 20-21 discloses the preparation of 4-amino-3-ethoxycarbonyl-1,5-naphthyridin-2(1H)-one by heating diethyl malonate, sodium ethoxide, and 3-amino-2-cyanopyridine under reflux.

Chen et al., *J. Heterocyclic Chem.* 1993, 30: 909-912 discloses the preparation of 4-hydroxy-3-(o-methoxyphenyl)-1,5-naphthyridin-2(1H)-one by refluxing the ethyl ester of 3-(o-methoxybenzylcarbonylamino)pyridine-2-carboxylic acid with sodium ethoxide in benzene.

Zografos et al., *J. Org. Chem.* 2001, 66: 4413-4415 discloses the preparation of certain 4-hydroxy-1,8-naphthyridin-2-ones by reacting a pyrido[2,3-d][3,1]oxazin-4-one with the anion of a beta-ketoester formed by treatment with t-BuOK.

U.S. Pat. No. 4,996,213 discloses certain 4-amino-3-carboxy-1,5-naphthyridine derivatives. The derivatives are disclosed to have nervous system affecting properties.

U.S. Pat. No. 5,294,620 discloses certain 1,6-naphthyridin-2-one derivatives having angiotensin D antagonist activity.

WO 96/11198 and WO 96/11199 disclose certain 4-hydroxy-1,8-naphthyridin-2-one derivatives WO 95/00511 discloses certain 4-(phenyl- or pyridyl- or pyriridinyl-amino)-1,5-naphthyridine derivatives. The derivatives are disclosed to be anti-rheumatic agents.

WO 02/30930 (Publication of International Application No. PCT/US 01/31456, filed Oct. 9, 2001) discloses certain 8-hydroxy-1,6-naphthyridine-7-carboxamides which are HIV integrase inhibitors useful, inter alia, for treating HIV infection and AIDS.

SUMMARY OF THE INVENTION

The present invention is directed to novel hydroxynaphthyridinone carboxamides. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts, or as pharmaceutical composition ingredients, whether or not in combination with other HIV/AIDS antivirals, anti-infectives, immunomodulators, antibiotics or vaccines. More particularly, the present invention includes a compound of Formula (I):

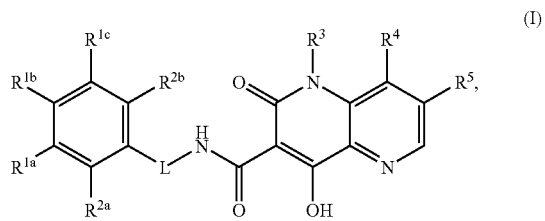

wherein L is a linker connecting the carbon atom of the phenyl ring to the nitrogen of the —NH— moiety, wherein L is (i) a single bond,
(ii) —(C$_{1-6}$ alkyl)-, which is optionally substituted with —C(=O)N(R$^a$R$^b$),
(iii) —(C$_{0-3}$ alkyl)-C=C—(C$_{1-3}$ alkyl)-,
(iv) —(C0$_{0-3}$ alkyl)-C≡C—(C$_{1-3}$ alkyl)-, or
(v) —(C$_{0-6}$ alkyl)-(C$_{3-6}$ cycloalkyl)-(C$_{0-6}$ alkyl)-;

R$^{1a}$, R$^{1b}$, and R$^{1c}$ are each independently —H, halogen, —C$_{1-6}$ alkyl, or —C$_{1-6}$ haloalkyl;

R$^{2a}$ and R$^{2b}$ are each independently:
(1) —H,
(2) —C$_{1-6}$ alkyl, optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —O—C$_{1-6}$ alkyl, —O—C$_{1-6}$ haloalkyl, —CN, —NO$_2$, —N(R$^a$R$^b$), —C(=O)N(R$^a$R$^b$), —C(=O)R$^a$, —CO$_2$R$^a$, —OCO$_2$R$^a$, —OCO$_2$R$^a$, —S(O)$_n$R$^a$, —SO$_2$N(R$^a$R$^b$), —N(R$^a$)C(=O)R$^b$, —N(R$^a$)CO$_2$R$^b$, —N(R$^a$)SO$_2$R$^b$, or —N(R$^a$)SO$_2$N(R$^a$R$^b$),
(3) —C$_{1-6}$ alkyl substituted with one substituent which is —C$_{3-8}$ cycloalkyl, aryl, or heteroaryl, wherein:
   (a) the cycloalkyl is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —C$_{1-6}$ alkyl, —C$_{1-6}$ alkyl-O—C$_{1-6}$ alkyl, —C$_{1-6}$ haloalkyl, —O—C$_{1-6}$ alkyl, —O—C$_{1-6}$ haloalkyl, or phenyl;
   (b) the aryl is an aromatic carbocyclic ring or an aromatic carbocyclic fused ring system, wherein the aryl is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —C$_{1-6}$ alkyl, —C$_{1-6}$ alkyl-O—C$_{1-6}$ alkyl, —C$_{1-6}$ haloalkyl, —O—C$_{1-6}$ alkyl, —O—C$_{1-6}$ haloalkyl, —CN, —NO$_2$, —N(R$^a$R$^b$), —C$_{1-6}$ alkyl-N(R$^a$R$^b$), —C(=O)N(R$^a$R$^b$), —C$_{1-6}$ alkyl-C(=O)N(R$^a$R$^b$), —C(=O)R$^a$, —C$_{1-6}$ alkyl-C(=O)R$^a$, —CO$_2$R$^a$, —C$_{1-6}$ alkyl-CO$_2$R$^a$, —OCO$_2$R$^a$, —C$_{1-6}$ alkyl-OCO$_2$R$^a$, —S(O)$_n$R$^a$, —C$_{1-6}$ alkyl-S(O)$_n$R$^a$, —SO$_2$N(R$^a$R$^b$), —C$_{1-6}$ alkyl-SO$_2$N(R$^a$R$^b$), —N(R$^a$)SO$_2$R$^b$, —C$_{1-6}$ alkyl-N(R$^a$)SO$_2$R$^b$, —N(R$^a$)C(=O)R$^b$, —C$_{1-6}$ alkyl-N(R$^a$)C(=O)R$^b$, —N(R$^a$)CO$_2$R$^b$, —C$_{1-6}$ alkyl-N(R$^a$)CO$_2$R$^b$, —N(R$^a$)SO$_2$N(R$^a$R$^b$), —C$_{1-6}$ alkyl-N(R$^a$)SO$_2$N(R$^a$R$^b$), phenyl, —C$_{1-6}$ alkyl-phenyl, —O-phenyl, —C$_{1-6}$ alkyl-O-phenyl, HetA, or —C$_{1-6}$ alkyl-HetA; wherein each HetA is a 5- or 6-membered heteroaromatic ring containing from 1 to 4 heteroatoms independently selected from N, O and S, wherein the heteroaromatic ring is optionally fused with a benzene ring; and wherein each HetA is optionally substituted with one or more substituents (e.g., optionally from 1 to 4, or 1 to 3, or 1 or 2 substituents; or is optionally mono-substituted) each of which is independently —C$_{1-6}$ alkyl, —C$_{1-6}$ haloalkyl, —O—C$_{1-6}$ alkyl, —O—C$_{1-6}$ haloalkyl, oxo, or —CO$_2$R$^a$; and
   (c) the heteroaryl is a 5- or 6-membered heteraromatic ring containing from 1 to 4 heteroatoms or a 9- or 10-membered bicyclic heteroaromatic ring system containing from 1 to 6 heteroatoms, wherein the heteroatoms in the heteroaryl are independently selected from N, O and S; and wherein the heteroaryl is optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —C$_{1-6}$ alkyl, —C$_{1-6}$ alkyl-O—C$_{1-6}$ alkyl, —C$_{1-6}$ haloalkyl, —O—C$_{1-6}$ alkyl, —O—C$_{1-6}$ haloalkyl, —N(R$^a$R$^b$), —C$_{1-6}$ alkyl-N(R$^a$R$^b$), —C(=O)N(R$^a$R$^b$), —C$_{1-6}$ alkyl-C(=O)N(R$^a$R$^b$), —C(=O)R$^a$, —C$_{1-6}$ alkyl-C(=O)R$^a$, —CO$_2$R$^a$, —C$_{1-6}$ alkyl-CO$_2$R$^a$, —OCO$_2$R$^a$, —C$_{1-6}$ alkyl-OCO$_2$R$^a$, —S(O)$_n$R$^a$, —C$_{1-6}$ alkyl-S(O)$_n$R$^a$, —SO$_2$N(R$^a$R$^b$), —C$_{1-6}$ alkyl-SO$_2$N(R$^a$R$^b$), —N(R$^a$)SO$_2$R$^b$, —C$_{1-6}$ alkyl-N(R$^a$)SO$_2$R$^b$, —N(R$^a$)C(=O)R$^b$, —C$_{1-6}$ alkyl-N(R$^a$)C(=O)R$^b$, —N(R$^a$)CO$_2$R$^b$, —C$_{1-6}$ alkyl-N(R$^a$)CO$_2$R$^b$, phenyl, —C$_{1-6}$ alkyl-phenyl, or oxo;
(4) —O—C$_{1-6}$ alkyl, optionally substituted with one or more substituents (e.g., optionally from 1 to 4, or 1 to 3, or 1 or 2 substituents; or is optionally mono-substituted) each of which is independently halogen, —OH, —O—C$_{1-6}$ alkyl, —O—C$_{1-6}$ haloalkyl, —S(O)$_n$R$^a$, —N(R$^a$)—CO$_2$R$^b$, or —C(=O)N(R$^a$R$^b$),
(5) —OH,
(6) halo,
(7) —NO$_2$,
(8) —CN,
(9) —C(=O)R$^a$,
(10) —CO$_2$R$^a$,
(11) —S(O)$_n$R$^a$,
(12) —SO$_2$N(R$^a$R$^b$),
(13) —N(R$^a$R$^b$),
(14) —C(=O)N(R$^a$R$^b$),
(15) —N(R$^a$)SO$_2$R$^b$,
(16) —OC(=O)N(R$^a$R$^b$),
(17) —N(R$^a$)C(=O)NR$^a$R$^b$),
(18) —N(R$^a$)—C$_{1-6}$ alkyl-C(=O)N(R$^a$R$^b$),
(19) —N(R$^a$)—C(=O)—C$_{1-6}$ alkyl-N(R$^a$R$^b$),
(20) —N(R$^a$)C(=O)—C(=O)N(R$^a$R$^b$),
(21) —OCO$_2$R$^a$,
(22) —N(R$^a$)—SO$_2$N(R$^a$R$^b$),
(23) —N(R$^a$)—SO$_2$—C$_{1-6}$ alkyl-N(R$^a$R$^b$),
(24) —N(R$^a$)C(=O)R$^b$,
(25) —N(R$^a$)CO$_2$R$^b$,
(26) —S—C$_{1-6}$ alkyl-C(=O)N(R$_a$R$_b$), or
(27) —N(SO$_2$R$^a$)—C$_{1-6}$ alkyl-C(=O)N(R$^a$R$^b$);

R$^3$ is
(1) —H,
(2) —C$_{1-6}$ alkyl, optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —O—C$_{1-6}$ alkyl, —O—C$_{1-6}$ haloalkyl, —CN, —NO$_2$, —N(R$^a$R$^b$), —C(=O)N(R$^a$R$^b$), —OC(=O)N(R$^a$R$^b$), —N(R$^a$)C(=O)N(R$^a$R$^b$), —N(R$_a$)—C$_{1-6}$ alkyl-C(=O)N(R$^a$R$^b$), —N(R$^a$)—C(=O)—C$_{1-6}$ alkyl-N(R$^a$R$^b$), —N(R$^a$)C(=O)—C(=O)N(R$^a$R$^b$), —C(=O)R$^a$, —CO$_2$R$^a$, —OCO$_2$R$^a$, —S(O)$_n$R$^a$, —SO$_2$N(R$^a$R$^b$), —N(R$^a$)—SO$_2$N(R$^a$R$^b$), —N(R$_a$)—SO$_2$—C$_{1-6}$ alkyl-N(R$^a$R$^b$), —N(R$^a$)C(=O)R$^b$, —N(R$^a$)CO$_2$R$^b$, —N(R$^a$)SO$_2$R$^b$, or -G-C$_{1-6}$ alkyl-C(=O)N(R$^a$R$^b$) wherein G is O or S or N(SO$_2$R$^a$),
with the proviso that none of the following substituents is attached to the carbon in the —C$_{1-6}$ alkyl group that is attached to (i.e., alpha to) the ring nitrogen: —OH, —O—C$_{1-6}$ alkyl, —O—C$_{1-6}$ haloalkyl, —NO$_2$, —N(R$^a$R$^b$), —OC(=O)N(R$^a$R$^b$), —N(R$^a$)C(=O)N(R$^a$R$^b$), —N(R$^a$)—C$_{1-6}$ alkyl-C(=O)N(R$^a$R$^b$), —N(R$^a$)—C(=O)—C$_{1-6}$ alkyl-N(R$^a$R$^b$), —N(R$^a$)C(=O)—C(=O)N(R$^a$R$^b$), —OCO$_2$R$^a$, —N($R^a$)—SO$_2$N($R^a R^b$), —N($R^a$)—SO$_2$—C$_{1-6}$ alkyl-N($R^a R^b$), —N($R^a$)C(=O)$R^b$, —N($R^a$)CO$_2 R^b$, —N($R^a$)SO$_2 R^b$, or -G-C$_{1-6}$ alkyl-C(=O)N($R^a R^b$) wherein G is O or N(SO$_2 R^a$),
(3) —C$_{1-6}$ alkyl substituted with one of:
  (i) —$R^k$,
  (ii) —S(O)$_n$—$R^k$,
  (iii) —S(O)$_n$—C$_{1-6}$ alkyl-$R^k$,
  (iv) —C(=O)—$R^k$,
  (v) —C(=O)—C$_{1-6}$ alkyl-$R^k$,
  (vi) —C(=O)N($R^a$)—$R^k$, or
  (vii) —C(=O)N($R^a$)—C$_{1-6}$ alkyl-$R^k$,
(4) —C$_{2-6}$ alkyl substituted with one of:
  (i) —O—$R^k$,
  (ii) —O—C$_{1-6}$ alkyl-$R^k$,
  (iii) —N($R^a$)—$R^k$,
  (iv) —N($R^a$)—C$_{1-6}$ alkyl-$R_k$,
  (v) —N($R^a$)C(=O)—$R^k$,
  (vi) —N($R^a$)C(=O)—C$_{1-6}$ alkyl-$R^k$,
with the proviso that the substituent is not attached to the carbon in the —C$_{2-6}$ alkyl group that is attached to (i.e., alpha to) the ring nitrogen,
(5) —S(O)$_n R^a$,
(6) —SO$_2$N($R^a R^b$),
(7) —C$_{2-6}$ alkenyl, optionally substituted with one substituent which is —C(=O)—N($R^a R^b$) or —$R^k$,
(8) —C$_{2-5}$ alkynyl, optionally substituted with one substituent which is —CH$_2$N($R^a R^b$), —CH$_2$O$R^a$, or —$R^k$,
(9) —$R^k$,
(10) —S(O)$_n$—C$_{1-6}$ alkyl-$R^k$,
(11) —N($R^a$)C(=O)—$R^k$, or
(12) —N($R^a$)C(=O)—C$_{1-6}$ alkyl-$R^k$;
each of $R^4$ and $R^5$ is independently
(1) —H,
(2) —C$_{1-6}$ alkyl, optionally substituted with one or more substituents (e.g., optionally from 1 to 6, or 1 to 5, or 1 to 4, or 1 to 3, or 1 or 2 substituents; or is optionally mono-substituted) each of which is independently halogen, —OH, —O—C$_{1-6}$ alkyl, —O—C$_{1-6}$ haloalkyl, —CN, —NO$_2$, —N($R^a R^b$), —C(=O)N($R^a R^b$), —OC(=O)N($R^a R^b$), —N($R^a$)C(=O)N($R^a R^b$), —N($R_a$)—C$_{1-6}$ alkyl-C(=O)N($R^a R^b$), —N($R^a$)—C(=O)—C$_{1-6}$ alkyl-N($R^a R^b$), —N($R^a$)C(=O)—C(=O)N($R^a R^b$), —C(=O)$R^a$, —CO$_2 R^a$, —OCO$_2 R^a$, —S(O)$_n R^a$, —SO$_2$N($R^a R^b$), —N($R^a$)—SO$_2$N($R^a R^b$), —N($R_a$)—SO$_2$—C$_{1-6}$ alkyl-N($R^a R^b$), —N($R^a$)C(=O)$R^b$, —N($R^a$)CO$_2 R^b$, —N($R^a$)SO$_2 R^b$, or -G-C$_{1-6}$ alkyl-C(=O)N($R^a R^b$) wherein G is O or S or N(SO$_2 R^a$),
(3) —SO$_2$N($R^a R^b$), or
(4) —C$_{1-6}$ alkyl-$R^m$;
each $R^a$ and $R^b$ is independently —H, —C$_{1-6}$ alkyl, or —C$_{3-8}$ cycloalkyl;
$R^k$ is a carbocycle or a heterocycle;
each $R^m$ is independently a carbocycle or a heterocycle;
each carbocycle is independently (i) a C$_3$ to C$_8$ monocyclic, saturated or unsaturated ring, (ii) a C$_7$ to C$_{12}$ bicyclic ring system, or (iii) a C$_{11}$ to C$_{16}$ tricyclic ring system, wherein each ring in (ii) or (iii) is independent of or fused to the other ring or rings and each ring is saturated or unsaturated; wherein the carbocycle is optionally substituted with one or more substituents (e.g., optionally from 1 to 6, or 1 to 5, or 1 to 4, or 1 to 3, or 1 or 2 substituents; or is optionally mono-substituted) each of which is independently
(1) halogen,
(2) —OH,
(3) —C$_{1-6}$ alkyl, optionally substituted with one or more substituents (e.g., optionally from 1 to 6, or 1 to 5, or 1 to 4, or 1 to 3, or 1 or 2 substituents; or is optionally mono-substituted) each of which is independently —OH, —O—C$_{1-6}$ alkyl, —O—C$_{1-6}$ haloalkyl, —CN, —NO$_2$, —N($R^a R^b$), —C(=O)N($R^a R^b$), —C(=O)$R^a$, —CO$_2 R^a$, —OCO$_2 R^a$, —S(O)$_n R^a$, —SO$_2$N($R^a R^b$), —N($R^a$)SO$_2 R^b$, —N($R^a$)C(=O)$R^b$, —N($R^a$)CO$_2 R^b$, —N($R^a$)SO$_2 R^b$, phenyl, —O-phenyl, or HetB,
(4) —C$_{1-6}$ haloalkyl,
(5) —O—C$_{1-6}$ alkyl,
(6) —O—C$_{1-6}$ haloalkyl,
(7) —CN,
(8) —NO$_2$,
(9) —N($R^a R^b$),
(10) —C(=O)N($R^a R^b$),
(11) —C(=O)$R^a$,
(12) —CO$_2 R^a$,
(13) —OCO$_2 R^a$,
(14) —S(O)$_n R^a$,
(15) —N($R^a$)SO$_2 R^b$,
(16) —SO$_2$N($R^a R^b$),
(17) —N($R^a$)C(=O)$R^b$,
(18) —N($R^a$)CO$_2 R^b$,
(19) phenyl,
(20) —O-phenyl, or
(21) HetB,
wherein each HetB is independently a 5- or 6-membered heteroaromatic ring containing from 1 to 4 heteroatoms independently selected from N, O and S, wherein the heteroaromatic ring is optionally fused with a benzene ring; and wherein each HetB is optionally substituted with one or more substituents (e.g., optionally from 1 to 4, or 1 to 3, or 1 or 2 substituents; or is optionally mono-substituted) each of which is independently —C$_{1-6}$ alkyl, —C$_{1-6}$ haloalkyl, —O—C$_{1-6}$ alkyl, —O—C$_{1-6}$ haloalkyl, oxo, or —CO$_2 R^a$;
each heterocycle is independently (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; the monocyclic ring, bicyclic ring system, or tricyclic ring system contains from 1 to 6 heteroatoms independently selected from N, O and S; and wherein any one or more of the nitrogen and sulfur heteroatoms is optionally oxidized, and any one or more of the nitrogen heteroatoms is optionally quaternized; wherein the heterocycle is optionally substituted with one or more substituents (e.g., optionally from 1 to 6, or 1 to 5, or 1 to 4, or 1 to 3, or 1 or 2 substituents; or is optionally mono-substituted) each of which is independently
(1) halogen,
(2) —OH,
(3) —C$_{1-6}$ alkyl, optionally substituted with one or more substituents (e.g., optionally from 1 to 6, or 1 to 5, or 1 to 4, or 1 to 3, or 1 or 2 substituents; or is optionally mono-substituted) each of which is independently —OH, —O—C$_{1-6}$ alkyl, —CN, —NO$_2$, —N($R^a R^b$), —C(=O)N($R^a R^b$), —C(=O)$R^a$, —CO$_2 R^a$, —S(O)$_n R^a$, —N($R^a$)SO$_2 R^b$, —SO$_2$N($R^a R^b$), —N($R^a$)C(=O)$R^b$, —N($R^a$)CO$_2 R^b$, phenyl, —O-phenyl, or HetC,
(4) —C$_{1-6}$ haloalkyl,
(5) —O—C$_{1-6}$ alkyl,
(6) —O—C$_{1-6}$ haloalkyl, (7) —CN,
(8) —$NO_2$,
(9) —$N(R^aR^b)$,
(10) —$C(=O)N(R^aR^b)$,
(11) —$C(=O)R^a$,
(12) —$CO_2R^a$,
(13) —$OCO_2R^a$,
(14) —$S(O)_nR^a$,
(15) —$N(R^a)SO_2R^b$,
(16) —$SO_2N(R^aR^b)$,
(17) —$N(R^a)C(=O)R^b$,
(18) —$N(R^a)CO_2R^b$,
(19) phenyl,
(20) —O-phenyl,
(21) HetC, or
(22) oxo;

wherein each HetC is independently a 5- or 6-membered heteroaromatic ring containing from 1 to 4 heteroatoms independently selected from N, O and S, wherein the heteroaromatic ring is optionally fused with a benzene ring; and wherein each HetC is optionally substituted with one or more substituents (e.g., optionally from 1 to 4, or 1 to 3, or 1 or 2 substituents; or is optionally mono-substituted) each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$; and each n is independently an integer equal to 0, 1 or 2;

or a pharmaceutically acceptable salt thereof.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes the 4-hydroxy-1,5-naphthyridin-2-one 3-carboxamiides of Formula (I) above. These compounds and pharmaceutically acceptable salts thereof are HIV integrase inhibitors.

A first embodiment of the present invention is a compound of Formula (I), wherein $R^{1a}$, $R^{1b}$, and $R^{1c}$ are each independently —H, fluoro, chloro, bromo, —$C_{1-4}$ alkyl, or —$CF_3$;

and all other variables are as originally defined;

or a pharmaceutically acceptable salt thereof.

A second embodiment of the present invention is a compound of Formula (I), wherein $R^{1a}$ and $R^{1c}$ are both —H; and $R^{1b}$ is —H, halogen, —$C_{1-6}$ alkyl, or —$C_{1-6}$ haloalkyl;

and all other variables are as originally defined;

or a pharmaceutically acceptable salt thereof.

In an aspect of the second embodiment, $R^{1a}$ and $R^{1c}$ are both —H; and $R^{1b}$ is fluoro, chloro, bromo, —$C_{1-4}$ alkyl, or —$CF_3$. In still another aspect of the preceding embodiment, $R^{1a}$ and $R^{1c}$ are both —H; and $R^{1b}$ is fluoro.

A third embodiment of the present invention is a compound of Formula (I), wherein one of $R^{2a}$ and $R^{2b}$ is —H, and the other of $R^{2a}$ and $R^{2b}$ is as originally defined above;

and all other variables are as originally defined above;

or a pharmaceutically acceptable salt thereof.

A fourth embodiment of the present invention is a compound of Formula (I), wherein $R^{2a}$ and $R^{2b}$ are each independently:

(1) —H,
(2) —$C_{1-6}$ alkyl, optionally substituted with from 1 to 5 substituents each of which is independently halogen, —OH, —O—$C_{1-4}$ alkyl, —O—$C_{1-4}$ haloalkyl, —CN, —$NO_2$, —$N(R^aR^b)$, —$C(=O)N(R^aR^b)$, —$C(=O)R^a$, —$CO_2R^a$, —$OCO_2R^a$, —$S(O)_nR^a$, —$SO_2N(R^aR^b)$, —$N(R^a)C(=O)R^b$, —$N(R^a)CO_2R^b$, —$N(R^a)SO_2R^b$, or —$N(R^a)SO_2N(R^aR^b)$,
(3) —$C_{1-6}$ alkyl substituted with one substituent which is —$C_{3-8}$ cycloalkyl, aryl, or heteroaryl, wherein:
  (a) the cycloalkyl is optionally substituted with from 1 to 5 substituents each of which is independently halogen, —OH, —$C_{1-4}$ alkyl, —$C_{1-4}$ alkyl-O—$C_{1-4}$ alkyl, —$C_{1-4}$ haloalkyl, —O—$C_{1-4}$ alkyl, —O—$C_{1-4}$ haloalkyl, or phenyl;
  (b) the aryl is an aromatic carbocyclic ring or an aromatic carbocyclic fused ring system, wherein the aryl is optionally substituted with from 1 to 5 substituents each of which is independently halogen, —OH, —$C_{1-4}$ alkyl, —$C_{1-4}$ alkyl-O—$C_{1-4}$ alkyl, —$C_{1-4}$ haloalkyl, —O—$C_{1-4}$ alkyl, —O—$C_{1-4}$ haloalkyl, —CN, —$NO_2$, —$N(R^aR^b)$, —$C_{1-4}$ alkyl-$N(R^aR^b)$, —$C(=O)N(R^aR^b)$, —$C_{1-4}$ alkyl-$C(=O)N(R^aR^b)$, —$C(=O)R^a$, —$C_{1-4}$ alkyl-$C(=O)R^a$, —$CO_2R^a$, —$C_{1-4}$ alkyl-$CO_2R^a$, —$OCO_2R^a$, —$C_{1-4}$ alkyl-$OCO_2R^a$, —$S(O)_nR^a$, —$C_{1-4}$ alkyl-$S(O)_nR^a$, —$SO_2N(R^aR^b)$, —$C_{1-4}$ alkyl-$SO_2N(R^aR^b)$, —$N(R^a)SO_2R^b$, —$C_{1-4}$ alkyl-$N(R^a)SO_2R^b$, —$N(R^a)C(=O)R^b$, —$C_{1-4}$ alkyl-$N(R^a)C(=O)R^b$, —$N(R^a)CO_2R^b$, —$C_{1-4}$ alkyl-$N(R^a)CO_2R^b$, —$N(R^a)SO_2N(R^aR^b)$, —$C_{1-4}$ alkyl-$N(R^a)SO_2N(R^aR^b)$, phenyl, —$C_{1-4}$ alkyl-phenyl, —O-phenyl, —$C_{1-4}$ alkyl-O-phenyl, HetA, or —$C_{1-4}$ alkyl-HetA; wherein each HetA is a 5- or 6-membered heteroaromatic ring containing from 1 to 4 heteroatoms independently selected from N, O and S, wherein the heteroaromatic ring is optionally fused with a benzene ring; and wherein each HetA is optionally substituted with from 1 to 4 substituents each of which is independently —$C_{1-4}$ alkyl, —$C_{1-4}$ haloalkyl, —O—$C_{1-4}$ alkyl, —O—$C_{1-4}$ haloalkyl, oxo, or —$CO_2R^a$; and
  (c) the heteroaryl is a 5- or 6-membered heteraromatic ring containing from 1 to 4 heteroatoms or a 9- or 10-membered bicyclic heteroaromatic ring system containing from 1 to 6 heteroatoms, wherein the heteroatoms in the heteroaryl are independently selected from N, O and S; and wherein the heteroaryl is optionally substituted with from 1 to 5 substituents each of which is independently halogen, —OH, —$C_{1-4}$ alkyl, —$C_{1-4}$ alkyl-O—$C_{1-4}$ alkyl, —$C_{1-4}$ haloalkyl, —O—$C_{1-4}$ alkyl, —O—$C_{1-4}$ haloalkyl, —$N(R^aR^b)$, —$C_{1-4}$ alkyl-$N(R^aR^b)$, —$C(=O)N(R^aR^b)$, —$C_{1-4}$ alkyl-$C(=O)N(R^aR^b)$, —$C(=O)R^a$, —$C_{1-4}$ alkyl-$C(=O)R^a$, —$CO_2R^a$, —$C_{1-4}$ alkyl-$CO_2R^a$, —$OCO_2R^a$, —$C_{1-4}$ alkyl-$OCO_2R^a$, —$S(O)_nR^a$, —$C_{1-4}$ alkyl-$S(O)_nR^a$, —$SO_2N(R^aR^b)$, —$C_{1-4}$ alkyl-$SO_2N(R^aR^b)$, —$N(R^a)SO_2R^b$, —$C_{1-4}$ alkyl-$N(R^a)SO_2R^b$, —$N(R^a)C(=O)R^b$, —$C_{1-4}$ alkyl-N($R^a$)C(=O)$R^b$, —N($R^a$)$CO_2R^b$, —$C_{1-4}$ alkyl-N($R^a$)$CO_2R^b$, phenyl, —$C_{1-4}$ alkyl-phenyl, or oxo;
(4) —O—$C_{1-6}$ alkyl, optionally substituted with from 1 to 5 substituents each of which is independently halogen, —OH, —O—$C_{1-4}$ alkyl, —O—$C_{1-4}$ haloalkyl, —S(O)$_n$$R^a$, —N($R^a$)—$CO_2R^b$, or —C(=O)N($R^aR^b$),
(5) —OH,
(6) halo,
(7) —$NO_2$,
(8) —CN,
(9) —C(=O)$R^a$,
(10) —$CO_2R^a$,
(11) —S(O)$_n$$R^a$,
(12) —$SO_2$N($R^aR^b$),
(13) —N($R^aR^b$),
(14) —C(=O)N($R^aR^b$),
(15) —N($R^a$)$SO_2R^b$,
(16) —OC(=O)N($R^aR^b$),
(17) —N($R^a$)C(=O)N($R^aR^b$),
(18) —N($R^a$)—$C_{1-6}$ alkyl-C(=O)N($R^aR^b$),
(19) —N($R^a$)—C(=O)—$C_{1-6}$ alkyl-N($R^aR^b$),
(20) —N($R^a$)C(=O)—C(=O)N($R^aR^b$),
(21) —$OCO_2R^a$,
(22) —N($R^a$)—$SO_2$N($R^aR^b$),
(23) —N($R^a$)—$SO_2$—$C_{1-6}$ alkyl-N($R^aR^b$),
(24) —N($R^a$)C(=O)$R^b$,
(25) —N($R^a$)$CO_2R^b$,
(26) —S—$C_{1-6}$ alkyl-C(=O)N($R^aR^b$), or
(27) —N($SO_2R^a$)—$C_{1-6}$ alkyl-C(=O)N($R^aR^b$);

and all other variables are as originally defined above;
or a pharmaceutically acceptable salt thereof.

A fifth embodiment of the present invention is a compound of Formula (I), wherein $R^{2a}$ and $R^{2b}$ are each independently:
(1) —H,
(2) —$C_{1-4}$ alkyl, optionally substituted with 1 or 2 substituents each of which is independently —OH, —O—$C_{1-4}$ alkyl, —O—$CF_3$, —CN, —$NO_2$, —N($R^aR^b$), —C(=O)N($R^aR^b$), —C(=O)$R_a$, —$CO_2R^a$, —$OCO_2R^a$, —S(O)$_n$$R^a$, —$SO_2$N($R^aR^b$), —N($R^a$)C(=O)$R^b$, —N($R^a$)$CO_2R^b$, or —N($R^a$)$SO_2R^b$,
(3) —$CF_3$,
(4) —$C_{1-4}$ alkyl substituted with one of —$C_{3-6}$ cycloalkyl, aryl, or heteroaryl, wherein:
  the cycloalkyl is optionally substituted with 1 or 2 substituents each of which is independently fluoro, chloro, bromo, —OH, —$C_{1-4}$ alkyl, —($CH_2$)$_{1-2}$—O—$C_{1-4}$ alkyl, —$CF_3$, —O—$C_{1-4}$ alkyl, —$OCF_3$, or phenyl;
  the aryl is phenyl, naphthyl, anthryl, or phenanthryl; wherein the aryl is optionally substituted with from 1 to 3 substituents each of which is independently fluoro, chloro, bromo, —OH, —$C_{1-4}$ alkyl, —($CH_2$)$_{1-2}$—O—$C_{1-4}$ alkyl, —$CF_3$, —O—$C_{1-4}$ alkyl, —$OCF_3$, —CN, —$NO_2$, —N($R^aR^b$), —$C_{1-4}$ alkyl-N($R^aR^b$), —C(=O)N($R^aR^b$), —$C_{1-4}$ alkyl-C(=O)N($R^aR^b$), —C(=O)$R^a$, —$C_{1-4}$ alkyl-C(=O)$R^a$, —$CO_2R^a$, —$C_{1-4}$ alkyl-$CO_2R^a$, —$OCO_2R^a$, —$C_{1-4}$ alkyl-$OCO_2R^a$, —S(O)$_n$$R^a$, —$C_{1-4}$ alkyl-S(O)$_n$$R^a$, —$SO_2$N($R^aR^b$), —$C_{1-4}$ alkyl-$SO_2$N($R^aR^b$), —N($R^a$)$SO_2R^b$, —$C_{1-4}$ alkyl-N($R^a$)$SO_2R^b$, —N($R^a$)C(=O)$R^b$, —$C_{1-4}$ alkyl-N($R^a$)C(=O)$R^b$, —N($R^a$)$CO_2R^b$, —$C_{1-4}$ alkyl-N($R^a$)$CO_2R^b$, —N($R^a$)$SO_2$N($R^aR^b$), —$C_{1-4}$ alkyl-N($R^a$)$SO_2$N($R^aR^b$), phenyl, —$C_{1-4}$ alkyl-phenyl, —O-phenyl, —$C_{1-4}$ alkyl-O-phenyl, HetA, or —$C_{1-4}$ alkyl-HetA; wherein each HetA is a 5- or 6-membered heteroaromatic ring containing from 1 to 4 heteroatoms independently selected from N, O and S, wherein the heteroaromatic ring is optionally fused with a benzene ring; and wherein each HetA is optionally substituted with from 1 to 4 substituents each of which is independently —$C_{1-4}$ alkyl, —$CF_3$, —O—$C_{1-4}$ alkyl, —$OCF_3$, oxo, or —$CO_2R^a$; and
  the heteroaryl is a 5- or 6-membered heteroaromatic ring containing from 1 to 4 heteroatoms independently selected from N, O and S; wherein the heteroaryl is optionally substituted with 1 or 2 substituents each of which is independently fluoro, chloro, bromo, —OH, —$C_{1-4}$ alkyl, —($CH_2$)$_{1-2}$—O—$C_{1-4}$ alkyl, —$CF_3$, —O—$C_{1-4}$ alkyl, —$OCF_3$, —N($R^aR^b$), —$C_{1-4}$ alkyl-N($R^aR^b$), —C(=O)N($R^aR^b$), —$C_{1-4}$ alkyl-C(=O)N($R^aR^b$), —C(=O)$R^a$, —$C_{1-4}$ alkyl-C(=O)$R^a$, —$CO_2R^a$, —$C_{1-4}$ alkyl-$CO_2R^a$, —$OCO_2R^a$, —$C_{1-4}$ alkyl-$OCO_2R^a$, —S(O)$_n$$R^a$, —$SO_2$N($R^aR^b$), —$C_{1-4}$ alkyl-S(O)$_n$$R^a$, —$SO_2$N($R^aR^b$), —N($R^a$)$SO_2R^b$, —$C_{1-4}$ alkyl-N($R^a$)$SO_2R^b$, —N($R^a$)C(=O)$R^b$, —$C_{1-4}$ alkyl-N($R^a$)C(=O)$R^b$, —N($R^a$)$CO_2R^b$, —$C_{1-4}$ alkyl-N($R^a$)$CO_2R^b$, phenyl, —$C_{1-4}$ alkyl-phenyl, or oxo;
(5) —O—$C_{1-6}$ alkyl, optionally substituted with 1 or 2 substituents each of which is independently —OH, —O—$C_{1-4}$ alkyl, —$OCF_3$, —S(O)$_n$$R^a$, or —NH—$CO_2R^a$, or —C(=O)N($R^aR^b$),
(6) —$OCF_3$,
(7) —OH,
(8) fluoro, chloro, or bromo,
(9) —$NO_2$,
(10) —CN,
(11) —C(=O)$R^a$,
(12) —$CO_2R^a$,
(13) —S(O)$_n$$R^a$,
(14) —$SO_2$N($R^aR^b$),
(15) —N($R^aR^b$),
(16) —C(=O)N($R^aR^b$),
(17) —N($R^a$)$SO_2R^b$, or
(18) —N($R^a$)C(=O)$R^b$;

and all other variables are as originally defined;
or a pharmaceutically acceptable salt thereof.

A sixth embodiment of the present invention is a compound of Formula (I), wherein $R^{2a}$ and $R^{2b}$ are each independently:
(1) —H,
(2) —$C_{1-4}$ alkyl,
(3) —$C_{1-2}$ alkyl substituted with one substituent which is —OH, $OCH_3$, —CN, —N($R^aR^b$), —C(=O)N($R^aR^b$), —C(=O)$R^a$, —$CO_2R^a$, —$SR^a$, —$SO_2R^a$, —$SO_2$N($R^aR^b$), —N($R^a$)C(=O)$R^b$, —N($R^a$)$CO_2R^b$, or —N($R^a$)$SO_2R^b$,
(4) —$CF_3$,
(5) —$CH_2$-cyclopropyl,
(6) —$CH_2$-phenyl, wherein the phenyl is optionally substituted with from 1 to 3 substituents each of which is independently fluoro, chloro, bromo, —$C_{1-4}$ alkyl, —$CH_2OCH_3$, —$CF_3$, —O—$C_{1-4}$ alkyl, —$OCF_3$, —CN, —N($R^aR^b$), —C(=O)N($R^aR^b$), —C(=O)$R^a$, —$CO_2R^a$, or —S(O)$_n$$R^a$;
(7) —$CH_2$-heteroaryl, wherein the heteroaryl is pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, or thiadiazolyl; and wherein the heteroaryl is optionally substituted with 1 or 2 substituents each of which is independently fluoro, chloro, bromo, —$C_{1-4}$ alkyl, —O—$C_{1-4}$ alkyl, or oxo, (8) —O—$C_{1-4}$ alkyl,
(9) —$OCF_3$,
(10) —OH
(11) fluoro, chloro, or bromo,
(12) —$NO_2$,
(13) —CN,
(14) —C(=O)$R^a$,
(15) —$CO_2R^a$,
(16) —S(O)$_n R^a$,
(17) —$SO_2N(R^a R^b)$,
(18) —N($R^a R^b$),
(19) —C(=O)N($R^a R^b$),
(20) —N($R^a$)$SO_2 R^b$, or
(21) —N($R^a$)C(=O)$R^b$;

and all other variables are as originally defined;

or a pharmaceutically acceptable salt thereof.

In an aspect of each of the fifth and sixth embodiments, each $R^a$ and $R^b$ is independently —H or —$C_{1-4}$ alkyl. In another aspect of each of the fifth and sixth embodiments, one of $R^{2a}$ and $R^{2b}$ is —H, and the other of $R^{2a}$ and $R^{2b}$ is as just defined in the embodiment.

A seventh embodiment of the present invention is a compound of Formula (I), wherein $R^{2a}$ and $R^{2b}$ are each independently:
(1) —H,
(2) —$C_{1-4}$ alkyl,
(3) —$CF_3$,
(4) fluoro, chloro, or bromo,
(5) —$SO_2$—$C_{1-4}$ alkyl,
(6) —S—$C_{1-4}$ alkyl,
(7) —$SO_2$N(—$C_{1-4}$ alkyl)$_2$,
(8) —C(=O)N(—$C_{1-4}$ alkyl)$_2$,
(9) —$NHSO_2$—$C_{1-4}$ alkyl,
(10) —N(—$C_{1-4}$ alkyl)$SO_2$—$C_{1-4}$ alkyl,
(11) —NHC(=O)—$C_{1-4}$ alkyl,
(12) —N(—$C_{1-4}$ alkyl)C(=O)—$C_{1-4}$ alkyl, or
(13) —C(=O)NH(—$C_{1-4}$ alkyl);

and all other variables are as originally defined;

or a pharmaceutically acceptable salt thereof.

An eighth embodiment of the present invention is a compound of Formula (I), or a pharmaceutically acceptable salt thereof, wherein $R^{2a}$ and $R^{2b}$ are each independently one of groups (1) to (12) as defined in the seventh embodiment; and all other variables are as originally defined.

In an aspect of each of the seventh and eighth embodiments, one of $R^{2a}$ and $R^{2b}$ is —H, and the other of $R^{2a}$ and $R^{2b}$ is as just defined in the embodiment. In an aspect of the seventh embodiment, one of $R^{2a}$ and $R^{2b}$ is —H, and the other of $R^{2a}$ and $R^{2b}$ is:
(1) —H,
(2) —$SO_2CH_3$,
(3) —$SO_2CH_2CH_3$,
(4) —S—$CH_3$, or
(5) —S—$CH_2CH_3$.

In an aspect of the eighth embodiment, one of $R^{2a}$ and $R^{2b}$ is —H, and the other of $R^{2a}$ and $R^{2b}$ is:
(1) —H,
(2) —$SO_2CH_3$,
(3) —$SO_2CH_2CH_3$,
(4) —S—$CH_3$,
(5) —S—$CH_2CH_3$, or
(6) —C(=O)NH($CH_3$).

A ninth embodiment of the present invention is a compound of Formula (I), wherein $R^3$ is:
(1) —H,
(2) —$C_{1-6}$ alkyl, optionally substituted with from 1 to 5 substituents each of which is independently halogen, —OH, —O—$C_{1-4}$ alkyl, —O—$C_{1-4}$ haloalkyl, —CN, —$NO_2$, —N($R^a R^b$), —C(=O)N($R^a R^b$), —OC(=O)N($R^a R^b$), —N($R^a$)C(=O)N($R^a R^b$), —N($R^a$)—$C_{1-4}$ alkyl-C(=O)N($R^a R^b$), —N($R^a$)—C(=O)—$C_{1-4}$ alkyl-N($R^a R^b$), —N($R^a$)C(=O)—C(=O)N($R^a R^b$), —C(=O)$R^a$, —$CO_2R^a$, —$OCO_2R^a$, —S(O)$_n R^a$, —$SO_2N(R^a R^b)$, —N($R^a$)—$SO_2N(R^a R^b)$, —N($R^a$)—$SO_2$—$C_{1-4}$ alkyl-N($R^a R^b$), —N($R^a$)C(=O)$R^b$, —N($R^a$)$CO_2 R^b$, —N($R^a$)$SO_2 R^b$, or -G-$C_{1-4}$ alkyl-C(=O)N($R^a R^b$) wherein G is O or S or N($SO_2R^a$), with the proviso that none of the following substituents is attached to the carbon in the —$C_{1-6}$ alkyl group that is attached to the ring nitrogen: —OH, —O—$C_{1-6}$ alkyl, —O—$C_{1-6}$ haloalkyl, —$NO_2$, —N($R^a R^b$), —OC(=O)N($R^a R^b$), —N($R^a$)C(=O)N($R^a R^b$), —N($R^a$)—$C_{1-6}$ alkyl-C(=O)N($R^a R^b$), —N($R^a$)—C(=O)—$C_{1-6}$ alkyl-N($R^a R^b$), —N($R^a$)C(=O)—C(=O)N($R^a R^b$), —$OCO_2R^a$, —N($R^a$)—$SO_2N(R^a R^b)$, —N($R^a$)—$SO_2C_{1-6}$ alkyl-N($R^a R^b$), —N($R^a$)C(=O)$R^b$, —N($R^a$)$CO_2R^b$, —N($R^a$)$SO_2R^b$, or -G-$C_{1-6}$ alkyl-C(=O)N($R^a R^b$) wherein G is O or N($SO_2R^a$), (3) —$C_{1-6}$ alkyl substituted with one of:
(i) —$R^k$,
(ii) —S(O)$_n$—$R^k$,
(iii) —S(O)$_n$—$C_{1-4}$ alkyl-$R^k$,
(iv) —C(=O)—$R^k$,
(v) —C(=O)—$C_{1-4}$ alkyl-$R^k$,
(vi) —C(=O)N($R^a$)—$R^k$, or
(vii) —C(=O)N($R^a$)—$C_{1-4}$ alkyl-$R^k$, (4) —$C_{2-6}$ alkyl substituted with one of:
(i) —O—$R^k$,
(ii) —O—$C_{1-4}$ alkyl-$R^k$,
(iii) —N($R^a$)—$R^k$,
(iv) —N($R^a$)—$C_{1-4}$ alkyl-$R^k$,
(v) —N($R^a$)C(=O)—$R^k$,
(vi) —N($R^a$)C(=O)—$C_{1-4}$ alkyl-$R^k$, with the proviso that the substituent is not attached to the carbon in the —$C_{2-6}$ alkyl group that is attached to the ring nitrogen, (5) —S(O)$_n R^a$,
(6) —$SO_2N(R^a R^b)$,
(7) —$C_{2-4}$ alkenyl, optionally substituted with one substituent which is —C(=O)—N($R^a R^b$) or —$R^k$,
(8) —$C_{2-4}$ alkynyl, optionally substituted with one substituent which is —$CH_2$N($R^a R^b$), —$CH_2OR^a$, or —$R^k$,
(9) —$R^k$,
(10) —S(O)$_n$—$C_{1-4}$ alkyl-$R^k$,
(11) —N($R^a$)C(=O)—$R^k$; or
(12) —N($R^a$)C(=O)—$C_{1-4}$ alkyl-$R^k$;

and all other variables are as originally defined;

or a pharmaceutically acceptable salt thereof.

A tenth embodiment of the present invention is a compound of Formula (I), wherein $R^3$ is:
(1) —H,
(2) —$C_{1-4}$ alkyl, optionally substituted with one substituent which is —O—$C_{1-4}$ alkyl, —CN, —N($R^a R^b$), —C(=O)N($R^a R^b$), —OC(=O)N($R^a R^b$), —N($R^a$)C(=O)N($R^a R^b$), —N($R^a$)C(=O)$CH_2$N($R^a R^b$), —N($R^a$)C(=O)—C(=O)N($R^a R^b$), —C(=O)$R^a$, —$CO_2R^a$, —S(O)$_n R^a$, —$SO_2N(R^a R^b)$, —N($R^a$)$CO_2R^b$, —N($R^a$)—$SO_2N(R^a R^b)$, —N($R^a$)—$SO_2CH_2N(R^a R^b)$, or —N($R^a$)$SO_2R^b$, with the proviso that none of the following substituents is attached to the carbon in the —$C_{1-4}$ alkyl group that is attached to the ring nitrogen: —O—$C_{1-4}$ alkyl, —N($R^aR^b$), —OC(=O)N($R^aR^b$), —N($R^a$)C(=O)N($R^aR^b$), —N($R^a$)—C(=O)—$CH_2$N($R^aR^b$), —N($R^a$)C(=O)—C(=O)N($R^aR^b$), —N($R^a$)$CO_2R^b$, —N($R^a$)—$SO_2$N($R^aR^b$), —N($R^a$)—$SO_2$—$CH_2$N($R^aR^b$), or —N($R^a$)$SO_2R^b$, (3) —$C_{1-4}$ alkyl-$R^k$,
(4) —$C_{1-4}$ alkyl-C(=O)—$R^k$, or
(5) —$CH_{2-4}$ alkyl-N($R^a$)—C(=O)—$R_k$, with the proviso that the substituent is not attached to the carbon in the —$C_{2-4}$ alkyl group that is attached to the ring nitrogen;

and all other variables are as originally defined;

or a pharmaceutically acceptable salt thereof.

An eleventh embodiment of the present invention is a compound of Formula (I), wherein $R^3$ is:
(1) —H,
(2) —$C_{1-4}$ alkyl,
(3) —$(CH_2)_{2-3}$—O—$C_{1-4}$ alkyl,
(4) —$(CH_2)_{2-3}$—N(—$C_{1-4}$ alkyl)$_2$,
(5) —$(CH_2)_{1-3}$—C(=O)N(—$C_{1-4}$ alkyl)$_2$,
(6) —$(CH_2)_{2-3}$—OC(=O)N(—$C_{1-4}$ alkyl)$_2$,
(7) —$(CH_2)_{2-3}$—N(—$C_{1-4}$ alkyl)C(=O)N(—$C_{1-4}$ alkyl)$_2$,
(8) —$(CH_2)_{2-3}$—N(—$C_{1-4}$ alkyl)C(=O)—$CH_2$N(—$C_{1-4}$ alkyl)$_2$,
(9) —$(CH_2)_{2-3}$—N(—$C_{1-4}$ alkyl)C(=O)—C(=O)N(—$C_{1-4}$ alkyl)$_2$,
(10) —$(CH_2)_{1-3}$—$CO_2$—$C_{1-4}$ alkyl,
(11) —$(CH_2)_{1-3}$—S(O)$_n$—$C_{1-4}$ alkyl,
(12) —$(CH_2)_{1-3}$—$SO_2$N(—$C_{1-4}$ alkyl)$_2$,
(13) —$(CH_2)_{2-3}$—N(—$C_{1-4}$ alkyl)-$CO_2$—$C_{1-4}$ alkyl,
(14) —$(CH_2)_{2-3}$—N(—$C_{1-4}$ alkyl)-$SO_2$N(—$C_{1-4}$ alkyl)$_2$,
(15) —$(CH_2)_{2-3}$—N(—$C_{1-4}$ alkyl)-$SO_2CH_2$N(—$C_{1-4}$ alkyl)$_2$,
(16) —$(CH_2)_{2-3}$—N(—$C_{1-4}$ alkyl)-$SO_2$—$C_{1-4}$ alkyl,
(17) —$(CH_2)_{1-3}$—$R^k$,
(18) —$(CH_2)_{1-3}$—C(=O)—$R_k$, or
(19) —$(CH_2)_{2-3}$—N(—$C_{1-4}$ alkyl)-C(=O)—$R^k$;

and all other variables are as originally defined;

or a pharmaceutically acceptable salt thereof.

A twelfth embodiment of the present invention is a compound of Formula (I), wherein $R^k$ is:
(i) —$C_{3-8}$ cycloalkyl,
(ii) aryl selected from phenyl and naphthyl, wherein the aryl is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, —CN, —N($R^aR^b$), —C(=O)N($R^aR^b$), —C(=O)$R^a$, —$CO_2R^a$, —S(O)$_nR^a$, —$SO_2$N($R^aR^b$), —N($R^a$)C(=O)$R^b$, —N($R^a$)$CO_2R^b$, —N($R^a$)$SO_2R^b$, —$(CH_2)_{1-2}$—O—$C_{1-4}$ alkyl, —$(CH_2)_{1-2}$—O—$C_{1-4}$ haloalkyl, —$(CH_2)_{1-2}$—CN, —$(CH_2)_{1-2}$—N($R^aR^b$), —$(CH_2)_{1-2}$—C(=O)N($R^aR^b$), —$(CH_2)_{1-2}$—C(=O)$R^a$, —$(CH_2)_{1-2}$—$CO_2R^a$, —$(CH_2)_{1-2}$—S(O)$_nR^a$, —$(CH_2)_{1-2}$—$SO_2$N($R^aR^b$), —$(CH_2)_{1-2}$—N($R^a$)C(=O)$R^b$, —$(CH_2)_{1-2}$—N($R^a$)$CO_2R^b$, —$(CH_2)_{1-2}$—N($R^a$)$SO_2R^b$, phenyl, —$(CH_2)_{1-2}$-phenyl, HetB, or —$(CH_2)_{1-2}$HetB;
(iii) a 4- to 7-membered saturated heterocyclic ring containing from 1 to 4 heteratoms selected from N, O and S, wherein the saturated heterocyclic ring is optionally substituted with from 1 to 3 substituents each of which is independently halogen, —$C_{1-4}$ alkyl, oxo, phenyl, —$(CH_2)_{1-2}$-phenyl, HetC, or —$(CH_2)_{1-2}$HetC, or
(iv) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, —O—$C_{1-4}$ alkyl, phenyl, —$(CH_2)_{1-2}$-phenyl, HetC, or —$(CH_2)_{1-2}$-HetC;

and all other variables are as originally defined;

or a pharmaceutically acceptable salt thereof.

In an aspect of the twelfth embodiment, $R^3$ is as defined in the ninth embodiment. In another aspect of the twelfth embodiment, $R^3$ is as defined in the tenth embodiment. In still another aspect of the twelfth embodiment, $R^3$ is as defined in the eleventh embodiment.

A thirteenth embodiment of the present invention is a compound of Formula (I), wherein $R^k$ is:
(i) phenyl, which is optionally substituted with from 1 to 3 substituents each of which is independently halogen, —$C_{1-4}$ alkyl, —$C_{1-4}$ haloalkyl, —O—$C_{1-4}$ alkyl or —O—$C_{1-4}$ haloalkyl,
(ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;

and all other variables are as originally defined;

or a pharmaceutically acceptable salt thereof.

In an aspect of the thirteenth embodiment, $R^3$ is as defined in the ninth embodiment. In another aspect of the thirteenth embodiment, $R^3$ is as defined in the tenth embodiment. In still another aspect of the thirteenth embodiment, $R^3$ is as defined in the eleventh embodiment.

A fourteenth embodiment of the present invention is a compound of Formula (I), wherein $R^k$ is:
(i) phenyl which is optionally substituted with from 1 to 3 substituents each of which is independently fluoro, chloro, bromo, —$C_{1-4}$ alkyl, —$CF_3$, —O—$C_{1-4}$ alkyl, or —$OCF_3$;
(ii) a saturated heterocyclic ring selected from the group consisting of piperidinyl, piperazinyl, pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl, thiazinanyl, thiadiazinanyl, and dioxanyl; wherein the saturated heterocyclic ring is optionally substituted with from 1 to 3 substituents each of which is independently —$C_{1-4}$ alkyl or oxo; or
(iii) a heteroaromatic ring selected from the group consisting of pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl; wherein the heteroaromatic ring is optionally substituted with from 1 to 3 substituents each of which is independently halogen, —$C_{1-4}$ alkyl, or —O—$C_{1-4}$ alkyl;

and all other variables are as originally defined;

or a pharmaceutically acceptable salt thereof.

In an aspect of the fourteenth embodiment, $R^3$ is as defined in the ninth embodiment. In another aspect of the fourteenth embodiment, $R^3$ is as defined in the tenth embodiment. In still another aspect of the fourteenth embodiment, $R^3$ is as defined in the eleventh embodiment.

A fifteenth embodiment of the present invention is a compound of Formula (I), wherein each of $R^4$ and $R^5$ is independently:
(1) —H,
(2) —$C_{1-6}$ alkyl, optionally substituted with from 1 to 5 substituents each of which is independently halogen, —OH, —O—$C_{1-4}$ alkyl, —O—$C_{1-4}$ haloalkyl, —CN, —NO$_2$, —N($R^a R^b$), —C(=O)N($R^a R^b$), —OC(=O)N ($R^a R^b$), —N($R^a$)C(=O)N($R^a R^b$), —N($R^a$)—$C_{1-4}$ alkyl-C(=O)N($R^a R^b$), —N($R^a$)—C(=O)—$C_{1-4}$ alkyl-N ($R^a R^b$), —N($R^a$)C(=O)—C(=O)N($R^a R^b$), —C(=O) $R^a$, —CO$_2 R^a$, —OCO$_2 R^a$, —S(O)$_n R^a$, —SO$_2$N($R^a R^b$), —N($R^a$)—SO$_2$N($R^a R^b$), —N($R^a$)—SO$_2$—$C_{1-4}$ alkyl-N ($R^a R^b$), —N($R^a$)C(=O)$R^b$, —N($R^a$)CO$_2 R^b$, —N($R^a$) SO$_2 R^b$, or -G-$C_{1-4}$ alkyl-C(=O)N($R^a R^b$) wherein G is O or S or N(SO$_2 R^a$),
(3) —SO$_2$N($R^a R^b$), or
(4) —$C_{1-6}$ alkyl-$R^m$;

and all other variables are as originally defined;

or a pharmaceutically acceptable salt thereof.

A sixteenth embodiment of the present invention is a compound of Formula (I), wherein each of $R^4$ and $R^5$ is independently:
(1) —H,
(2) —$C_{1-4}$ alkyl, optionally substituted with one substituent which is —CN, —N($R^a R^b$), —C(=O)N($R^a R^b$), —C(=O)$R^a$, —CO$_2 R^a$, —S(O)$_n R^a$, —SO$_2$N($R^a R^b$), or —N($R^a$)SO$_2 R^b$, or
(3) —$C_{1-4}$ alkyl-$R^m$;

and all other variables are as originally defined;

or a pharmaceutically acceptable salt thereof.

A seventeenth embodiment of the present invention is a compound of Formula (I), wherein each of $R^4$ and $R^5$ is independently:
(1) —H,
(2) —$C_{1-4}$ alkyl,
(3) —(CH$_2$)$_{1-3}$—N(—$C_{1-4}$ alkyl)$_2$,
(4) —(CH$_2$)$_{1-3}$—C(=O)N(—$C_{1-4}$ alkyl)$_2$,
(5) —(CH$_2$)$_{1-3}$—CO$_2$—$C_{1-4}$ alkyl,
(6) —(CH$_2$)$_{1-3}$—S(O)$_n$—$C_{1-4}$ alkyl,
(7) —(CH$_2$)$_{1-3}$—SO$_2$N(—$C_{1-4}$ alkyl)$_2$,
(8) —(CH$_2$)$_{1-3}$—N(—$C_{1-4}$ alkyl)-SO$_2$—$C_{1-4}$ alkyl, or
(9) —(CH$_2$)$_{1-3}$—$R^m$;

and all other variables are as originally defined;

or a pharmaceutically acceptable salt thereof.

An eighteenth embodiment of the present invention is a compound of Formula (I), wherein $R^4$ and $R^5$ are both —H;

and all other variables are as originally defined;

or a pharmaceutically acceptable salt thereof.

A nineteenth embodiment of the present invention is a compound of Formula (I), wherein each $R^m$ is independently:
(i) —$C_{3-8}$ cycloalkyl,
(ii) aryl selected from phenyl and naphthyl, wherein the aryl is optionally substituted with from 1 to 3 substituents each of which is independently halogen, —$C_{1-4}$ alkyl, —$C_{1-4}$ haloalkyl, —O—$C_{1-4}$ alkyl, —O—$C_{1-4}$ haloalkyl, —CN, —N($R^a R^b$), —C(=O)N($R^a R^b$), —C(=O)$R^a$, —CO$_2 R^a$, —S(O)$_n R^a$, —SO$_2$N($R^a R^b$), —N($R^a$)C(=O)$R^b$, —N($R^a$)CO$_2 R^b$, —N($R^a$)SO$_2 R^b$, —(CH$_2$)$_{1-2}$—O—$C_{1-4}$ alkyl, —(CH$_2$)$_{1-2}$—O—$C_{1-4}$ haloalkyl, —(CH$_2$)$_{1-2}$—CN, —(CH$_2$)$_{1-2}$—N($R^a R^b$), —(CH$_2$)$_{1-2}$—C(=O)N($R^a R^b$), —(CH$_2$)$_{1-2}$—C(=O) $R^a$, —(CH$_2$)$_{1-2}$—CO$_2 R^a$, —(CH$_2$)$_{1-2}$—S(O)$_n R^a$, —(CH$_2$)$_{1-2}$—SO$_2$N($R^a R^b$), —(CH$_2$)$_{1-2}$—N($R^a$)C (=O)$R^b$, —(CH$_2$)$_{1-2}$—N($R^a$)CO$_2 R^b$, —(CH$_2$)$_{1-2}$—N ($R^a$)SO$_2 R^b$, phenyl, —(CH$_2$)$_{1-2}$-phenyl, HetB, or —(CH$_2$)$_{1-2}$HetB;
(iii) a 4- to 7-membered saturated heterocyclic ring containing from 1 to 4 heteratoms selected from N, O and S, wherein the saturated heterocyclic ring is optionally substituted with from 1 to 3 substituents each of which is independently halogen, —$C_{1-4}$ alkyl, oxo, phenyl, —(CH$_2$)$_{1-2}$-phenyl, HetC, or —(CH$_2$)$_{1-2}$HetC, or
(iv) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, —O—$C_{1-4}$ alkyl, phenyl, —(CH$_2$)$_{1-2}$-phenyl, HetC, or —(CH$_2$)$_{1-2}$-HetC;

and all other variables are as originally defined;

or a pharmaceutically acceptable salt thereof.

In an aspect of the nineteenth embodiment, $R^4$ and $R^5$ are each as defined in the fifteenth embodiment. In another aspect of the nineteenth embodiment, $R^4$ and $R^5$ are each as defined in the sixteenth embodiment. In still another aspect of the nineteenth embodiment, $R^4$ and $R^5$ are each as defined in the seventeenth embodiment.

A twentieth embodiment of the present invention is a compound of Formula (I), wherein each $R^m$ is independently:
(i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;

and all other variables are as originally defined;

or a pharmaceutically acceptable salt thereof.

In an aspect of the twentieth embodiment, $R^4$ and $R^5$ are each as defined in the fifteenth embodiment. In another aspect of the twentieth embodiment, $R^4$ and $R^5$ are each as defined in the sixteenth embodiment. In still another aspect of the twentieth embodiment, $R^4$ and $R^5$ are each as defined in the seventeenth embodiment.

A twenty-first embodiment of the present invention is a compound of Formula (I), wherein $R^m$ is:
(i) phenyl which is optionally substituted with from 1 to 3 substituents each of which is independently fluoro, chloro, bromo, —$C_{1-4}$ alkyl, —CF$_3$, —O—$C_{1-4}$ alkyl, or —OCF$_3$;
(ii) a saturated heterocyclic ring selected from the group consisting of piperidinyl, piperazinyl, pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl, thiazinanyl, thiadiazinanyl, and dioxanyl; wherein the saturated heterocyclic ring is optionally substituted with from 1 to 3 substituents each of which is independently —$C_{1-4}$ alkyl or oxo; or (iii) a heteroaromatic ring selected from the group consisting of pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl; wherein the heteroaromatic ring is optionally substituted with from 1 to 3 substituents each of which is independently halogen, —$C_{1-4}$ alkyl, or —O—$C_{1-4}$ alkyl;

and all other variables are as originally defined;

or a pharmaceutically acceptable salt thereof.

In an aspect of the twenty-first embodiment, $R^4$ and $R^5$ are each as defined in the fifteenth embodiment. In another aspect of the twenty-first embodiment, $R^4$ and $R^5$ are each as defined in the sixteenth embodiment. In still another aspect of the twenty-first embodiment, $R^4$ and $R^5$ are each as defined in the seventeenth embodiment.

A twenty-second embodiment of the present invention is a compound of Formula (I), wherein each $R^a$ and $R^b$ is independently —H or —$C_{1-6}$ alkyl;

and all other variables are as originally defined;

or a pharmaceutically acceptable salt thereof.

In an aspect of the twenty-second embodiment, each $R^a$ and $R^b$ is independently —H, methyl, or ethyl. In another aspect of the twenty-second embodiment, each $R^a$ and $R^b$ is independently —H or methyl. In still another aspect of the twenty-second embodiment, each $R^a$ and $R^b$ is methyl.

A twenty-third embodiment of the present invention is a compound of Formula (I), wherein each $R^a$ and $R^b$ is independently —H, —$C_{1-4}$ alkyl, or —$C_{3-6}$ cycloalkyl;

and all other variables are as originally defined;

or a pharmaceutically acceptable salt thereof.

In an aspect of the twenty-third embodiment, each $R^a$ and $R^b$ is independently —H, methyl, ethyl, or cyclopropyl. In another aspect of the twenty-third embodiment, each $R^a$ and $R^b$ is independently —H, methyl, or cyclopropyl.

A twenty-fourth embodiment of the present invention is a compound of Formula (I), wherein L is
(i) a single bond,
(ii) —$(CH_2)_{1-4}$—, which is optionally substituted with —C(=O)N($R^aR^b$),
(iii) —$(CH_2)_{0-3}$—C=C—$(CH_2)_{1-3}$—,
(iv) —$(CH_2)_{0-3}$—C≡C—$(CH_2)_{1-3}$—, or
(v) —$(CH_2)_{0-4}$—($C_{3-6}$ cycloalkyl)-$(CH_2)_{0-4}$—;

and all other variables are as originally defined;

or a pharmaceutically acceptable salt thereof.

A twenty-fifth embodiment of the present invention is a compound of Formula (I), wherein L is
(i) a single bond,
(ii) —$(CH_2)_{1-2}$—, which is optionally substituted with —C(=O)N($R^aR^b$),
(iii) —$(CH_2)_{0-2}$—C=C—$CH_2$—,
(iv) —$(CH_2)_{0-3}$—C≡C—$CH_2$—, or
(v) —$(CH_2)_{0-2}$—($C_{3-6}$ cycloalkyl)-$(CH_2)_{0-2}$—;

and all other variables are as originally defined;

or a pharmaceutically acceptable salt thereof.

A twenty-sixth embodiment of the present invention is a compound of Formula (I), wherein L is $CH_2$; and all other variables are as originally defined;

or a pharmaceutically acceptable salt thereof.

A first class of compounds of the present invention includes any compound of Formula (II):

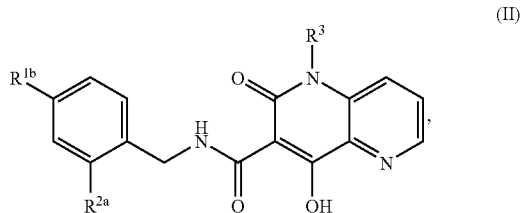

(II)

wherein:
$R^{1b}$ is —H, fluoro, chloro, bromo, —$C_{1-4}$ alkyl, or —$CF_3$;
$R^{2a}$ is:
(1) —H,
(2) —$C_{1-4}$ alkyl,
(3) —$CF_3$,
(4) fluoro, chloro, or bromo,
(5) —$SO_2$—$C_{1-4}$ alkyl,
(6) —S—$C_{1-4}$ alkyl,
(7) —$SO_2N(R^aR^b)$,
(8) —$N(R^a)SO_2$—$C_{1-4}$ alkyl, or
(9) —C(=O)N($R^aR^b$);
$R^3$ is:
(1) —H,
(2) —$C_{1-4}$ alkyl, optionally substituted with one substituent which is —O—$C_{1-4}$ alkyl, —CN, —N($R^aR^b$), —C(=O)N($R^aR^b$), —OC(=O)N($R^aR^b$), —N($R^a$)C(=O)N($R^aR^b$), —N($R^a$)C(=O)$CH_2$N($R^aR^b$), —N($R^a$)C(=O)—C(=O)N($R^aR^b$), —C(=O)$R^a$, —$CO_2R^a$, —S(O)$_nR^a$, —$SO_2N(R^aR^b)$, —N($R^a$)$CO_2R^b$, —N($R^a$)—$SO_2N(R^aR^b)$, —N($R^a$)—$SO_2CH_2$N($R^aR^b$), or —N($R^a$)$SO_2R^b$,
with the proviso that none of the following substituents is attached to the carbon in the —$C_{1-4}$ alkyl group that is attached to the ring nitrogen: —O—$C_{1-4}$ alkyl, —N($R^aR^b$), —OC(=O)N($R^aR^b$), —N($R^a$)C(=O)N($R^aR^b$), —N($R^a$)—C(=O)—$CH_2$N($R^aR^b$), —N($R^a$)C(=O)—C(=O)N($R^aR^b$), —N($R^a$)$CO_2R^b$, —N($R^a$)—$SO_2N(R^aR^b)$, —N($R^a$)—$SO_2$—$CH_2$N($R^aR^b$), or —N($R^a$)$SO_2R^b$,
(3) —$C_{1-4}$ alkyl-$R^k$,
(4) —$C_{1-4}$ alkyl-C(=O)—$R^k$, or
5) —$C_{2-4}$ alkyl-N($R^a$)—C(=O)—$R^k$, with the proviso that the substituent is not attached to the carbon in the —$C_{2-4}$ alkyl group that is attached to the ring nitrogen;
wherein $R^k$ is:
(i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(ii) a 5- or 6-membered saturated heterocyclic ring containing from 1 to 4 heteroatoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;

each $R^a$ and $R^b$ is independently —H or —$C_{1-4}$ alkyl; and n is an integer equal to zero, 1 or 2;

or a pharmaceutically acceptable salt thereof.

A second class of compounds of the present invention includes any compound of Formula (II), wherein:
$R^{1b}$ is fluoro, chloro, bromo, methyl, or ethyl;
$R^{2a}$ is:
  (1) —H,
  (2) methyl or ethyl,
  (3) fluoro,
  (4) —$SO_2$—$C_{1-4}$ alkyl,
  (5) —S—$C_{1-4}$ alkyl,
  (6) —$SO_2N$(—$C_{1-4}$ alkyl)$_2$,
  (7) —$NHSO_2$—$C_{1-4}$ alkyl,
  (8) —N(—$C_{1-4}$ alkyl)$SO_2$—$C_{1-4}$ alkyl, or
  (9) —C(=O)NH(—$C_{1-4}$ alkyl);
$R^3$ is:
  (1) —H,
  (2) —$C_{1-4}$ alkyl,
  (3) —$(CH_2)_{2-3}$—O—$C_{1-4}$ alkyl,
  (4) —$(CH_2)_{2-3}$—N(—$C_{1-4}$ alkyl)$_2$,
  (5) —$(CH_2)_{1-3}$—C(=O)N(—$C_{1-4}$ alkyl)$_2$,
  (6) —$(CH_2)_{2-3}$—N(—$C_{1-4}$ alkyl)C(=O)N(—$C_{1-4}$ alkyl)$_2$,
  (7) —$(CH_2)_{2-3}$—N(—$C_{1-4}$ alkyl)C(=O)—C(=O)N(—$C_{1-4}$ alkyl)$_2$,
  (8) —$(CH_2)_{1-3}$—$CO_2$—$C_{1-4}$ alkyl,
  (9) —$(CH_2)_{1-3}$—$S(O)_n$—$C_{1-4}$ alkyl,
  (10) —$(CH_2)_{1-3}$—$SO_2N$(—$C_{1-4}$ alkyl)$_2$,
  (11) —$(CH_2)_{2-3}$—N(—$C_{1-4}$ alkyl)-$SO_2N$(—$C_{1-4}$ alkyl)$_2$,
  (12) —$(CH_2)_{2-3}$—N(—$C_{1-4}$ alkyl)-$SO_2$—$C_{1-4}$ alkyl,
  (13) —$(CH_2)_{1-3}$—$R^k$,
  (14) —$(CH_2)_{1-3}$—C(=O)—$R^k$, or
  (15) —$(CH_2)_{2-3}$—$N(R^a)$—C(=O)—$R^k$;
  wherein $R^k$ is:
    (i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
    (ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
    (iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl; and
n is an integer equal to zero, 1 or 2;

or a pharmaceutically acceptable salt thereof.

A third class of compounds of the present invention includes any compound of Formula (II) as defined in the second class, or a pharmaceutically acceptable salt thereof, except that $R^{2a}$ is not —C(=O)NH(—$C_{1-4}$ alkyl).

A fourth class of compounds of the present invention includes compounds of Formula (II), wherein:
$R^{1b}$ is fluoro;
$R^{2a}$ is:
  (1) —H,
  (2) fluoro,
  (3) —$SO_2$—$C_{1-4}$ alkyl,
  (4) —S—$C_{1-4}$ alkyl,
  (5) —$SO_2N$(—$C_{1-4}$ alkyl)$_2$,
  (6) —$NHSO_2$—$C_{1-4}$ alkyl,
  (7) —N(—$C_{1-4}$ alkyl)$SO_2$—$C_{1-4}$ alkyl, or
  (8) —C(=O)NH(—$C_{1-4}$ alkyl);
$R^3$ is:
  (1) —H,
  (2) —$C_{1-4}$ alkyl,
  (3) —$(CH_2)_{2-3}$—O—$C_{1-4}$ alkyl,
  (4) —$(CH_2)_{2-3}$—N(—$C_{1-2}$ alkyl)$_2$,
  (5) —$(CH_2)_{1-3}$—C(=O)N(—$C_{1-2}$ alkyl)$_2$,
  (6) —$(CH_2)_{2-3}$—N(—$C_{1-2}$ alkyl)C(=O)N(—$C_{1-2}$ alkyl)$_2$,
  (7) —$(CH_2)_{2-3}$—N(—$C_{1-2}$ alkyl)C(=O)—C(=O)N(—$C_{1-2}$ alkyl)$_2$,
  (8) —$(CH_2)_{1-3}$—$S(O)_n$—$C_{1-2}$ alkyl,
  (9) —$(CH_2)_{1-3}$—$SO_2N$(—$C_{1-2}$ alkyl)$_2$,
  (10) —$(CH_2)_{2-3}$—N(—$C_{1-2}$ alkyl)-$SO_2N$(—$C_{1-2}$ alkyl)$_2$,
  (11) —$(CH_2)_{2-3}$—N(—$C_{1-2}$ alkyl)-$SO_2$—$C_{1-2}$ alkyl,
  (12) —$(CH_2)_{1-3}$—$R^k$, or
  (13) —$(CH_2)_{1-3}$—C(=O)—$R^k$;
  wherein $R^k$ is:
    (i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
    (ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
    (iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl; and
n is an integer equal to zero, 1 or 2;

or a pharmaceutically acceptable salt thereof.

A fifth class of compounds of the present invention includes any compound of Formula (II) as defined in the fourth class, or a pharmaceutically acceptable salt thereof, except that $R^{2a}$ is not —C(=O)NH(—$C_{1-4}$ alkyl).

In a feature of each of the preceding classes, $R^k$ is:
  (i) phenyl which is optionally substituted with from 1 to 3 substituents each of which is independently fluoro, chloro, bromo, —$C_{1-4}$ alkyl, —$CF_3$, —O—$C_{1-4}$ alkyl, or —$OCF_3$;
  (ii) a saturated heterocyclic ring selected from the group consisting of piperidinyl, piperazinyl, pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl, thiazinanyl, thiadiazinanyl, and dioxanyl; wherein the saturated heterocyclic ring is optionally substituted with from 1 to 3 substituents each of which is independently —$C_{1-4}$ alkyl or oxo; or
  (iii) a heteroaromatic ring selected from the group consisting of pyridyl, pyrrolyl, pyrazinyl,-pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl; wherein the heteroaromatic ring is optionally substituted with from 1 to 3 substituents each of which is independently halogen, —$C_{1-4}$ alkyl, or —O—$C_{1-4}$ alkyl.

It is to be understood that additional embodiments of the present invention include, but are not limited to, compounds of Formula I wherein each of two or three or more of L, $R^{1a}$, $R^{1b}$, $R^{1c}$, $R^{2a}$, $R^{2b}$, $R^3$, $R^4$, $R^5$, $R^6$, $R^a$, $R^b$, $R^k$ and $R^m$ is independently defined in accordance with its definition in one of the embodiments or an aspect thereof as set forth above, or in accordance with its definition in one of the foregoing classes set forth above or a sub-class or feature thereof. Any and all possible combinations of these variables in Formula I are additional embodiments within the scope of the present invention.

An aspect of the present invention is a compound selected from the group consisting of N-(4-fluorobenzyl)-hydroxy-2-oxo-1,2-dihydro-1,5-naphthyridine-3-carboxamide;

1-{2-[(dimethylamino)sulfonyl]ethyl}-N-(4-fluorobenzyl)-4-hydroxy-2-oxo-1,2-dihydro-1,5-naphthyridine-3-carboxamide;

1-{2-[(dimethylamino)sulfonyl]ethyl}-N-[4-fluoro-2-(methylsulfonyl)benzyl]-4-hydroxy-2-oxo-1,2-dihydro-1,5-naphthyridine-3-carboxamide;

1-(1,4-dioxan-2-ylmethyl)-N-(4-fluorobenzyl)-4-hydroxy-2-oxo-1,2-dihydro-1,5-naphthyridine-3-carboxamide;

1-(1,4-dioxan-2-ylmethyl)-N-[4-fluoro-2-(methylthio)benzyl]-4-hydroxy-2-oxo-1,2-dihydro-1,5-naphthyridine-3-carboxamide;

1-(1,4-dioxan-2-ylmethyl)-N-[4-fluoro-2-(methylsulfonyl)benzyl]-4-hydroxy-2-oxo-1,2-dihydro-1,5-naphthylidine-3-carboxamide;

N-(4-fluorobenzyl)-4-hydroxy-1-{2-[methyl(methylsulfonyl)amino]ethyl}-2-oxo-1,2-dihydro-1,5-naphthyridine-3-carboxamide;

N-[4-fluoro-2-(methylsulfonyl)benzyl]-4-hydroxy-1-1-{2-[methyl(methylsulfonyl)amino]ethyl}-2-oxo-1,2-dihydro-1,5-naphthyridine-3-carboxamide;

1-[(1,1-Dioxidotetrahydrothien-3-yl)methyl]-N-(4-fluorobenzyl)-4-hydroxy-2-oxo-1,2-dihydro-1,5-naphthyridine-3-carboxamide;

N-[4-fluoro-2-(methylsulfonyl)benzyl]-4-hydroxy-1-[2-(methylsulfonyl)ethyl]-2-oxo-1,2-dihydro-1,5-naphthyridine-3-carboxamide;

1-ethyl-N-[4-fluoro-2-(methylthio)benzyl]-4-hydroxy-2-oxo-1,2-dihydro-1,5-naphthyridine-3-carboxamide;

1-ethyl-N-[4-fluoro-2-(methylsulfonyl)benzyl]-4-hydroxy-2-oxo-1,2-dihydro-1,5-naphthyridine-3-carboxamide;

N-[4-fluoro-2-(methylsulfonyl)benzyl]-4-hydroxy-1-methyl-2-oxo-1,2-dihydro-1,5-naphthyridine-3-carboxamide;

N-(4-fluorobenzyl)-4-hydroxy-1-[2-(methylsulfinyl)ethyl]-2-oxo-1,2-dihydro-1,5-naphthyridine-3-carboxamiide;

N-(4-fluorobenzyl)-4-hydroxy-1-[2-(methylsulfonyl)ethyl]-2-oxo-1,2-dihydro-1,5-naphthyridine-3-carboxamide;

N-(4-fluorobenzyl)-4-hydroxy-1-(2-morpholin-4-ylethyl)-2-oxo-1,2-dihydro-1,5-naphthyridine-3-carboxamide;

N-(4-fluorobenzyl)-4-hydroxy-2-oxo-1-[2-(1H-1,2,4-triazol-1-yl)ethyl]-1,2-dihydro-1,5-naphthyridine-3-carboxamide;

1-[2-(dimethylamino)-2-oxoethyl]-N-[4-fluoro-2-(methylsulfonyl)benzyl]-4-hydroxy-2-oxo-1,2-dihydro-1,5-naphthyridine-3-carboxamide;

N-[4-fluoro-2-(methylsulfonyl)benzyl]-4-hydroxy-2-oxo-1,2-dihydro-1,5-naphthyridine-3-carboxamide;

N-[4-fluoro-2-(methylsulfonyl)benzyl]-4-hydroxy-1-(2-methoxyethyl)-2-oxo-1,2-dihydro-1,5-naphthyridine-3-carboxamide;

1-benzyl-n-[4-fluoro-2-(methylsulfonyl)benzyl]-4-hydroxy-2-oxo-1,2-dihydro-1,5-naphthyridine-3-carboxamide;

1-{2-[[(dimethylamino)sulfonyl](methyl)amino]ethyl}-N-[4-fluoro-2-(methylsulfonyl)benzyl]4-hydroxy-2-oxo-1,2-dihydro-1,5-naphthylidine-3-carboxamide;

N-[4-fluoro-2-(methylsulfonyl)benzyl]-4-hydroxy-1-[2-(4-methylpiperazin-1-yl)-2-oxoethyl]-2-oxo-1,2-dihydro-1,5-naphthyridine-3-carboxamide;

N-[4-fluoro-2-(methylsulfonyl)benzyl]-4-hydroxy-1-(2-morpholin-4-yl-2-oxoethyl)-2-oxo-1,2-dihydro-1,5-naphthyridine-3-carboxamide;

N-[4-fluoro-2-(methylsulfonyl)benzyl]-1-{2-[[(dimethylamino)carbonyl](methyl)amino]ethyl}-4-hydroxy-2-oxo-1,2-dihydro-1,5-naphthyridine-3-carboxamide;

1-benzyl-N-{4-fluoro-2-[(methylamino)carbonyl]benzyl}-4-hydroxy-2-oxo-1,2-dihydro-1,5-naphthyridine-3-carboxamide;

N-[4-fluoro-2-(methylsulfonyl)benzyl]-4-hydroxy-2-oxo-1-(2-oxo-2-thiomorpholin-4-ylethyl)-1,2-dihydro-1,5-naphthyridine-3-carboxamide;

and pharmaceutically acceptable salts thereof.

Other embodiments of the present invention include the following:

(a) A pharmaceutical composition comprising a therapeutically effective amount of a compound of Formula (I) and a pharmaceutically acceptable carrier.

(b) A pharmaceutical composition which comprises the product prepared by combining (e.g., mixing) a therapeutically effective amount of a compound of Formula (I) and a pharmaceutically acceptable carrier.

(c) The pharmaceutical composition of (a) or (b), further comprising a therapeutically effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A combination useful for inhibiting HIV integrase, for treating or preventing infection by HIV, or for preventing, treating or delaying the onset of AIDS, which is a therapeutically effective amount of a compound of Formula (I) and a therapeutically effective amount of an HIV infection/AIDS treatment agent selected from the group consisting of HIV/AIDS antiviral agents, immunomodulators, and anti-infective agents.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject a therapeutically effective amount of a compound of Formula (I).

(h) A method of preventing or treating infection by HIV in a subject in need thereof which comprises administering to the subject a therapeutically effective amount of a compound of Formula (I).

(i) The method of (h), wherein the compound of Formula (I) is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors.

(j) A method of preventing, treating or delaying the onset of AIDS in a subject in need thereof which comprises administering to the subject a therapeutically effective amount of a compound of Formula (I).

(k) The method of (j), wherein the compound is administered in combination with a therapeutically effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "$C_{1-6}$ alkyl" (or "$C_1$-$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "—$C_{1-6}$ alkyl-" refers to a $C_1$ to $C_6$ linear or branched alkyl group as just defined which is bivalent. It can alternatively be referred to as "$C_{1-6}$ alkylene" or "$C_{1-6}$ alkanediyl". A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—.

The term "$C_0$" as employed in expressions such as "$C_{0-6}$ alkyl" means a direct covalent bond. For example, when L in Compound I is —($C_{0-3}$ alkyl)-C≡C—($C_{1-3}$ alkyl)-, then L is —C≡C—($C_{1-3}$ alkyl)-, when the first alkyl group is "$C_0$". As a further, more specific example, when L is —($C_{0-3}$ alkyl)-C≡C—($C_{1-3}$ alkyl)-, wherein the first alkyl group is "$C_0$" and the second alkyl group is "$C_1$", then the compound is a compound of Formula (III):

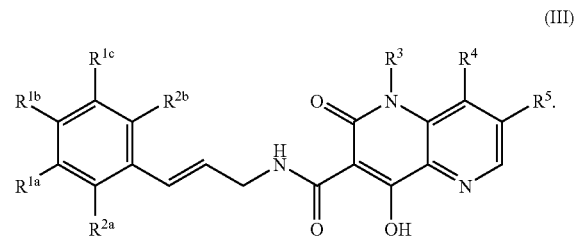

The term "$C_{2-6}$ alkenyl" (or "$C_2$-$C_6$ alkenyl") means linear or branched chain alkenyl groups having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-4}$ alkenyl" have an analogous meaning.

The term "$C_{2-5}$ alkynyl" (or "$C_2$-$C_5$ alkynyl") means linear or branched chain alkynyl groups having from 2 to 5 carbon atoms and includes all of the pentynyl isomers as well as 1-butynyl, 2-butynyl, 3-butynyl, 1-propynyl, 2-propynyl, and ethynyl (or acetylenyl). Similar terms such as "$C_{2-4}$ alkynyl" have an analogous meaning.

The term "$C_{3-8}$ cycloalkyl" (or "$C_{3-C8}$ cycloalkyl") means a cyclic ring of an alkane having three to eight total carbon atoms (i.e., cyclopropyl, cyclobutyl, cyclopentyl, cyclohexyl, cycloheptyl, or cyclooctyl). Similar terms such as "$C_{3-6}$ cycloalkyl" have an analogous meaning.

The term "halogen" (or "halo") refers to fluorine, chlorine, bromine and iodine (alternatively referred to as fluoro, chloro, bromo, and iodo).

The term "$C_{1-6}$ haloalkyl" (which may alternatively be referred to as "$C_1$-$C_6$ haloalkyl" or "halogenated $C_1$-$C_6$ alkyl") means a $C_1$ to $C_6$ linear or branched alkyl group as defined above with one or more halogen substituents. The term "$C_{1-4}$ haloalkyl" has an analogous meaning. The term "$C_{1-6}$ fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "carbocycle" (and variations thereof such as "carbocyclic" or "carbocyclyl") as used herein refers to (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of or fused to the other ring or rings and each ring is saturated or unsaturated. The carbocycle may be attached to the rest of the molecule at any carbon atom which results in a stable compound. When the carbocyclic ring has substituents, it is understood that the substituents may be attached to any atom in the ring which results in a stable chemical structure.

The fused bicyclic carbocycles are a subset of the carbocycles; i.e., the term "fused bicyclic carbocycle" generally refers to a $C_7$ to $C_{12}$ bicyclic ring system in which each ring is saturated or unsaturated and two adjacent carbon atoms are shared by each of the rings in the ring system. Fused tricyclic carbocycles have an analogous meaning. A subset of the fused bicyclic carbocycles are those bicyclic carbocycles in which one ring is a benzene ring and the other ring is saturated or unsaturated, with attachment via any carbon atom that results in a stable compound. Representative examples of this subset include the following:

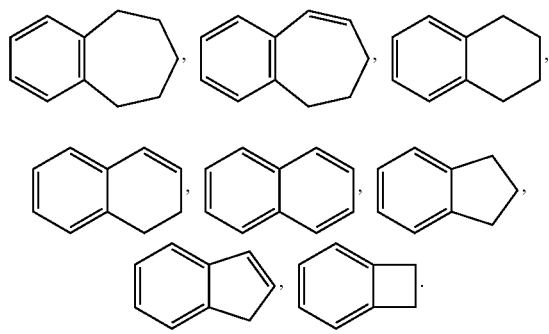

Aryl groups form a subset of the carbocycles; i.e., the term "aryl" as used herein refers to an aromatic carbocyclic ring or an aromatic carbocyclic fused ring system. The fused ring system contains two or more carbocyclic rings in which each ring shares two adjacent carbon atoms with at least one other ring. The aryl group may be attached to the rest of the molecule at any carbon atom which results in a stable compound.

A subset of aryl groups particularly suitable for use in the present invention (e.g., in the definition of $R^{2a}$ or $R^{2b}$, when $R^{2a}$ or $R^{2b}$ is —$C_{1-6}$ alkyl substituted with aryl) includes those selected from phenyl, naphthyl, anthryl, and phenanthryl. Another particularly suitable subset of aryl groups is phenyl and naphthyl. Still another particularly suitable subset of aryl groups is phenyl per se.

A subset of carbocycles particularly suitable for use in the present invention (e.g., in the definition of $R^k$ or $R^m$) includes any carbocycle which is (i) —$C_{3-8}$ cycloalkyl or (ii) aryl. Another particularly suitable subset includes any carbocycle which is —$C_{3-8}$ cycloalkyl, phenyl, naphthyl, anthryl, or phenanthryl. Still another particularly suitable subset includes any carbocycle which is —$C_{3-8}$ cycloalkyl, phenyl, or naphthyl. Yet another particularly suitable subset is phenyl and naphthyl, and still another is phenyl per se.

The term "heterocycle" (and variations thereof such as "heterocyclic" or "heterocyclyl") refers to (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated, and the monocyclic ring, bicyclic ring system, or tricyclic ring system contains one or more heteroatoms (e.g., from 1 to 6 heteroatoms, from 1 to 5 heteroatoms, or from 1 to 4 heteroatoms) independently selected from N, O and S and a balance of carbon atoms (the monocylic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. The heterocyclic ring may be attached to the rest of the molecule via any heteroatom or carbon atom in the ring, provided that attachment results in the creation of a stable structure. When the heterocyclic ring has substituents, it is understood that the substituents may be attached to any atom in the ring, whether a heteroatom or a carbon atom, provided that a stable chemical structure results.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 7-membered saturated monocyclic ring which consists of carbon atoms and one or more heteroatoms independently selected from N, O and S. Representative examples include piperidinyl, piperazinyl, azepanyl (i.e., 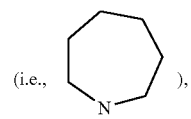), pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl (or tetrahydrofuranly), thiazinanyl (e.g., 1,2-thiazinanyl 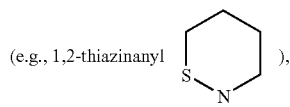), thiadiazinanyl (e.g., 1,2,6-thiadiazinanyl 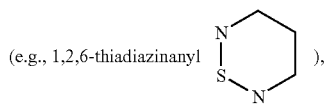), and dioxanyl.

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring which consists of carbon atoms and one or more (e.g., from 1 to 4) heteroatoms independently selected from N, O and S. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e., 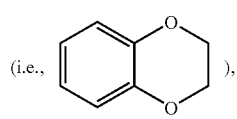), and benzo-1,3-dioxolyl

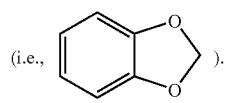

Representative examples of tricyclic heterocycles include phenothiazinyl, carbazolyl, beta-carbolinyl, tetrahydro-beta-carbolinyl, acridinyl, phenazinyl, and phenoxazinyl.

A subset of heterocycles particularly suitable for use in the present invention (e.g., in the definition of $R^k$ or $R^m$) includes any heterocycle which is (i) a 4- to 7-membered saturated heterocyclic ring containing from 1 to 4 heteratoms selected from N, O and S, or (ii) a 5- or 6-membered heteroaromatic ring containing from 1 to 4 heteroatoms independently selected from N, O and S. Another particularly suitable subset includes any heterocycle which is (i) a 5 or 6-membered saturated heterocyclic ring containing from 1 to 4 heteratoms independently selected from N, O and S, or (ii) a 5- or 6-membered heteroaromatic ring containing from 1 to 4 heteroatoms independently selected from N, O and S. Still another particularly suitable subset includes any heterocycle which is (i) a 5 or 6-membered saturated heterocyclic ring containing from 1 to 3 heteratoms independently selected from N, O and S, or (ii) a 5- or 6-membered heteroaromatic ring containing from 1 to 4 heteroatoms independently selected from N, O and S. Still another particularly suitable subset includes any heterocycle which is (i) a 5 or 6-membered saturated heterocyclic ring containing from 1 or 2 heteratoms independently selected from N, O and S, or (ii) a 5- or 6-membered heteroaromatic ring containing from 1 to 4 N atoms.

A subset of heteroaryl groups particularly suitable for use in the present invention (e.g., in the definition of $R^{2a}$ or $R^{2b}$, when $R^{2a}$ or $R^{2b}$ is —$C_{1-6}$ alkyl substituted with heteroaryl) includes any heteroaryl which is a 5- or 6-membered heteraromatic ring containing from 1 to 4 heteroatoms or a 9- or 10-membered bicyclic heteroaromatic ring system containing from 1 to 6 heteroatoms, wherein the heteroatoms in the heteroaryl are independently selected from N, O and S. Another particularly suitable subset of aryl groups includes any heteroaryl which is a 5- or 6-membered heteraromatic ring containing from 1 to 4 heteroatoms. Still another particularly suitable subset of heteroaryl groups includes any heteroaryl which is pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, or thiadiazolyl.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable (e.g., $R^a$, $R^b$, or $R^m$) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The compounds of the present invention may have asymmetric centers and may occur, except when specifically noted, as mixtures of stereoisomers or as individual diastereomers, or enantiomers, with all isomeric forms being included in the present invention.

Compounds of Formula I wherein $R^3$=H may also occur as tautomers thereof. Tautomers include, but are not limited to:

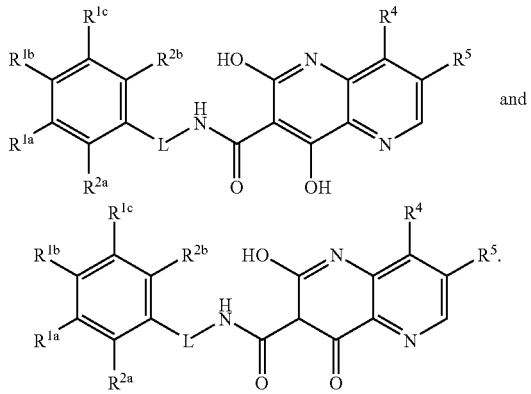

It is understood that the present invention includes all tautomers of the hydroxynaphthyridinone compounds embraced by Formula I, both singly and in mixtures.

The compounds of the present invention are useful in the inhibition of HIV integrase, the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. When the compounds of the invention carry an acidic moiety, suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

For the purpose of preventing or treating HIV infection or preventing, treating or delaying the onset of AIDS, the compounds of the present invention can be administered orally, parenterally (including subcutaneous injections, intravenous, intramuscular, intrasternal injection or infusion techniques), by inhalation spray, or rectally, in the form of a unit dosage of a pharmaceutical composition containing a therapeutically effective amount of the compound and conventional non-toxic pharmaceutically-acceptable carriers, adjuvants and vehicles.

The term "administration" and variants thereof (e.g., "administering" a compound) in reference to a compound of the invention mean providing the compound to the individual in need of treatment. When a compound of the invention is provided in combination with one or more other active agents (e.g., antiviral agents useful for treating HIV infection or AIDS), "administration" and its variants are each understood to include concurrent and sequential provision of the compound and other agents.

As used herein, the term "composition" is intended to encompass a product comprising the specified ingredients in the specified amounts, as well as any product which results, directly or indirectly, from combining the specified ingredients in the specified amounts.

By "pharmaceutically acceptable" is meant that the ingredients of the pharmaceutical composition must be compatible with each other and not deleterious to the recipient thereof.

The term "subject" (which may be alternatively referred to herein as "patient") as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated. When the active compound (i.e., active ingredient) is administered as the salt, references to the amount of active ingredient are to the free acid or free base form of the compound.

The pharmaceutical compositions can be in the form of orally-administrable suspensions or tablets or capsules, nasal sprays, sterile injectable preparations, for example, as sterile injectable aqueous or oleagenous suspensions or suppositories. These compositions can be prepared by methods and contain excipients which are well known in the art. Suitable methods and ingredients are described in *Remington's Pharmaceutical Sciences*, 18$^{th}$ edition, edited by A. R. Gennaro, Mack Publishing Co., 1990, which is herein incorporated by reference in its entirety.

The compounds of this invention can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more of the HIV/AIDS antivirals, immunomodulators, antiinfectives, or vaccines useful for treating HIV infection or AIDS. Suitable agents include those listed in the following Table:

Antivirals

| Drug Name | Manufacturer (Tradename and/or Location) | Indication (Activity) |
|---|---|---|
| abacavir GW 1592 1592U89 | Glaxo Welcome (ZIAGEN ®) | HIV infection, AIDS, ARC (nucleoside reverse transcriptase inhibitor) |
| abacavir + lamivudine + zidovudine | GlaxoSmithKline (TRIZIVIR ®) | HIV infection, AIDS, ARC (nucleoside reverse transcriptase inhibitors) |
| acemannan | Carrington Labs (Irving, TX) | ARC |
| ACH 126443 | Achillion Pharm. | HIV infections, AIDS, ARC (nucleoside reverse transcriptase inhibitor) |
| acyclovir | Burroughs Wellcome | HIV infection, AIDS, ARC, in combination with AZT |
| AD-439 | Tanox Biosystems | HIV infection, AIDS, ARC |

-continued

| Drug Name | Manufacturer (Tradename and/or Location) | Indication (Activity) |
|---|---|---|
| AD-519 | Tanox Biosystems | HIV infection, AIDS, ARC |
| adefovir dipivoxil GS 840 | Gilead | HIV infection, AIDS, ARC (reverse transcriptase inhibitor) |
| AL-721 | Ethigen (Los Angeles, CA) | ARC, PGL, HIV positive, AIDS |
| alpha interferon | Glaxo Wellcome | Kaposi's sarcoma, HIV, in combination w/Retrovir |
| AMD3100 | AnorMed | HIV infection, AIDS, ARC (CXCR4 antagonist) |
| amprenavir 141 W94 GW 141 VX478 (Vertex) | Glaxo Wellcome (AGENERASE ®) | HIV infection, AIDS, ARC (PI) |
| ansamycin LM 427 | Adria Laboratories (Dublin, OH) Erbamont (Stamford, CT) | ARC |
| antibody which neutralizes pH labile alpha aberrant interferon | Advanced Biotherapy Concepts (Rockville, MD) | AIDS, ARC |
| AR177 | Aronex Pharm | HIV infection, AIDS, ARC |
| atazanavir (BMS 232632) | Bristol-Myers-Squibb (ZRIVADA ®) | HIV infection, AIDS, ARC (protease inhibitor) |
| beta-fluoro-ddA | Nat'l Cancer Institute | AIDS-associated diseases |
| BMS-232623 (CGP-73547) | Bristol-Myers Squibb/ Novartis | HIV infection, AIDS, ARC (protease inhibitor) |
| BMS-234475 (CGP-61755) | Bristol-Myers Squibb/ Novartis | HIV infection, AIDS, ARC (protease inhibitor) |
| capravirine (AG-1549, S-1153) | Pfizer | HIV infection, AIDS, ARC (non-nucleoside reverse transcriptase inhibitor) |
| CI-1012 | Warner-Lambert | HIV-1 infection |
| cidofovir | Gilead Science | CMV retinitis, herpes, papillomavirus |
| curdlan sulfate | AJI Pharma USA | HIV infection |
| cytomegalovirus immune globin | MedImmune | CMV retinitis |
| cytovene ganciclovir | Syntex | sight threatening CMV peripheral CMV retinitis |
| delavirdine | Pharmacia-Upjohn (RESCRIPTOR ®) | HIV infection, AIDS, ARC (non-nucleoside reverse transcriptase inhibitor) |
| dextran Sulfate | Ueno Fine Chem. Ind. Ltd. (Osaka, Japan) | AIDS, ARC, HIV positive asymptomatic |
| ddC (zalcitabine, dideoxycytidine) | Hoffman-La Roche (HIVID ®) | HIV infection, AIDS, ARC (nuclesodie reverse transcriptase inhibitor) |
| ddI dideoxyinosine | Bristol-Myers Squibb (VIDEX ®) | HIV infection, AIDS, ARC; combination with AZT/d4T (nucleoside reverse transcriptase inhibitor) |
| DPC 681 & DPC 684 | DuPont | HIV infection, AIDS, ARC (protease inhibitors) |
| DPC 961 & DPC 083 | DuPont | HIV infection AIDS, ARC (non-nucleoside reverse transcriptase inhibitors) |
| EL10 | Elan Corp, PLC (Gainesville, GA) | HIV infection |
| efavirenz (DMP 266) | DuPont (SUSTIVA ®) Merck (STOCRIN ®) | HIV infection, AIDS, ARC (non-nucleoside RT inhibitor) |
| famciclovir | Smith Kline | herpes zoster, herpes simplex |
| emtricitabine FTC | Triangle Pharmaceuticals (COVIRACIL ®) Emory University | HIV infection, AIDS, ARC (nucleoside reverse transcriptase inhibitor) |
| emvirine | Triangle Pharmaceuticals (COACTINON ®) | HIV infection, AIDS, ARC (non-nucleoside reverse transcriptase inhibitor) |

-continued

| Drug Name | Manufacturer (Tradename and/or Location) | Indication (Activity) |
|---|---|---|
| enfuvirtide T-20 | Trimeris & Roche (FUSEON ®) | HIV infection, AIDS, ARC (fusion inhibitor) |
| HB Y097 | Hoechst Marion Roussel | HIV infection, AIDS, ARC (non-nucleoside reverse transcriptase inhibitor) |
| hypericin | VIMRx Pharm. | HIV infection, AIDS, ARC |
| recombinant human interferon beta | Triton Biosciences (Almeda, CA) | AIDS, Kaposi's sarcoma, ARC |
| interferon alfa-n3 | Interferon Sciences | ARC, AIDS |
| indinavir | Merck (CRIXIVAN ®) | HIV infection, AIDS, ARC, asymptomatic HIV positive, also in combination with AZT/ddI/ddC |
| ISIS 2922 | ISIS Pharmaceuticals | CMV retinitis |
| JE2147/AG1776 | Agouron | HIV infection, AIDS, ARC (protease inhibitor) |
| KNI-272 | Nat'l Cancer Institute | HIV-assoc. diseases |
| lamivudine, 3TC | Glaxo Wellcome (EPIVIR ®) | HIV infection, AIDS, ARC (nucleoside reverse transcriptase inhibitor); also with AZT |
| lobucavir | Bristol-Myers Squibb | CMV infection |
| lopinavir (ABT-378) | Abbott | HIV infection, AIDS, ARC (protease inhibitor) |
| lopinavir + ritonavir (ABT-378/r) | Abbott (KALETRA ®) | HIV infection, AIDS, ARC (protease inhibitor) |
| mozenavir (DMP-450) | AVID (Camden, NJ) | HIV infection, AIDS, ARC (protease inhibitor) |
| nelfinavir | Agouron (VIRACEPT ®) | HIV infection, AIDS, ARC (protease inhibitor) |
| nevirapine | Boeheringer Ingleheim (VIRAMUNE ®) | HIV infection, AIDS, ARC (non-nucleoside reverse transcriptase inhibitor) |
| novapren | Novaferon Labs, Inc. (Akron, OH) | HIV inhibitor |
| peptide T octapeptide sequence | Peninsula Labs (Belmont, CA) | AIDS |
| PRO 140 | Progenics | HIV infection, AIDS, ARC (CCR5 co-receptor inhibitor) |
| PRO 542 | Progenics | HIV infection, AIDS, ARC (attachment inhibitor) |
| trisodium phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| probucol | Vyrex | HIV infection, AIDS |
| RBC-CD4 | Sheffield Med. Tech (Houston TX) | HIV infection, AIDS, ARC |
| ritonavir (ABT-538) | Abbott (RITONAVIR ®) | HIV infection, AIDS, ARC (protease inhibitor) |
| saquinavir | Hoffmann-LaRoche (FORTOVASE ®) | HIV infection, AIDS, ARC (protease inhibitor) |
| stavudine; d4T didehydrodeoxy-thymidine | Bristol-Myers Squibb (ZERIT ®) | HIV infection, AIDS, ARC (nucleoside reverse transcriptase inhibitor) |
| T-1249 | Trimeris | HIV infection, AIDS, ARC (fusion inhibitor) |
| TAK-779 | Takeda | HIV infection, AIDS, ARC (injectable CCR5 receptor antagonist) |
| tenofovir | Gilead (VIREAD ®) | HIV infection, AIDS, ARC (nucleotide reverse transcriptase inhibitor) |
| tipranavir (PNU-140690) | Boehringer Ingelheim | HIV infection, AIDS, ARC (protease inhibitor) |
| TMC-120 & TMC-125 | Tibotec | HIV infections, AIDS, ARC (non-nucleoside reverse transcriptase inhibitors) |
| TMC-126 | Tibotec | HIV infection, AIDS, ARC (protease inhibitor) |
| valaciclovir | Glaxo Wellcome | genital HSV & CMV infections |
| virazole | Viratek/ICN (Costa | asymptomatic HIV positive, |

-continued

| Drug Name | Manufacturer (Tradename and/or Location) | Indication (Activity) |
|---|---|---|
| ribavirin | Mesa, CA) | LAS, ARC |
| zidovudine; AZT | Glaxo Wellcome (RETROVIR ®) | HIV infection, AIDS, ARC, Kaposi's sarcoma in combination with other therapies (nucleoside reverse transcriptase inhibitor) |

Immuno-Modulators

| Drug Name | Manufacturer | Indication |
|---|---|---|
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin ntravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma, AIDS, ARC, in combination w/AZT |
| SK&F106528 Soluble T4 | Smith Kline | HIV infection |
| Thymopentin | Immunobiology Research Institute | HIV infection |

-continued

| Drug Name | Manufacturer | Indication |
|---|---|---|
| Tumor Necrosis Factor; TNF | Genentech | ARC, in combination w/gamma Interferon |
| etanercept | Immunex Corp (ENBREL ®) | rheumatoid arthritis |
| infliximab | Centocor (REMICADE ®) | rheumatoid arthritis and Crohn's disease |

Anti-Infectives

| Drug Name | Manufacturer | Indication |
|---|---|---|
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidia diarrhea |
| Intraconazole-R51211 | Janssen Pharm. | histoplasmosis; cryptococcal meningitis |
| Trimetrexate | Warner-Lambert | PCP |

Other

| Drug Name | Manufacturer | Indication |
|---|---|---|
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption, related to AIDS |

It will be understood that the scope of combinations of the compounds of this invention with HIV/AIDS antivirals, immunomodulators, anti-infectives or vaccines is not limited to the list in the above Table, but includes in principle any combination with any pharmaceutical composition useful for the treatment of AIDS. The HIV/AIDS antivirals and other agents will typically be employed in these combinations in their conventional dosage ranges and regimens as reported in the art, including the dosages described in the *Physicians' Desk Reference*, 54$^{th}$ edition, Medical Economics Company, 2000, which is incorporated herein by reference in its entirety. The dosage ranges for a compound of the invention in these combinations are the same as those set forth above.

Abbreviations used in the instant specification, particularly the Schemes and Examples, include the following:
AIDS=acquired immunodeficiency syndrome
APCI=atmospheric pressure chemical ionization mass spectroscopy
ARC=AIDS related complex
BOC or Boc=t-butyloxycarbonyl
BOP=benzotriazol-1-yloxytris-(dimethylamino)phosphonium hexafluorophosphate
CBZ=carbobenzoxy (alternatively, benzyloxycarbonyl)
DIEA or DIPEA=diisopropylethylamine (or Hunig's base)
DIPEA=diisopropylethylamine=Hunig's base
DMF=dimethylformamide
DMSO=dimethyl sulfoxide
EDC or EDAC=1-ethyl-3-(3-dimethylaminopropyl) carbodiimide
EIMS=eletron ionization mass spectroscopy
ESMS=eletron spray mass spectroscopy
EtOAc=ethyl acetate
EtOH=ethanol
HRMS=high resolution mass spectroscopy
m-CPBA=meta-chloroperbenzoic acid
MeOH=methanol
HIV=human inmmunodeficiency virus
HOAT=1-hydroxy-7-azabenzotriazole
HPLC=high performance liquid chromatography
Me=methyl
MS=mass spectroscopy
NBS=N-bromosuccinimide
NMR=nuclear magnetic resonance
TFA=trifluoroacetic acid
THF=tetrahydrofuran
TLC=thin layer chromatography
UV=ultraviolet The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

The compounds of the present invention can be prepared by the coupling of suitable 1,5-naphthyridine-3-carboxylic acids (or acid derivatives such as acid halides or esters) with the appropriate amines, as represented by the following general scheme:

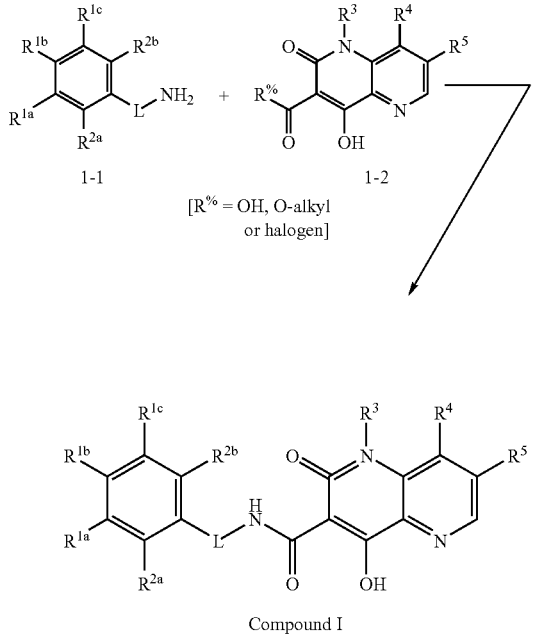

Methods for coupling carboxylic acids (and acid derivatives) with amines to form carboxamides are well known in the art. Suitable methods are described, for example, in Jerry March, *Advanced Organic Chemistry*, 3rd edition, John Wiley & Sons, 1985, pp. 370-376. Amines of formula 1-1 can be prepared using, for example, the methods described in Richard Larock, *Comprehensive Organic Transformations*, VCH Publishers Inc, 1989, pp 385-438, or routine variations thereof. Schemes 2 to 4 below illustrate and expand upon the chemistry portrayed in Scheme 1.

Compounds of Formula 1-2 in which $R^3$=H can be prepared in accordance with Scheme 2, wherein 3-amino-2-carboxy pyridine 2-1 (which can be prepared in accordance with Sucharda, *Chem. Ber.* 1925, 1727) can be esterified in acid and an alcohol to give the aminoester 2-2 in the form of a salt. Such methods are well known in the art and are described, for example, in J. March, *Advanced Organic Chemistry*, $3^{rd}$ edition, John Wiley & Sons, 1985, pp. 348-351, in Madrigal et al., *Tetrahedron: Asymmetry* 2000, 11: 3515-352, 2000, and in Culbertson et al., *J. Am. Chem. Soc.* 2000, 122: 4032-4038. The ester can be obtained as the free base through neutralization by chromatography or by an aqueous workup, after which aminoester 2-2 can be reacted with an appropriate base and methyl-3-chloro-3-oxo propionate to give the acylated amine 2-3. A similar type of acylation is described in *J. Org. Chem.* 1996, 61: 1872-1874. Alternatively, aminoester 2-2 can be treated with a dialkylmalonate at elevated temperature to accomplish the acylation (see, e.g., *Chem. Pharm. Bull.* 1993, 41: 1163-1165). When excess base is present, the acylated intermediate can undergo Dieckmann cyclization to give the 1,5-napthyridin-2-one-3-carboxylate ester 2-4 (see *J. Heterocyclic Chem.* 1998, 35: 627-636 and *J. Heterocyclic Chem.* 1993, 30: 909-912). The ester 2-4 can then be heated in an alcohol in the presence of an appropriate amine to give the 3-amide. (See *The Chemistry of Amides*, edited by S. Patai, Wiley Interscience, 1970, p. 9).

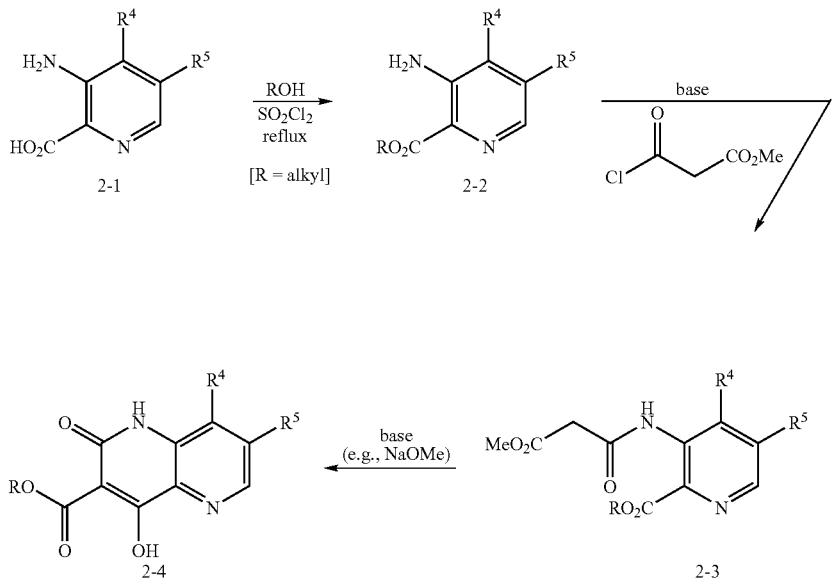

Compounds of Formula 1-2 in which $R^3$ is other than H can be prepared in accordance with Scheme 3, wherein 3-fluoro-2-cyanopyridine 3-1 (which can be prepared in accordance with Sakamoto et al., *Chem. Pharm. Bull.* 1985, 33: 565-571) can be combined with an appropriately derivatized amine 3-2 in a suitable solvent (e.g., DMSO) and heated in the presence of base (e.g., a trialkylamine such as DIPEA). The resulting 2-cyano derivative 3-3 can then be treated with an alcohol, HCl and water under Pinner conditions to give aminoester 3-4 as a salt. A discussion of the Pinner reaction can be found in *The Chemistry of the Cyano Group*, edited by S. Patai, Wiley-Interscience, 1970, p. 264. Because protonation of the aminocyanopyridine can decrease the reactivity of the cyano group, a large excess of HCl and prolonged reaction time under pressure is typically required in order to make the intermediate imidate. Refluxing the imidate with water will afford the aminoester. After an aqueous workup to obtain the aminoester in free base form, the aminoester can be treated with an appropriate base (e.g., an alkali metal alkoxide such as NaOMe) and methyl-3-chloro-3-oxo propionate to give, after cyclization, the 1,5-napthyridin-2-one-3-carboxylate ester 3-6 (see, e.g., *J. Heterocyclic Chem.* 1998, 35: 627-636 and *J. Heterocyclic Chem.* 1993, 30: 909-912), which can then be heated in an alcohol in the presence of an appropriate amine to give the 3-amde.

SCHEME 3

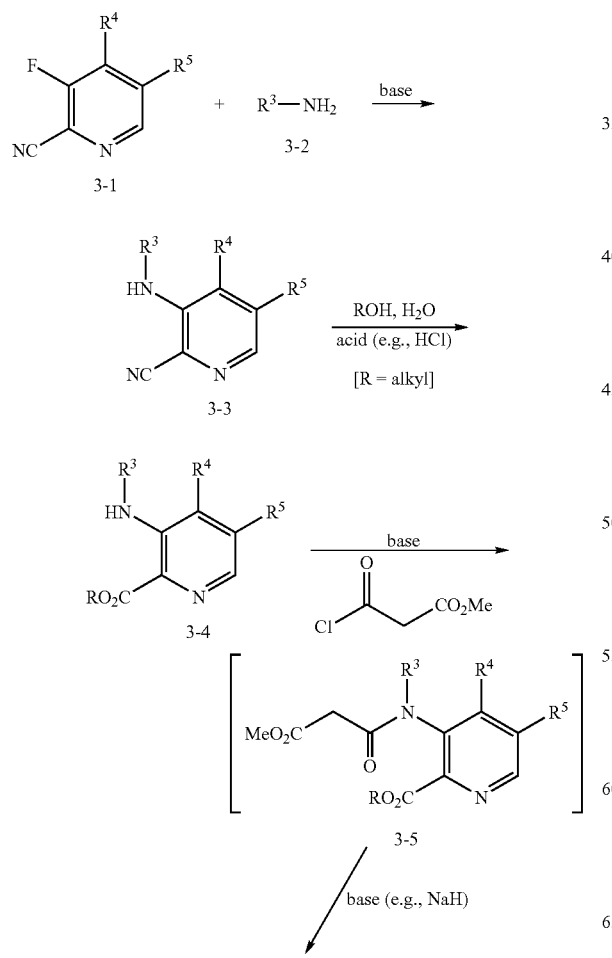

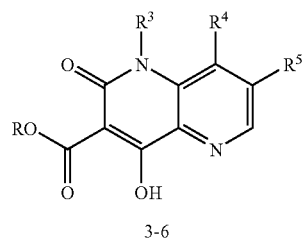

Scheme 4 illustrates a variation in the coupling reaction set forth in Scheme 1 for the case in which one of $R^{2a}$ and $R^{2b}$ in amine 1-1 is alkylsulfonyl. In the scheme, amine reactant 4-1 containing an o-alkylthio substituent on its phenyl ring is coupled to the 1,5-napthyridin-2-one-3-carboxylate ester 4-2 to provide amide 4-3, which is oxidized to the final product 4-4 using m-CPBA or another oxidant known in the art, such as those described in J. March, *Advanced Organic Chemistry*, 3$^{rd}$ edition, John Wiley & Sons, 1985, p. 1089. The alkylthio-containing amine reactant 4-1 can be prepared by methods known in the art, including via the formation of aryl anions using the metal-halogen exchange reaction of aryl halogens with strong lithium bases. This chemistry is described, for example, in B. Wakefield, *Chemistry of Organolithium Compounds*, Pergamon Press, Oxford, 1974. As an example of the application of this approach, 4-fluoro-2-methylthio-benzylamine can be prepared by the metal halogen exchange of 2-bromo-4-fluorobenzoic acid by first deprotonating the acid with Grignard reagent, then conducting the metal-bromine exchange with a strong base like n-butyllithium, and then trapping with dimethyldisulfide (see, e.g., *Synthetic Methods* 1993, 56(1): 2128) to obtain 2-methylthio-4-fluorobenzoic acid. The benzoic acid can then be converted to the primary amide using standard coupling conditions (see M. Bodansky, *The Practice of Peptide Synthesis*, Springer-Verlag, New York, 1984) and the amide reduced to the benzyl amine using a strong reducing agent, such as those described in J. March, *Advanced Organic Chemistry*, 3$^{rd}$ edition, John Wiley & Sons, 1985, p. 815). The resulting 4-fluoro-2-methylthiobenzylamine can then be coupled and oxidized into the desired naphthyridine product in the manner set forth in Scheme 4.

SCHEME 4

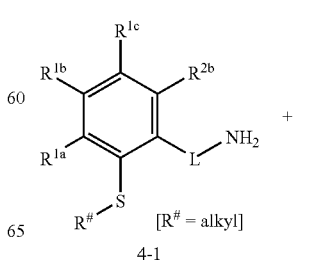

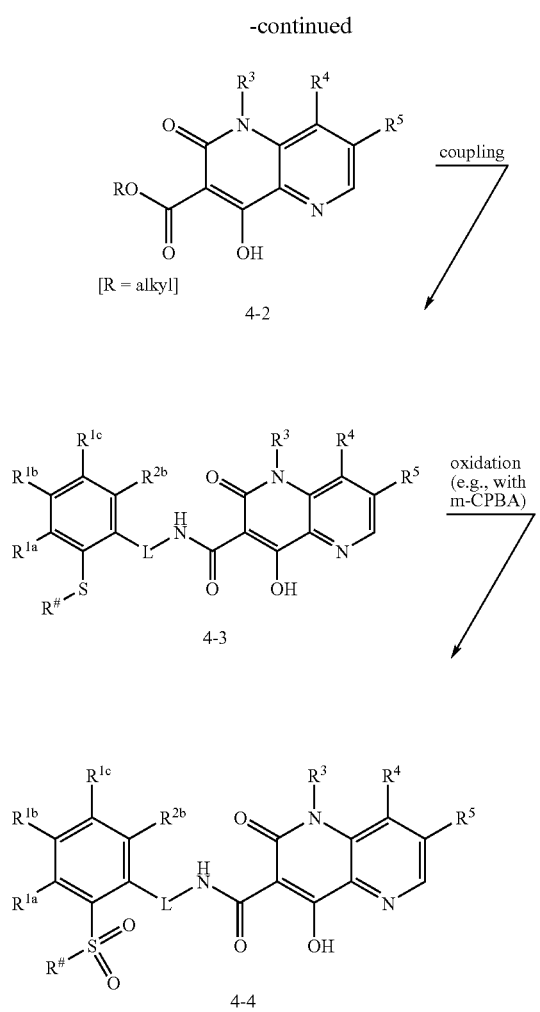

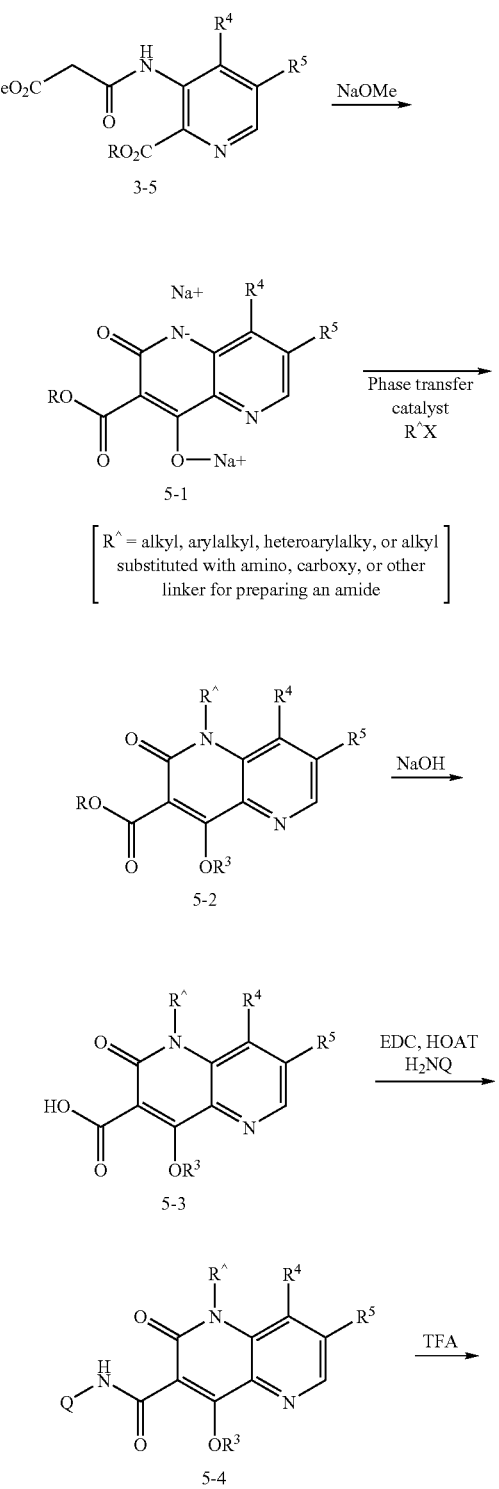

5-4, and the 8-O-alkyl group is then removed with strong acid such as trifluoroacetic acid (TFA) to give the final product 5-5. General methods for similar cleavage of phenolic alkyl groups are described in T. W. Greene, *Protective Groups in Organic Synthesis*, 3$^{rd}$ edition, John Wiley & Sons, 1999, p. 246-292.

The methyl sulfone can alternatively be incorporated into the benzyl amine before the coupling step. The appropriate 4-fluoro-2-methylsulfonyl benzylamine can be prepared in a 3-step process, in which 2,4-difluorobenzonitrile is first treated with thiomethoxide in the presence of an aprotic solvent such as toluene. Similar displacements are discussed in J. March, *Advanced Organic Chemistry*, 3$^{rd}$ edition, John Wiley & Sons, 1985, p. 589. The resulting 2-methylsulfide can then be oxidized to the sulfone as discussed above, followed by reduction of the cyano group with hydrogen and palladium catalysis in the presence of acid to afford the benzylamine. Such reductions are described in J. March, *Advanced Organic Chemistry*, 3$^{rd}$ edition, John Wiley & Sons, 1985, p. 815.

Scheme 5 illustrates a variation in the preparation of 5-N-substituted compounds. In the scheme, the acylated intermediate 3-5 is treated with a base such as sodium methoxide and the resulting bis-sodium salt 5-1 is isolated. This salt, which is very water soluble, is then treated under phase transfer conditions with a suitable alkyl halide to give the bis-alkylated product 5-2. Similar reactions are described by J. March, *Advanced Organic Chemistry*, 4$^{th}$ edition, J. Wiley & Sons, 1992, p. 362-365. The 7-ester is then hydrolyzed with NaOH to give the acid 5-3. Coupling conditions as described in Scheme 1 then give the 7-amide -continued

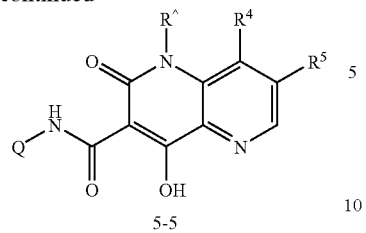

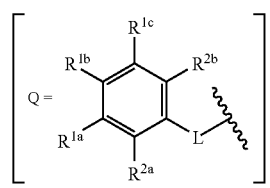

In the processes for preparing compounds and intermediates of the present invention set forth in the foregoing schemes, functional groups in various moieties and substituents may be sensitive or reactive under the reaction conditions employed and/or in the presence of the reagents employed. Such sensitivity/reactivity can interfere with the progress of the desired reaction to reduce the yield of the desired product, or possibly even preclude its formation. Accordingly, it may be necessary or desirable to protect sensitive or reactive groups on any of the molecules concerned. Protection can be achieved by means of conventional protecting groups, such as those described in *Protective Groups in Organic Chemistry*, ed. J. F. W. McOmie, Plenum Press, 1973 and in T. W. Greene & P. G. M. Wuts, *Protective Groups in Organic Synthesis*, John Wiley & Sons, 1991. The protecting groups may be removed at a convenient subsequent stage using methods known in the art. Alternatively the interfering group can be introduced into the molecule subsequent to the reaction step of concern. For example, if one or more of the substituents $R^{1a-c}$, $R^{2a-b}$, $R^3$, $R^4$ and $R^5$ in compound 1-1 can interfere with the coupling reaction between compounds 1-1 and 1-2 of Scheme 1, the substituent can be incorporated into the molecule in a post-coupling step to afford Compound I.

The following examples serve only to illustrate the invention and its practice. The examples are not to be construed as limitations on the scope or spirit of the invention.

EXAMPLE 1

N-(4-fluorobenzyl)-4-hydroxy-2-oxo-1,2-dihydro-1,5-naphthyridine-3-carboxamide

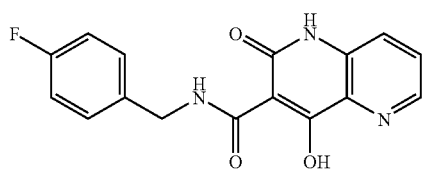

Step 1: Preparation of methyl 3-aminopyridine-2-carboxylate

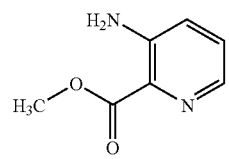

Methanol (75 mL) was cooled to 0° C. and treated dropwise with thionylchloride (3.5 mL, 48 mmol). 3-aminopyridine-2-carboxylic acid (0.9 g, 6.52 mmol, prepared as described by Sucharda, *Chem. Ber.* 1925, 1727) was added and the mixture brought to reflux. Over the next two days, two more MeOH/thionyl chloride mixtures were made and added to the reaction. The reaction was evaporated to dryness, then treated with thionyl chloride (5.7 mL, 78.3 mmole) in 75 mL of MeOH and refluxed for two more days. The reaction was evaporated to dryness and chromatographed on silica eluting with 9:1:1 EtOH/NH$_4$OH(H$_2$O to give methyl 3-aminopyridine-2-carboxylate as a yellow solid.

$^1$NMR (DMSO-d$_6$, 400 MHz) δ 7.84 (1H, dd, J=1.3, 4 Hz), 7.28 (1H, dd , J=4.0, 8.4 Hz), 7.21 (1H, dd, J=1.5, 8.4 Hz), 6.67 (1H, bs), 3.80 (3H, s) ppm. MS calc'd for C$_7$H$_8$N$_2$O$_2$ 152(M), found 153 (MH+).

The compound was also alternatively prepared as follows:

Step 1a: Preparation of 3-aminopyridine-2-carbonitrile.

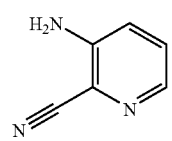

A solution of 3-fluoro-2-cyanopyridine (Sakamoto et. al., *Chem. Pharm. Bull.* 1985, 33: 565-571) (10 g, 82 mmol) in DMSO (30 mL) was placed in a pressure vessel and saturated with ammonia gas. The reaction was capped and heated to 70 degrees C. overnight. The reaction was cooled, vented and re-saturated with ammonia, then sealed and re-heated for several hours. The reaction was cooled, vented, diluted with CHCl$_3$ and the solids that had formed were filtered off. The solution was added to the top of a silica gel column (150 mm×7 inches) saturated with CHCl$_3$ and the column was eluted with a gradient of 100% CHCl$_3$ to 100% CHCl$_3$ saturated with NH$_3$. The fractions were collected and concentrated to give the product which contained some residual DMSO. This was used a in the next step.

$^1$NMR (CDCl3, 400 MHz) δ 7.83 (1H, dt, J=1.37, 4.2 Hz), 7.28 (1H, dd, J=4.3, 8.6 Hz), 7.18 (1H, dt, J=1.37, 8.6 Hz), 6.22 (2H, bs) ppm.

Step 1b: Preparation of methyl 3-aminopyridine-2-carboxylate

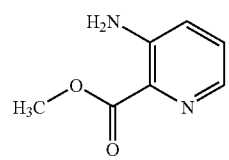

A solution of 3-aminopyridine-2-carbonitrile (9.7 g, 81.8 mmol) in MeOH (100 mL) was placed in a round bottom pressure vessel. The solution was cooled to −78° C. and HCl gas was bubbled through the solution until the volume of the solution had noticeably increased. The flask was sealed and the reaction warmed to room temperature and stirred overnight. At this time, LCMS (sampled after re-cooling the reaction to −78° C.) showed only a small amount of starting cyano compound remaining. Water (14 mL, 818 mmol) was added and the reaction transferred to a flask equipped with a reflux condenser. The reaction was refluxed overnight. The solution was concentrated and the remaining solution was basified with 1N NaOH to pH 9, then extracted with CHCL3 repeatedly until very little UV-active material was removed. The organic layers were dried over $Na_2SO_4$, filtered and evaporated to give the product as a pink solid.

$^1$NMR (CDCl3, 400 MHz) δ 8.06 (1H, dd, J=1.46,4.2 Hz), 7.21 (1H, dd, J=4.2, 8.5 Hz), 7.04 (1H, dd, J=1.46, 8.4 Hz), 5.8 (2H, bs), 3.97 (3H, s) ppm. MS calc'd for $C_7H_8N_2O_2$ 152(M), found 153 (MH+).

Step 2: Preparation of methyl 3-[(3-methoxy-3-oxopropanoyl)amino]pyridine-2-carboxylate

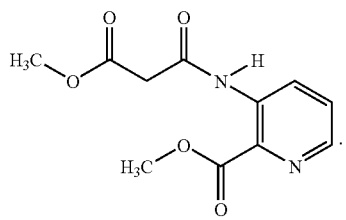

A solution of methyl 3-aminopyridine-2-carboxylate (0.25 g, 1.6 mmol) in pyridine (3 mL) was cooled to 0° C. and treated with Hunig's base (DIPEA, 0.86 mL, 4.9 mmol) and methyl 3-chloro-3-oxopropionate (0.18 mL, 1.6 mmol). The reaction was allowed to warm to room temperature. Over the next several hours, 3 more equivalents of the acid chloride was added. The reaction was evaporated and redissolved in $CHCl_3$, washed with $NH_4Cl$ and evaporated to give an oil that was purified on silica with a gradient of 80-95% EtOAc/Hexanes to give the product as a white oil. The oil was a mixture of mono- and bis-acylated products that was taken on to the next reaction.

Alternatively, methyl 3-aminopyridine-2-carboxylate (0.565 g, 3.4 mmol) was combined with dimethylmalonate (5 g, 37.4 mmol) and heated to 125° C. in a sealed tube. The reaction was stirred for 3 days. The volatiles were removed in vacuo and the crude material was taken on to the next step.

Rf (silica, 20% Hexanes/EtOAc)=0.46 (blue under UV light).

Step 3: Preparation of methyl 4-hydroxy-2-oxo-1,2-dihydro-1,5-naphthyridine-3-carboxylate

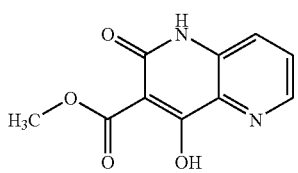

Sodium methoxide (0.73 g, 13.5 mmol) was added to 2 methyl 3-[(3-methoxy-3-oxopropanoyl)amino]pyridine-2-carboxylate (0.9 g, 3.4 mmol) dissolved in THF (20 mL). The reaction was stirred overnight. Water was added and the solvents removed. The residue was dissolved in water and purified by reverse phase HPLC eluting with a gradient of 5-40% acetonitrile/water (0.1% TFA) to give the product as a yellow solid.

$^1$H NMR (DMSO-$d_6$, 400 MHz) δ 11.7 (1H, bs), 8.53 (1H, d, J=4.2 Hz), 7.70 (1H, d, J=8.4 Hz), 7.65 (1H, dd, J=4.2, 8.2 Hz), 3.77 (3H, s) ppm.

Step 4. Preparation of N-(4-fluorobenzyl)-4-hydroxy-2-oxo-1,2-dihydro-1,5-naphthyridine-3-carboxamide A mixture of methyl 4-hydroxy-2-oxo-1,2-dihydro-1,5-naphthyridine-3-carboxylate (0.2 g, 0.91 mmol) and 4-fluorobenzyl amine (Aldrich, 0.31 mL, 2.72 mmol) in absolute ethanol (5 mL) was heated to 100° C. for 6 hours. A thick paste formed. The reaction was diluted with water and the solids collected. The crude material was purified by preparative reverse phase HPLC eluting with a gradient of 5-95% acetonitrile/water (0.1% TFA). The product precipitated from the column fractions was collected to afford the desired product as a white solid.

$^1$H NMR (DMSO, 400 MHz) δ 12.0 (1H, bs), 10.63, (1H, bs), 8.58 (1H, d, J=4.0 Hz), 7.75 (1H, d, J=8.8 Hz), 7.67 (1H, dd, J=4.2, 8.5 Hz), 7.42 (2H, dd, J=5.6, 8.4 Hz), 7.2 (2H, m), 4.58 (2H, d, J=5.7 Hz) ppm. HRMS: calc'd for $C_{16}H_{12}FN_3O_3$+1H=314.0936, observed 314.0946. C, H, N calc'd for $C_{16}H_{12}FN_3O_3$ C=60.99, H=3.90, N=13.34, found C=60.93, H=3.80, N=13.02.

EXAMPLE 2

1-{2-[(dimethylamino)sulfonyl]ethyl}-N-(4-fluorobenzyl)-4-hydroxy-2-oxo-1,2-dihydro-1,5-naphthyridine-3-carboxamide

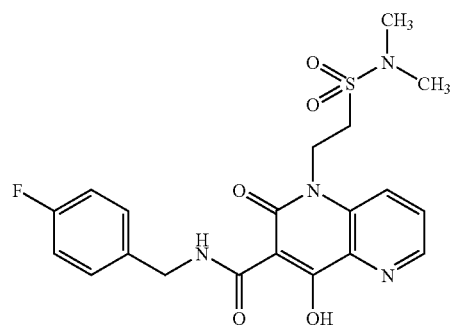

Step 1: Preparation of benzyl 2-(chlorosulfonyl)ethylcarbamate

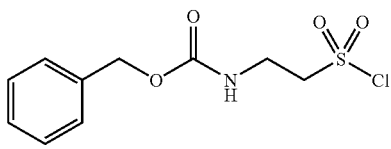

This compound was prepared using the method of T. S. Widlanski and J. Huang, *Tet. Lett.* 1992, 33: 2657. A solution of triphenylphosphine (17.6 g, 67.4 mmol) in dry CH$_2$Cl$_2$ (90 mL) was cooled to zero degrees C. under nitrogen and treated with neat sulfuryl chloride (5.96 mL, 74.2 mmol) to give a yellow solution. The solution was recooled to 5 degrees C. and crushed solid sodium 2-{[(benzyloxy)carbonyl]amino}ethanesulfonate (12 g, 42.6 mmol) prepared as described by Bricas et al., *Biochimica et Biophysica Acta* 1955, (18), 358, was added all at once to give a white suspension. The reaction was allowed to warm to room temperature and stirred for 3 hours. The volatiles were removed in vacuo to give an oily/solid residue that was suspended in EtOAc and added to the top of a silica column (3 inches by 150 mm) packed in EtOAc. The product was eluted with EtOAc and the UV active fractions were combined and evaporated to give the product as a white solid.

$^1$H NMR (CDCl$_3$, 400 MHz) δ 7.35 (5H, bs), 5.20 (1H, bs), 5.12 (2H, bs), 3.89 (2H, bs), 3.85 (2H, bs) ppm.

Step 2: Preparation of benzyl 2-[(dimethylamino)sulfonyl] ethylcarbamate

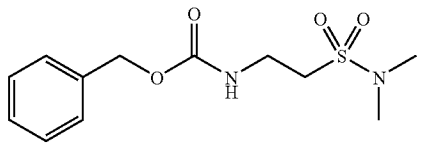

A solution of dry CHCl$_3$ (150 mL)in an oven dried flask was tared and gaseous dimethylamine was bubbled into the solution until the gain in tare was 3.4 g. A dropping funnel was added, the flask was flushed with nitrogen and the solution cooled to 0° C. Benzyl 2-(chlorosulfonyl)ethylcarbamate (8.8 g, 31.6 mmol) in CHCl$_3$ (20 mL) was added dropwise. The reaction was warmed to room temperature, transferred to a separatory funnel and the solution was washed twice with 10% KHSO$_4$ solution. The organic layer was dried over Na$_2$SO$_4$, filtered and evaporated to give the crude product as an oil that was used as is in the next step.

$^1$H NMR (CDCl$_3$, 400 MHz) δ 7.35 (5H, bs), 5.45 (1H, bs), 5.11 (2H, bs), 3.69 (2H, m), 3.13 (2H, m), 2.86 (6H, s) ppm.

Step 3: Preparation of 2-[(dimethylamino)sulfonyl]ethanaminium chloride

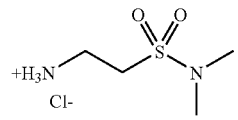

Benzyl 2-[(dimethylamino)sulfonyl]ethylcarbamate (8.8 g, 30.7 mmol) was suspended/dissolved in 6N HCl (75 mL) and the mixture was heated to 90° C. The solids dissolved. After 1.5 hours the reaction was cooled and extracted with ether. The aqueous layer was evaporated to give a sticky white solid. The ether layer was found to contain unreacted starting material. This was retreated with 6 N HCl at room temperature overnight. The reaction was washed with ether and the aqueous layer combined with the previously isolated product and evaporated to give a white solid.

$^1$H NMR (DMSO-D$_6$, 400 MHz) δ 8.2 (2H, bs), 3.43 (2H, m), 3.15 (2H, m), 2.80 (6H, s) ppm.

Step 4: Preparation of 2-[(2-cyanopyridin-3-yl)amino]-N,N-dimethylethanesulfonamide

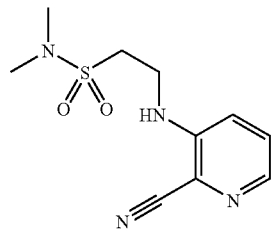

3-fluoro-2-cyanopyridine (Sakamoto et. al., *Chem. Pharm. Bull.* 1985, 33: 565-571) (1 g, 8.2 mmol) was placed in a high pressure tube equipped with a stir bar. DMSO (7 mL), Hunig's base (1.57 mL, 9.0 mmol) and 2-[(dimethylamino)sulfonyl]-ethanaminium chloride (1.7 g, 9.0 mmol) were added and the vessel was sealed and heated to 80° C. for 5.5 hours, then stirred at room temperature overnight. The reaction was treated with an additional 0.3 equivalent of Hunig's base and 0.2 equivlanet of the amine salt and heated for 3 hours, but the reaction progressed no further. The mixture was cooled, added to the top of a silica gel column (60 mm by 7 inches) packed in EtOAc and the column eluted with EtOAc. Careful cutting of fractions allowed isolation of the product after evaporation as a clear, colorless oil that solidified upon standing.

$^1$H NMR (CDCl$_3$, 400 MHz) δ 8.05 (1H, dd, J=1.0, 4.4 Hz), 7.34 (1H, dd, J=4.6, 8.6 Hz), 7.10 (1H, d, J=8.6 Hz), 5.20 (1H, bs), 3.75 (2H, dd, J=6.3, 12.6 Hz), 3.2 (2H, m), 2.92 (6H, s) ppm.

Step 5: Preparation methyl 3-({2-[(dimethylamino)sulfonyl]ethyl}amino)-pyridine-2-carboxylate

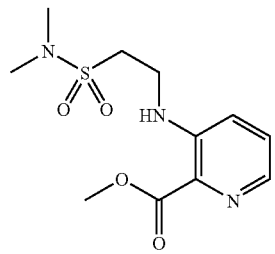

2-[(2-cyanopyridin-3-yl)amino]-N,N-dimethylethanesulfonamide (1.4 g, 5.5 mmol) was dissolved in 50 mL MeOH and placed in a 100 mL pressure flask. The solution was cooled to –78° C. and HCl gas was bubbled through the solution until the volume of the solution had noticeably increased. The flask was sealed and the reaction warmed to room temperature and stirred for 4 hours. At this time, LCMS (sampled after re-cooling the reaction to –78° C.) showed only a small amount of starting cyano compound remaining. Water (1 mL, 55 mmol) was added and the reaction transferred to a flask equipped with a reflux condenser. The reaction was refluxed for 1.5 hours, stirred at room temperature overnight, then refluxed for 2 more hours, then stirred at room temperature for 48 hours. The solution was evaporated to dryness to give a green/yellow foam that was then partitioned between CHCl$_3$ and saturated NaHCO$_3$. The layers were separated and the aqueous was extracted circa 10 times or until very little UV-active material was removed. The organic layers were dried over Na$_2$SO$_4$, filtered and evaporated to give the product as a clear oil that solidified upon standing.

¹H NMR (CDCl₃, 400 MHz) δ 8.05 (1H, d, J=4.2 Hz), 7.34 (1H, dd, J=4.2, 8.6 Hz), 7.12 (1H, d, J=8.6 Hz), 3.97 (3H, s), 3.75 (2H, dd, J=6.6, 13.1 Hz), 3.22 (2H, m), 2.90 (6H, s) ppm Step 6: Preparation of methyl 1-{2-[(dimethylamino)sulfonyl]ethyl}-4-hydroxy-2-oxo-1,2-dihydro-1,5-naphthyridine-3-carboxylate

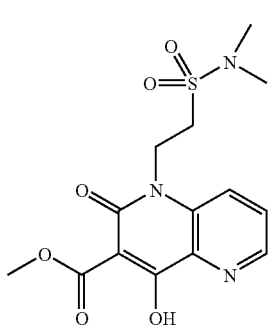

Methyl 3-({2-[(dimethylamino)sulfonyl]ethyl}amino)pyridine-2-carboxylate (0.877 g, 3.05 mmol) was dissolved in dry THF (10 mL) and cooled to 0° C. NaH (338 mg, 60% suspension in oil, 8.45 mmol) was added and a precipitate formed. The slurry was treated with methyl 3-chloro-3-oxopropionate (0.410 mL, 3.82 mmol) and 3 drops of MeOH and allowed to warm and stir overnight. The reaction was concentrated somewhat in vacuo, then poured into water. The mixture was extracted once with CHCL₃, then acidified and extracted repeatedly with CHCl₃ until only a trace of UV active material is removed. The acidic organic extracts were dried over Na2SO4, filtered and evaporated to give the product as a pink foam.

¹H NMR (CDCl₃, 400 MHz), δ 8.70 (1H, d, J=3.8 Hz), 7.92 (1H, d, J=8.5 Hz), 7.67 (1H, dd, J=4.2, 8.7 Hz), 4.6 (2H, m), 4.07 (3H, s), 3.34 (2H, m), 2.91 (6H, m) ppm.

Step 7: Preparation of 1-{2-[(dimethylamino)sulfonyl]ethyl}-N-(4-fluorobenzyl)-4-hydroxy-2-oxo-1,2-dihydro-1,5-naphthyridine-3-carboxamide Methyl 1-{2-[(dimethylamino)sulfonyl]ethyl}-4-hydroxy-2-oxo-1,2-dihydro-1,5-naphthyridine-3-carboxylate (0.3 g, 0.84 mmol) was suspended in 8 mL of absolute EtOH and treated with 4-fluorobenzyl amine (0.29 mL, 2.53 mmol). The mixture was brought to reflux for 2.5 hours, cooled, and the solids collected and washed with a little cold EtOH to give the product as a white solid.

¹H NMR (CDCl₃, 400 MHz) δ 10.4 (1H, bs), 8.75 (1H, d, J=4.3 Hz), 7.92 (1H, d, J=8.7 Hz), 7.66 (1H, dd, J=4.2, 8.7 Hz), 7.36 (2H, dd, J=5.4, 8.6 Hz), 7.05 (2H, m), 4.6 (4H, m), 3.28 (2H, m), 2.91 (6H, s) ppm. HRMS: calc'd for C₂₀H₂₁FN₄O₅S+1H=449.1290, observed 449.1286. C, H, N calc'd for C₂₀H₂₁FN₄O₅S C=53.56, H=4.72, N=12.49, found C=53.51, H=4.58, N=12.42.

EXAMPLE 3

1-{2-[(dimethylamino)sulfonyl]ethyl}-N-[4-fluoro-2-(methylsulfonyl)benzyl]-4-hydroxy-2-oxo-1,2-dihydro-1,5-naphthyridine-3-carboxamide

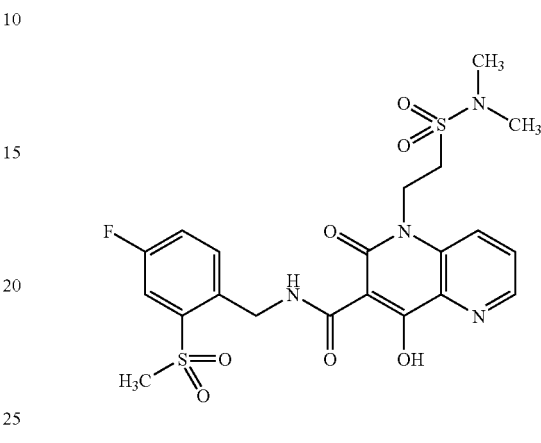

Step 1: Preparation of 4-fluoro-2-(methylthio)benzoic acid.

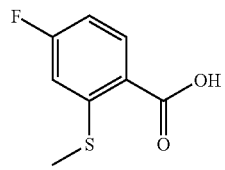

A solution of 2-bromo-4-fluorobenzoic acid (15 g, 68.5 mmol, Marshallton Research Laboratories) in THF (150 mL) under argon at 0° C. was treated with chloro(methyl)magnesium (5.64 g, 75.34 mmol, 2.94 M in THF) over 5 minutes. The temperature during addition was maintained below 10° C. The resulting solution was cooled to −78° C. and n-butyllithium (9.65 g, 150.7 mmol, 2.5M in hexanes) was added over 10 minutes. The reaction was kept below −65° C. during the addition. The reaction was stirred at −78° C. for 50 minutes. A solution of (methyldithio)methane (38.71 g, 410.9 mmol) in THF (20 mL), precooled to −78° C., was added by cannula. The reaction was stirred for 10 minutes, warmed to zero ° C. and stirred at zero ° C. for 2 hours until a solid began to precipitate. The reaction was allowed to warm to 25° C. and stirred overnight. The reaction was poured into 1N HCl and extracted with EtOAc. The water layer was extracted with EtOAc twice more, the organic layers were combined, dried over Na₂SO₄, filtered and evaporated. The crude solid was suspended in 5% EtOAc/Hexanes and stirred for an hour, then filtered and dried to give the product as a white solid.

¹H NMR (d-DMSO, 400 MHz) δ 7.98 (1H, dd, J=8.8, 6.4 Hz), 7.15 (1H, d, J=10.8 Hz), 7.05 (1H, dd, J=8.8, 6.4 Hz), 2.41 (3H, bs) ppm. EI HRMS: exact mass calc'd for C₈H₇FO₂S 186.0151 (M), found 186.0151.

Step 2. Preparation of 4-fluoro-2-(methylthio)benzamide.

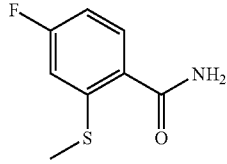

To a solution of 4-fluoro-2-(methylthio)benzoic acid (8.1 g, 43.6 mmol) in degassed DMF (100 mL) under nitrogen was added ammonium chloride (4.66 g, 87.2 mmol) followed by 1-hydroxy-7-azabenzotriazole (11.87 g, 87.2 mmol) and N,N,N-diisopropylethylamine (30.38 mL, 174.4 mmol). To this mixture was added N-[3-(dimethylamino)propyl]-N'-ethylcarbodiimide hydrochloride and the reaction was stirred for 16 hour. LCMS analysis indicated that the reaction was complete. The DMF was removed in vacuo and the residue was partitioned between methylene chloride (800 mL) and 5% aqueous HCl (400 mL). The organic phase was washed with water (400 mL), saturated sodium bicarbonate solution (400 mL), and brine (400 mL). The organics were dried over $Na_2SO_4$, filtered, and reduced to a small volume in vacuo. The product crystallized upon solvent reduction. The crystals were filtered and dried iii vacuo to afford the title compound.

$^1$H NMR (CDCl$_3$, 400 MHz) δ 7.67 (1H, dd, J=8.4, 5.86 Hz), 7.00 (1H, dd, J=9.89, 2.4 Hz), 6.88 (1H, dd, J=8.4, 2.4 Hz), 2.48 (3H, s) ppm. APCI HRMS: exact mass calc'd for $C_8H_8FNOS$ 186.0783 (MH$^+$), found 186.0365.

Step 3: Preparation of 1-[4-fluoro-2-(methylthio)phenyl]methanamine

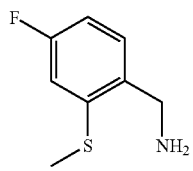

A slurry of 4-fluoro-2-(methylthio)benzamide (9 g, 48.6 mmol) in diethyl ether (500 mL) was cooled to 0° C. under nitrogen and lithium aluminum hydride (5.53 g, 145.8 mmol, 1.0 M in diethyl ether) was added dropwise. The reaction was allowed to stir with slow warming to 25° C. overnight. The reaction was quenched via the addition of water (5.53 mL), 15% NaOH (5.53 mL) and water (16 mL). The mixture was stirred, the lithium salts precipitated out and were filtered off. The organic filtrate was washed with saturated sodium bicarbonate (300 mL) and brine (300 mL), dried over $Na_2SO_4$, filtered and reduced to a small volume. The resulting brown oil was placed under high vacuum to give the desired compound as a free base.

$^1$H NMR (d-DMSO, 400 MHz) δ 7.43 (1H, t, J=7 Hz), 7.03 (1H, dd, J=10.0, 2.4 Hz), 6.94 (1H, ddd, J=8.8, 6.4, 2.4 Hz), 3.64 (2H, s), 2.50 (3H, s) ppm. APCI HRMS: exact mass calc'd for $C_8H_{10}FNS$ 172.0591 (MH$^+$), found 172.0566.

Step 4: Preparation of 1-{2-[(dimethylamino)sulfonyl]ethyl}-N-[4-fluoro-2-(methylthio)benzyl]-4-hydroxy-2-oxo-1,2-dihydro-1,5-naphthyridine-3-carboxamide

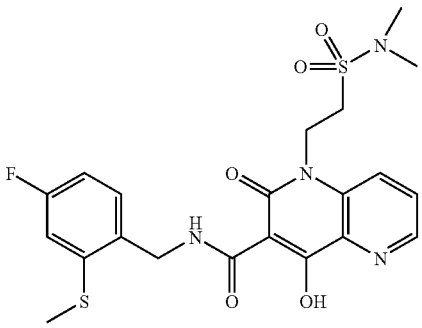

In a manner similar to that described in Example 2, methyl 1-{2-[(dimethylamino)sulfonyl]ethyl}-4-hydroxy-2-oxo-1,2-dihydro-1,5-naphthyridine-3-carboxylate (0.3 g, 0.84 mmol) was suspended in 8 mL of absolute EtOH and treated with 1-[4-fluoro-2-(methylthio)phenyl]methanamine (0.21 g, 1.3 mmol). The mixture was brought to reflux for 4.5 hours, cooled, and the solids collected and washed with a little cold EtOH to give the product as a white solid.

$^1$H NMR (CDCl$_3$, 400 MHz) δ 10.53 (1H, bs), 8.67 (1H, d, J=4.1 Hz), 8.05 (1H, d, J=8.8 Hz), 7.83 (1H, dd, J=4.1, 8.6 Hz), 7.35 (1H, m), 7.15 (1H, dd, J=2.2, 10 Hz), 6.99 (1H, app. dt, J=2.1, 8.4 Hz), 4.6 (4H, m), 3.28 (2H, t, J=7.6 Hz), 2.79 (6H, s), 2.55 (3H, s) ppm.

Step 5: 1-{2-[(dimethylamino)sulfonyl]ethyl}-N-[4-fluoro-2-(methylsulfonyl)benzyl]-4-hydroxy-2-oxo-1,2-dihydro-1,5-naphthyridine-3-carboxamide 1-{2-[(dimethylamino)sulfonyl]ethyl}-N-[4-fluoro-2-(methylthio)benzyl]-4-hydroxy-2-oxo-1,2-dihydro-1,5-naphthyridine-3-carboxamide (0.194 g, 0.39 mmol) was dissolved in a 1:2 mixture of CHCl$_3$ and CH$_2$Cl$_2$ (10 mL) and treated with m-CPBA (380 mg, 70% pure, 1.54 mmol). The solution was stirred at room temperature overnight. The reaction was treated with 3 drops of DMSO and stirred for 30 minutes, then poured into a separatory funnel and extracted twice with saturated NaHCO$_3$ solution. The organic layer was dried over Na$_2$SO$_4$, filtered and evaporated to give the product as a foam. A portion was purified on reverse phase HPLC eluting with a gradient of 95:5 to 5:95 water/acetonitrile (0.1% TFA) and the product precipitated out of the fractions and was collected as a white solid.

$^1$H NMR (DMSO-d6, 400 MHz) δ 10.73 (1H, bs), 8.67 (1H, d, J=3.8 Hz), 8.05 (1H, d, J=8.8 Hz), 7.84 (1H, dd, J=4.3, 8.7 Hz), 7.75 (1H, dd, J=2.6, 8.6 Hz), 7.69(1H, dd, J=5.5, 8.6 Hz), 7.61 (1H, app. dt, J=2.8, 8.3 Hz), 4.94 (2H, J=5.7 Hz), 4.60 (2H, m), 3.41 (5H, m), 2.80 (6H, s), ppm. HRMS: calc'd for $C_{21}H_{23}FN_4O_7S_2$+1H=527.1065, observed 527.1051. C, H, N calc'd for $C_{21}H_{23}FN_4O_7S_2$ C=47.90, H=4.40, N=10.64, found C=47.85, H=4.27, N=10.43.

EXAMPLE 4

1-(1,4-dioxan-2-ylmethyl)-N-(4-fluorobenzyl)-4-hydroxy-2-oxo-1,2-dihydro-1,5-naphthyridine-3-carboxamide

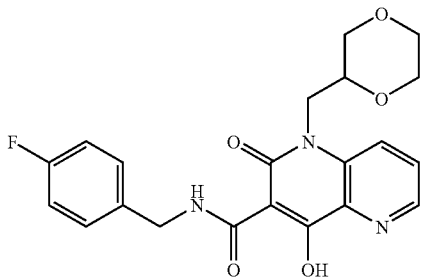

In the manner described in Example 2, 3-fluoro-2-cyanopyridine was reacted with R,S-1,4-dioxan-2-ylmethylamine (Chembridge Corporation), the cyano group transformed into a methyl ester via the Pinner reaction, the resulting amine acylated with methyl 3-chloro-3-oxopropionate and cyclized to the 1,5-naphthyridine-6-one, and the amide formed by reaction with 4-fluorobenzylamine to give the product as a yellow-green solid.

$^1$H NMR (DMSO-d6, 400 MH) δ 10.62 (1H, bs), 8.63 (1H, d, J=4.2 Hz), 8.18 (1H, d, J=8.9 Hz), 7.77 (1H, ddd, J=1.3, 4.2, 8.7 Hz), 7.44 (2H, m), 7.19(2H, m), 4.58 (2H, J=5.1 Hz), 4.30 (2H, m), 3.84 (1H, m), 3.80 (1H, d, J=12.1 Hz), 3.66 (1H, m), 3.60 (1H, m), 3.45 (2H, m), 3.40 (1H, m) ppm. C, H, N calc'd for $C_{21}H_{20}FN_3O_5$ C=61.01, H=4.88, N=10.16, found C=60.77, H=4.71, N=9.97.

EXAMPLE 5

1-(1,4-dioxan-2-ylmethyl)-N-[4-fluoro-2-(methylthio)benzyl]-4-hydroxy-2-oxo-1,2-dihydro-1,5-naphthyridine-3-carboxamide

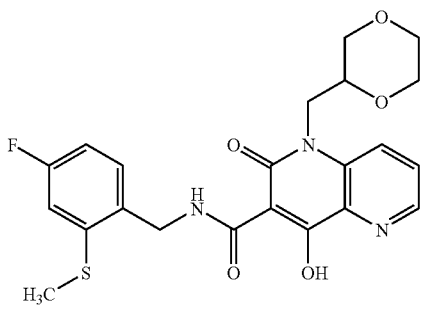

In a manner similar to that described in Examples 2 and 3, the title product was obtained as a white solid.

$^1$H NMR (CDCl$_3$, 400 MHz) δ 10.49 (1H, bs), 8.70 (1H, d, J=4.2 Hz), 7.99 (1H, d, J=8.3 Hz), 7.57 (1H, dd, J=4.2, 8.7 Hz), 7.35 (1H, dd, J=5.0, 8.4 Hz), 6.95(1H, dd, J=2.5,9.6 Hz), 6.83 (1H, app. dt, J=2.6, 8.3 Hz), 4.66 (2H, J=5.9 Hz), 4.38 (1H, dd, J=3.4, 14.7 Hz), 4.08 (1H, dd, J=6.6, 14.5 Hz), 3.94 (1H, m), 3.92 (1H, d, J=10.3 Hz), 3.75-3.60 (4H, m), 3.43 (1H, dd, J=10.6, 11.8 Hz), 2.51 (3H, s) ppm. C, H, N calc'd for $C_{22}H_{22}FN_3O_5S$ C=57.51, H=4.83, N=9.15, found C=57.15, H=4.63, N=8.95.

EXAMPLE 6

1-(1,4-dioxan-2-ylmethyl)-N-[4-fluoro-2-(methylsulfonyl)benzyl]-4-hydroxy-2-oxo-1,2-dihydro-1,5-naphthyridine-3-carboxamide

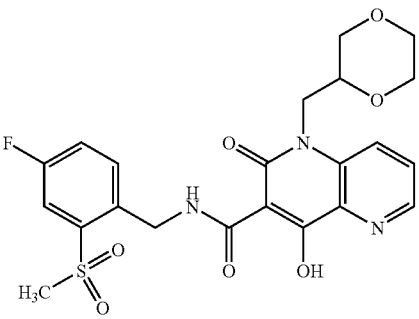

In a manner similar to that described for Examples 3 and 4, the title product was obtained as a white foam.

$^1$H NMR (CDCl$_3$, 400 MHz) δ 10.8 (1H, bs), 8.70 (1H, d, J=4.4 Hz), 8.01 (1H, d, J=8.9 Hz), 7.78 (1H, dd, J=2.8, 8.1 Hz), 7.69 (1H, dd, J=5.1, 8.4 Hz), 7.59 (1H, dd, J=4.3, 8.8 Hz), 7.33 (1H, app. dt, J=2.5, 8.0 Hz), 4.98 (2H, J=6.2 Hz), 4.42 (1H, dd, J=3.2, 14.7 Hz), 4.08 (1H, dd, J=6.5, 14.5 Hz), 3.94 (2H, m), 3.75-3.55 (4H, m), 3.43 (1H, m) 3.25 (3H, s) ppm. HRMS: calc'd for $C_{22}H_{22}FN_3O_7S$+1H=492.1235, observed 492.1219.

EXAMPLE 7

N-(4-fluorobenzyl)-4-hydroxy-1-{2-[methyl(methylsulfonyl)amino]ethyl}-2-oxo-1,2-dihydro-1,5-naphthyridine-3-carboxamide

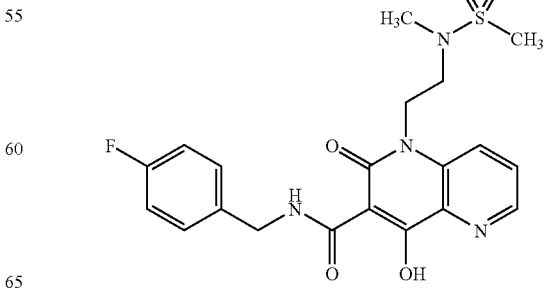

Step 1: Preparation of benzyl 2-(methylamino)ethylcarbamate

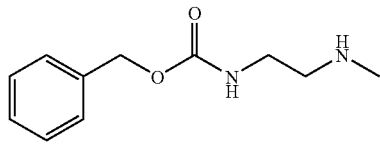

To a solution of N-methyl ethylene diamine (10 g, 135 mmol) in CHCL₃ (100 mL) was added TFA (11.43 mL, 148.4 mmol) and the solution was stirred for several minutes. The reaction was then treated successively with 1-{[(benzyloxy)carbonyl]oxy}pyrrolidine-2,5-dione (Aldrich, 43.7 g, 175.3 mmol) and 18-crown-6 (71.3 g, 269.8 mmol). The reaction became slightly green. After stirring for 1 hour at room temperature, TLC (ninhydrin stain) showed no remaining starting amine. The reaction was transferred to a separatory funnel and washed with KOH solution. The aqueous layer was back-extracted several times. The organic layers were combined, dried over Na₂SO₄, filtered and concentrated to give 100 g of a yellow oil. The oil was dissolved in 300 ml CHCl₃ and half of this volume was chromatographed on silica (150 mm×7 inches, 1 Kg silica gel, packed in CHCl₃) eluting with CHCl₃ saturated NH₃. The pure fractions were collected and the remaining half of the crude chromatographed in the same way. Product fractions contaminated with some bis-CBZ protected material were dissolved in CHCl₃ and washed with acid water. The aqueous was then basified and extracted with CHCl₃. The organic layer was dried over Na₂SO₄, filtered and concentrated with the other pure fractions to give the product as a clear, colorless oil.

¹H NMR (CDCl₃, 400 MHz) δ 7.3-7.4 (5H, m), 5.13 (2H, s), 3.35 (2H, bs), 2.96 (3H, s), 2.85 (2H, bs), 1.25 (2H, bs).

Step 2: Preparation of benzyl 2-[methyl(methylsulfonyl)amino]ethylcarbamate

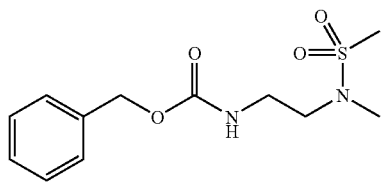

A solution of benzyl 2-(methylamino)ethylcarbamate (0.05 g, 0.24 mmol) in CH₂Cl₂ (5 mL was cooled to 6° C. and treated with triethylamine (0.1 mL, 0.72 mmol) and methanesulfonyl chloride (0.02 mL, 0.24 mmol). The reaction was warmed to room temperature and stirred overnight. The reaction was washed with 10% KHSO₄, the organic layer was dried over Na₂SO₄, filtered and evaporated to give the product.

¹H NMR (CDCl₃, 400 MHz) δ 7.3-7.4 (5H, m), 5.23 (1H, bs), 5.10 (2H, s), 3.4 (2H, m), 3.25 (2H, m), 2.88 (3H, s), 2.78 (3H, s).

Step 3: Preparation of 2-[methyl(methylsulfonyl)amino] ethanaminium chloride

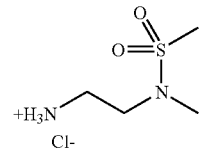

A solution of benzyl 2-[methyl(methylsulfonyl)amino] ethylcarbamate (6.1 g, 30.7 mmol) was treated with 6 N HCl (100 mL) and heated to 90° C. for 1.5 hours then stirred at room temperature overnight. The solution was extracted twice with ether and the aqueous layer was evaporated to give the product as a sticky white solid that was taken on to the next step.

Rf (silica, 20% MeOH/CHCl₃/NH₃)=0.17

Step 4: Preparation of N-{2-[(2-cyanopyridin-3-yl)amino]ethyl}-N-methylmethanesulfonamide

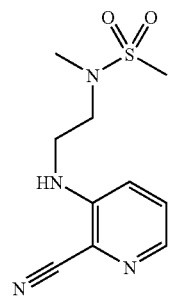

In a manner similar to that described for Example 2, 2-[methyl(methylsulfonyl)amino]ethanaminium chloride (4 g, 25.4 mmol) was dissolved in DMSO (20 mL) and treated with 3-fluoro-2-cyanopyridine (2.5 g, 21.2 mmol) and Hunig's base (4.4 mL, 25.4 mmol) and heated to 90 degrees under pressure. The product was isolated as an oily off-white solid.

¹H NMR (CDCl₃, 400 MHz) δ 8.18 (1H, m), 7.38 (2H, m), 5.0 (1H, bs), 3.62 (2H, m), 3.5 (2H, m), 3.05 (3H, s), 3.00 (3H, s).

Step 5: Preparation of methyl 4-hydroxy-1-{2-[methyl(methylsulfonyl)amino]ethyl}-2-oxo-1,2-dihydro-1,5-naphthyridine-3-carboxylate

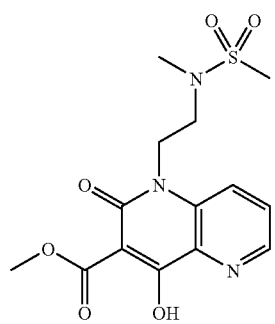

In a manner similar to that described for Example 2, N-{2-[(2-cyanopyridin-3-yl)amino]ethyl}-N-methylmethanesulfonamide was treated with MeOH, HCl and water to give methyl 3-({2-[methyl(methylsulfonyl)amino]ethyl}amino)pyridine-2-carboxylate after aqueous workup. The crude product was then treated with NaH and methyl 3-chloro-3-oxopropionate as described in Example 2 and after aqueous workup the crude methyl 4-hydroxy-1-{2-[methyl(methylsulfonyl)amino]ethyl}-2-oxo-1,2-dihydro-1,5-naphthyridine-3-carboxylate was obtained as a pink foam. A portion of the material was crystallized from EtOH to give the product as light brown crystals.

¹H NMR (CDCl₃, 400 MHz) δ 8.67 (1H, d, J=4.3 Hz), 8.00 (1H, d, J=8.7 Hz), 7.65 (1H, dd, J=4.3, 8.7 Hz), 4.44 (2H, m), 4.07 (3H, s), 3.43 (2H, m), 2.96 (3H, s), 2.84 (3H, s).

Step 6: Preparation of N-(4-fluorobenzyl)-4-hydroxy-1-{2-[methyl(methylsulfonyl)amino]ethyl}-2-oxo-1,2-dihydro-1,5-naphthyridine-3-carboxamide In a manner similar to that described in Example 2, methyl 4-hydroxy-1-{2-[methyl(methylsulfonyl)amino]ethyl}-2-oxo-1,2-dihydro-1,5-naphthyridine-3-carboxylate was dissolved in EtOH and treated with 4-fluorobenzylamine at reflux. After cooling the product fell out of solution and was collected. The crude was dissolved in CHCl₃, washed with 10% KHSO₄ solution, the organic was dried over MgSO₄, filtered and evaporated to give the product as a white foam.

¹H NMR (CDCl₃, 400 MHz) δ 10.46 (1H, bs), 8.72 (1H, d, J=4.2 Hz), 8.02 (1H, d, J=8.9 Hz), 7.65 (1H, dd, J=4.3, 8.7 Hz), 7.35 (2H, dd, J=5.5, 8.3 Hz), 7.05 (2H, m), 4.63 (2H, d, J=6.0 Hz), 4.45 (2H, m), 3.39 (2H, m), 2.95 (3H, s), 2.84 (3H, s). HRMS: calc'd for $C_{20}H_{21}FN_4O_5S+1H=449.1289$, observed 449.1266.

EXAMPLE 8

N-[4-fluoro-2-(methylsulfonyl)benzyl]-4-hydroxy-1-{2-[methyl(methylsulfonyl)amino]ethyl}-2-oxo-1,2-dihydro-1,5-naphthyridine-3-carboxamide

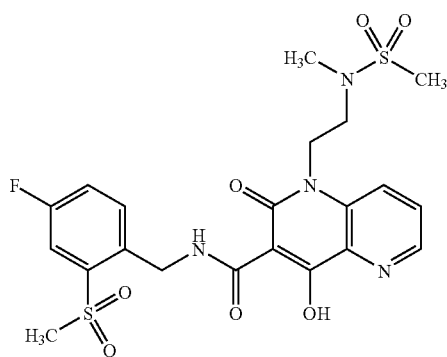

In a manner similar to that described for Example 3, methyl 4-hydroxy-1-{2-[methyl(methylsulfonyl)amino]ethyl}-2-oxo-1,2-dihydro-1,5-naphthyridine-3-carboxylate was dissolved in EtOH and treated at reflux with 1-[4-fluoro-2-(methylthio)phenyl]methanamine. The crude product was oxidized with m-CPBA as described for Example 3 to give the product as a white foam.

¹H NMR (CDCl₃, 400 MHz) δ 10.76 (1H, bs), 8.72 (1H, d, J=4.2 Hz), 8.02 (1H, d, J=8.9 Hz), 7.78 (1H, dd, J=2.8, 8.2 Hz), 7.72 (1H, dd, J=5.1, 8.6 Hz), 7.65 (1H, dd, J=4.2, 8.8 Hz), 7.33 (1H, app. dt, J=2.8, 8.1 Hz), 4.97 (2H, d, J=6.2 Hz), 4.47 (2H, m), 3.41 (2H, m), 3.24 (3H, s), 2.95 (3H, s), 2.83 (3H, s). HRMS: calc'd for $C_{21}H_{23}FN_4O_7S_2+1H=527.1065$, observed 527.1031.

EXAMPLE 9

1-[(1,1-Dioxidotetrahydrothien-3-yl)methyl]-N-(4-fluorobenzyl)-4-hydroxy-2-oxo-1,2-dihydro-1,5-naphthyridine-3-carboxamide

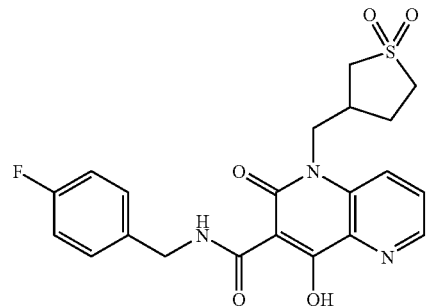

In a manner similar to that described in Example 2, (1,1-dioxidotetrahydrothien-3-yl)methanaminium chloride (Chembridge) was treated with 3-fluoro-2-cyano pyridine and then further derivatized to give the final compound.

¹H NMR (DMSO-d6, 400 MHz) δ 10.62 (1H, bs), 8.65 (1H, d, J=4.2 Hz), 8.24 (1H, d, J=4.1 Hz), 7.78 (1H, dd, J=4.1, 8.6 Hz), 7.43 (2H, m), 7.19 (2H, m), 4.59 (2H, m), 4.40 (2H, m), 3.29, (1H, m), 3.23 (1H, m), 3.02 (2H, m), 2.80 (1H, m), 2.22 (1H, m)1.94 (1H, m).

C, H, N calc'd for $C_{21}H_{20}FN_3O_5S$ 1.5 H₂O C=53.38, H=4.91, N=8.89, found C=53.38, H=4.59, N=8.54.

EXAMPLE 10

N-[4-fluoro-2-(methylsulfonyl)benzyl]-4-hydroxy-1-[2-(methylsulfonyl)ethyl]-2-oxo-1,2-dihydro-1,5-naphthyridine-3-carboxamide

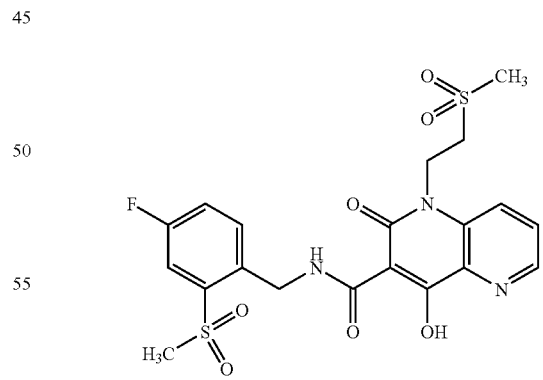

In a manner similar to that described for Examples 2 and 3, 2-(methylthio)ethanamine was reacted with 3-fluoro-2-cyanopyridine and then derivatized to give the final product.

¹H NMR (CDCl₃, 400 MHz) δ 10.65 (1H, bs), 8.73 (1H, d, J=4.0 Hz), 7.92 (1H, d, J=8.8 Hz), 7.78 (1H, dd, J=2.6, 8.2 Hz), 7.73 (1H, dd, J=5.1, 8.4 Hz), 7.66 (1H, dd, J=4.3, 8.7 Hz), 7.34 (1H, app. dt, J=2.6, 8.1 Hz), 4.56 (2H, d, J=6.3

Hz), 4.71 (2H, m), 3.43 (2H, m), 3.23 (3H, s), 3.04 (3H, s). HRMS: calc'd for $C_{20}H_{20}FN_3O_7S_2+1Na+=520.0625$, observed 520.0619.

EXAMPLE 11

1-ethyl-N-[4-fluoro-2-(methylthio)benzyl]-4-hydroxy-2-oxo-1,2-dihydro-1,5-naphthyridine-3-carboxamide

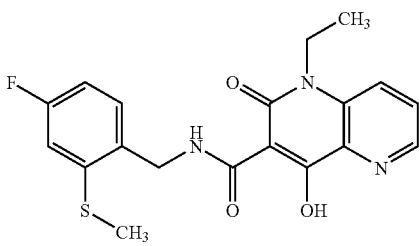

In a manner similar to that described in Examples 2 and 3, ethylamine (1.3 equivalent of a 2.0 molar solution in THF) was treated with 3-fluoro-2-cyanopyridine and then further derivatized to give the product.

$^1$H NMR (CDCl$_3$, 400 MHz) δ 10.60 (1H, bs), 8.71 (1H, d, J=4.3 Hz), 7.72 (1H, d, J=8.7 Hz), 7.61 (1H, dd, J=4.2, 8.7 Hz), 7.36 (1H, dd, J=6.0, 8.4 Hz), 6.96 (1H, dd, J=2.5, 9.5 Hz), 6.84 (1H, app. dt, J=2.5, 8.2 Hz), 4.67 (2H, d, J=5.9 Hz), 4.30 (2H, q, J=7.1 Hz), 2.52 (3H, s), 1.34 (3H, t, 7.1 Hz). HRMS: calc'd for $C_{19}H_{18}FN_3O_3S+1H=388.1126$, observed 388.1138.

EXAMPLE 12

1-ethyl-N-[4-fluoro-2-(methylsulfonyl)benzyl]-4-hydroxy-2-oxo-1,2-dihydro-1,5-naphthyridine-3-carboxamide

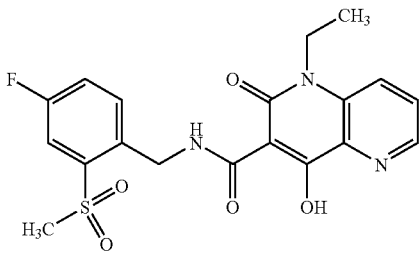

In a manner similar to that described in Examples 2 and 3, ethylamine (1.3 equivalents of a 2.0 molar solution in THF) was treated with 3-fluoro-2-cyanopyridine and then further derivatized to give the product.

$^1$H NMR (DMSO, 400 MHz) δ 10.86 (1H, bs), 8.65 (1H, d, J=3.7 Hz), 8.15 (1H, d, J=8.5 Hz), 7.79 (1H, dd, J=4.1, 8.6 Hz), 7.76-7.61 (3H, m), 4.94 (2H, d, J=5.0 Hz), 4.29 (2H, q, J=6.4 Hz), 3.41 (3H, s), 1.21 (3H, t, 6.8 Hz). HRMS: calc'd for $C_{19}H_{18}FN_3O_5S+1H=420.1024$, observed 420.1037. C, H, N calc'd for $C_{19}H_{18}FN_3O_5S+0.5$ EtoAc, C=54.42, H=4.70, N=9.24, observed C=54.7, H=4.92, N=9.24.

EXAMPLE 13

N-[4-fluoro-2-(methylsulfonyl)benzyl]-4-hydroxy-1-methyl-2-oxo-1,2-dihydro-1,5-naphthyridine-3-carboxamide

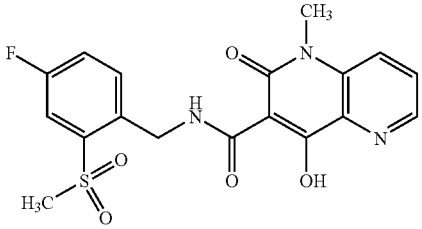

In a manner similar to that described in Examples 2 and 3, methylamine (1.3 equivalents of a 2.0 molar solution in THF) was treated with 3-fluoro-2-cyanopyridine and then further derivatized to give the product.

$^1$H NMR (DMSO, 400 MHz) δ 10.85 (1H, bs), 8.65 (1H, d, J=3.4 Hz), 8.10 (1H, d, J=8.6 Hz), 7.80 (1H, dd, J=4.2, 8.6 Hz), 7.74 (1H, dd, J=2.8, 8.6 Hz), 7.69 (1H, dd, J=5.5, 8.6 Hz), 7.69 (1H, app. dt, J=2.7, 8.4 Hz), 4.94 (2H, d, J=6.0 Hz), 3.63 (3H, s), 3.41 (3H, s). HRMS: calc'd for $C_{18}H_{16}FN_3O_5S+1H=406.0867$, observed 406.0868. C, H, N calc'd for $C_{19}H_{18}FN_3O_5S+0.05$ H$_2$O+0.2 TFA, C=51.5, H=3.83, N=9.79, found C=51.55, H=3.88, N=9.4.

EXAMPLE 14

N-(4-fluorobenzyl)-4-hydroxy-1-[2-(methylsulfinyl)ethyl]-2-oxo-1,2-dihydro-1,5-naphthyridine-3-carboxamide

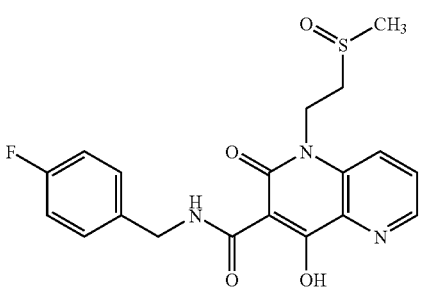

In a manner similar to that described in Examples 2 and 3, 2-(methylthio)ethanamine was treated with 3-fluoro-2-cyanopyridine and then further derivatized to give the product.

$^1$H NMR (CDCl$_3$, 400 MHz) δ 10.38 (1H, bs), 8.76 (1H, d, J=4.3 Hz), 8.06 (1H, d, J=8.7 Hz), 7.68 (1H, dd, J=4.2, 8.7 Hz), 7.34 (2H, dd, J=5.5, 8.3 Hz), 7.05 (2H, t, J=8.6 Hz), 4.76 (1H, m), 4.67 (1H, m), 4.63 (2H, d, J=5.7 Hz), 3.18 (1H, m), 3.05 (1H, m), 2.71 (3H, s). HRMS: calc'd for $C_{19}H_{18}FN_3O_4S+1H=404.1080$, observed 404.1073. C, H, N calc'd for $C_{19}H_{18}FN_3O_4S+0.55$ TFA, C=51.79, H=4.01, N=8.86, found C=51.70, H=3.90, N=8.86.

EXAMPLE 15

N-(4-fluorobenzyl)-4-hydroxy-1-[2-(methylsulfonyl)ethyl]-2-oxo-1,2-dihydro-1,5-naphthyridine-3-carboxamide

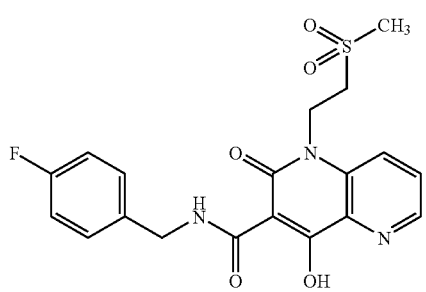

In a manner similar to that described in Examples 2 and 3, 2-(methylthio)ethanamine was treated with 3-fluoro-2-cyanopyridine and then further derivatized to give the product.

$^1$H NMR (CDCl$_3$, 400 MHz) δ 10.34 (1H, bs), 8.75 (1H, dd, J=1.1, 4.3 Hz), 7.92 (1H, d, J=8.8 Hz), 7.68 (1H, dd J=4.3, 8.7 Hz), 7.35 (2H, m), 7.07 (2H, t, J=8.7 Hz), 4.69 (2H, t, J=7.4 Hz), 4.63 (2H, d, J=5.8 Hz), 3.42 (2H, t, J=7.4 Hz), 3.03 (3H, s). HRMS: calc'd for C$_{19}$H$_{18}$FN$_3$O$_5$S+1H=420.1029, observed 404.1024. C, H, N calc'd for C$_{19}$H$_{18}$FN$_3$O$_5$S+0.1 TEA, C=53.53, H=4.23, N=9.75, found C=53.66,1H=3.81, N=9.47.

EXAMPLE 16

N-(4-fluorobenzyl)-4-hydroxy-1-(2-morpholin-4-ylethyl)-2-oxo-1,2-dihydro-1,5-naphthyridine-3-carboxamide

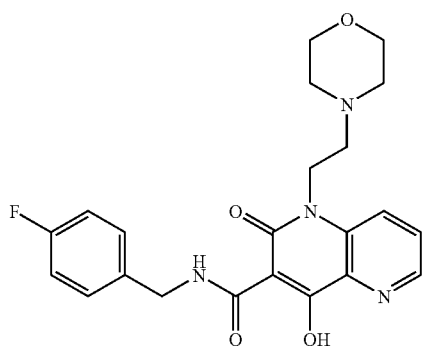

In a manner similar to that described for Examples 2 and 3, 2-morpholin-4-ylethanamine (Aldrich) was reacted with 3-fluoro-2-cyano pyridine and further derivatized to give the product.

$^1$H NMR (DMSO-d6, 400 MHz) δ 10.56 (1H, bs), 9.68 (1H, bs), 8.71 (1H, d, J=4.2 Hz), 8.17 (1H, d, J=9.0 Hz), 7.77 (1H, dd, J=4.2, 8.8 Hz), 7.43 (2H, m), 7.21(2H, m), 4.62 (4H, m), 4.01 (4H, m), 3.63 (2H, m), 3.43 (2H, m), and 3.21 (2H, m) ppm. APCI Exact Mass: Measured Mass [M+1]=427.1796, Theorectical Mass [M+1]=427.1776

EXAMPLE 17

N-(4-fluorobenzyl)-4-hydroxy-2-oxo-1-[2-(1H-1,2,4-triazol-1-yl)ethyl]-1,2-dihydro-1,5-naphthyridine-3-carboxamide, trifluoroacetic acid salt

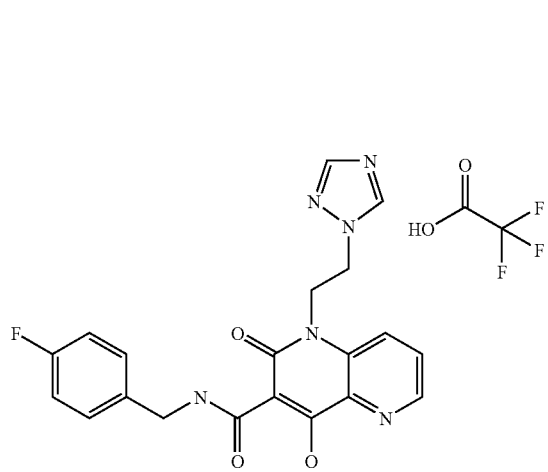

In a manner similar to that described for Examples 2 and 3, 2-(1H-1,2,4-triazol-1-yl)ethanaminium hydrogen sulfate (Chembridge Corp.) was reacted with 3-fluoro-2-cyano pyridine and further derivatized to give the product.

$^1$H NMR (DMSO-d$_6$, 400 MHz) δ 10.51 (1H, bs), 8.60 (1H, d, J=4.2 Hz), 8.45 (1H, s), 7.89 (1H, s), 7.79(1H, d, J=8.8 Hz), 7.66 (1H, dd, J=4.2, 8.8 Hz), 7.44 (2H, m), 7.21(2H, m), 4.64 (2H, t, J=5.68), 4.59 (2H, d, J=5.67), and 4.53 (2H, m) ppm. APCI Exact Mass: Measured Mass [M+Na]=431.1239, Theoretical Mass [M+Na]=431.1238

EXAMPLE 18

1-[2-(dimethylamino)-2-oxoethyl]-N-[4-fluoro-2-(methylsulfonyl)benzyl]-4-hydroxy-2-oxo-1,2-dihydro-1,5-naphthyridine-3-carboxamide

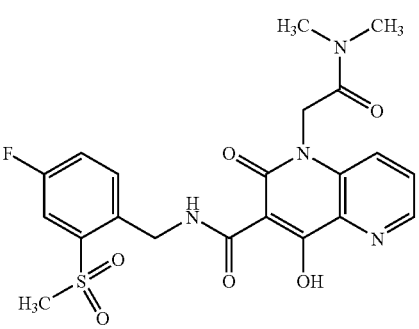

Step 1: Preparation of methyl 4-hydroxy-1-(2-methoxy-2-oxo-1,2-dihydro-1,5-naphthyridine-3-carboxylte

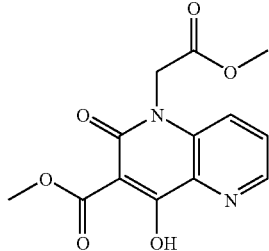

In a manner similar to that described in Example 2, glycine methyl ester hydrochloride was reacted with 3-fluoro-2-cyanopyridine. As described in Example 2, the resulting cyano compound was treated under Pinner conditions to give the ester, which was reacted with methyl 3-chloro-3-oxo propionate to give the product as a sticky orange solid.

$^1$H NMR (DMSO-d$_6$, 400 MHz) δ 8.62 (1H, d), 8.31 (1H, s), 8.04 (1H, d), 7.74 (1H, dd), 5.06 (2H, s), 3.79 (3H, s), 3.70 (3H, s) ppm.

Step 2: Preparation of methyl [3-({[4-fluoro-2-(methylthio)benzyl]amino}carbonyl)-4-hydroxy-2-oxo-1,5-naphthyridin-1(2H)-yl]acetate

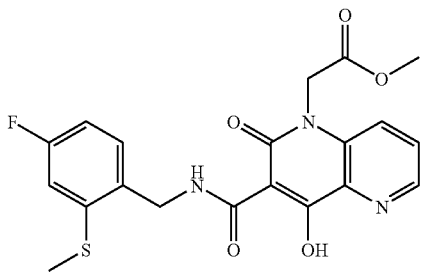

In a manner similar to that described in Example 2, methyl 4-hydroxy-1-(2-methoxy-2-oxo-1,2-dihydro-1,5-naphthyridine-3-carboxylate was treated with 1-[4-fluoro-2-(methylthio)phenyl]methanamine in EtOH at 80° C. for 48 hours. The reaction was cooled and the solid precipitate collected and washed with EtOH to give the product as a white solid.

ESMS: calc'd 431.4, observed 431.9 (M+1).

Step 3: Preparation of methyl [3-({[4-fluoro-2-(methylsulfonyl)benzyl]amino}carbonyl)-4-hydroxy-2-oxo-1,5-naphthyridin-1(2H)-yl]acetate

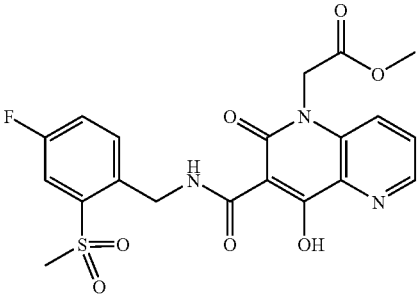

In a manner similar to that described in Example 3, methyl [3-({[4-fluoro-2-(methylthio)benzyl]amino}carbonyl)-4-hydroxy-2-oxo-1,5-naphthyridin-1(2H)-yl]acetate was treated with m-chloroperoxybenzoic acid and after purification on reverse phase HPLC was isolated as a light yellow solid.

$^1$H NMR (DMSO-d$_6$, 400 MHz) δ 10.58 (1H, bs), 8.66 (1H, d, J=4.0 Hz), 8.10 (1H, d, J=8.6 Hz), 7.78 (1H, dd, J=4.0, 8.4 Hz), 7.73 (1H, dd, J=2.6, 8.6 Hz), 7.67 (1H, dd, J=5.5, 8.7 Hz), 7.62 (1H, app. dt, J=2.6, 8.3 Hz), 5.13 (2H, bs), 4.92 (2H, d, J=5.9 Hz), 3.70 (3H, s), 3.4 (3H, s).

Step 4: Preparation of [3-({[4-fluoro-2-(methylsulfonyl)benzyl]amino}carbonyl)-4-hydroxy-2-oxo-1,2-dihydro-1,5-naphthyridin-1(2H)-yl]acetic acid

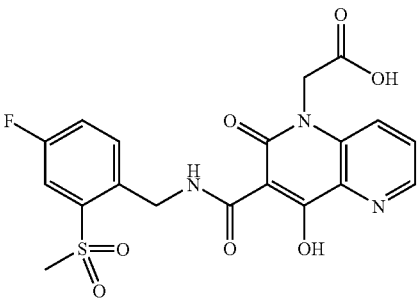

A suspension of methyl [3-({[4-fluoro-2-(methylsulfonyl)benzyl]amino}carbonyl)-4-hydroxy-2-oxo-1,5-naphthyridin-1(2H)-yl]acetate (77 mg, 0.166 mmol) in 3N NaOH (0.55 mL) was heated to reflux for one hour. The solution was poured into 10% KHSO$_4$ and extracted four times with EtOAc. The organic layer was dried over Na2SO4, filtered and concentrated to give the product as a white solid.

$^1$H NMR (DMSO-d$_6$, 400 MHz) δ 13.1 (1H, bs), 10.64 (1H, bs), 8.66 (1H, bs,), 8.07 (1H, d, J=8.6 Hz), 7.8 (1H, m), 7.74 (1H, m), 7.7 (1H, m), 7.62 (1H, m), 5.04 (2H, bs), 4.93 (2H, d, J=5.4 Hz), 3.41 (3H, s) ppm.

Step 5: Preparation of 1-[2-(dimethylamino)-2-oxoethyl]-N-[4-fluoro-2-(methylsulfonyl)benzyl]-4-hydroxy-2-oxo-1,2-dihydro-1,5-naphthyridine-3-carboxylate.

Dry DMP (0.5 mL) was saturated with dimethylamine gas and [3-({[4-fluoro-2-(methylsulfonyl)benzyl]amino}carbonyl)-4-hydroxy-2-oxo-1,2-dihydro-1,5-naphthyridin-1(2H)-yl]acetic acid (0.40 g, 0.089 mmol) and triethylamine (0.025 mL, 0.178 mmol), and BOP reagent (0.051 g, 0.116 mmol) were added. The reaction was stirred at room temperature, re-saturated with dimethylamine after 1 hour and stirred overnight. The crude reaction product was purified on reverse phase HPLC eluting with 5:95% acetonitrile/water (0.1% TFA) to 95:5% to give the product as a light yellow solid.

$^1$HNMR (DMSO-$d_6$, 400 MHz) δ 10.68 (1H, bs), 8.64 (1H, d, J=4.2 Hz), 7.94 (1H, d, J=8.8 Hz), 7.76-7.60 (4H, m), 5.19 (2H, m), 4.93 (2H, m), 3.40 (3H, s), 3.15 (3H, s), and 2.85 (3H, s) ppm. ESMS Exact Mass: $C_{21}H_{21}FN_4O_6S$ Measured Mass [M+1]=477.1215, Theorectical Mass [M+1]= 477.1239

EXAMPLE 19

N-[4-fluoro-2-(methylsulfonyl)benzyl]-4-hydroxy-2-oxo-1,2-dihydro-1,5-naphthyridine-3-carboxamide

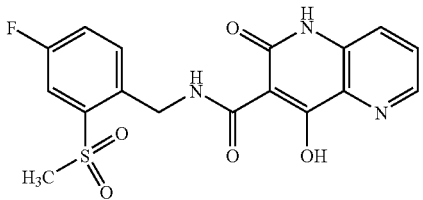

The compound was prepared in a manner similar to that described for Examples 1 and 3.

$^1$H NMR (DMSO-$d_6$, 400 MHz) δ 11.99 (1H, bs), 10.79 (1H, bs), 8.58 (1H, d, J=2.2 Hz), 7.77-7.68 (5H, m), 4.94 (2H, d, J=5.7 Hz), and 3.40 (3H, s) ppm. ESMS Exact Mass: Measured Mass [M+1]=392.0711, Theorectical Mass [M+1]= 392.0711

EXAMPLE 20

N-[4-fluoro-2-(methylsulfonyl)benzyl]-4-hydroxy-1-(2-methoxyethyl)-2-oxo-1,2-dihydro-1,5-naphthyridine-3-carboxamide

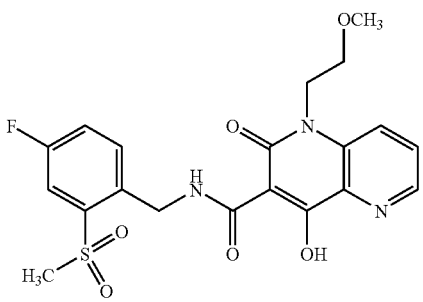

In a manner similar to that described in Examples 2 and 3, 2-(methoxyethyl)methanamine was reacted with 3-fluoro-2-cyanopyridine and then further derivatized to give the product.

$^1$H NMR (CDCl$_3$, 400 MHz) δ 10.88 (1H, bs), 8.67 (1H, d, J=4.3 Hz) 8.00 (1H, d, J=8.8 Hz), 7.79 (1H, m), 7.70 (1H, dd, J=5.2, 8.4 Hz), 7.57 (1H, m), 7.33 (1H, m) 4.98 (2H, d, J=6.22 Hz), 4.44 (2H, m), 3.73 (2H, m), 3.29 (3H, s), 3.25 (3H, s) ppm. ESMS Exact Mass: Measured Mass [M+1]= 450.1127, Theoretical Mass [M+1]=450.1135.

EXAMPLE 21

1-Benzyl-n-[4-fluoro-2-(methylsulfonyl)benzyl]-4-hydroxy-2-oxo-1,2-dihydro-1,5-naphthyridine-3-carboxamide

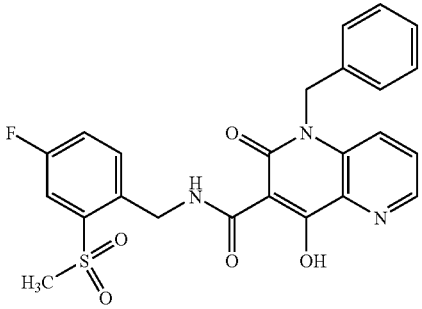

In a manner similar to that described in Examples 2 and 3, benzylamine was reacted with 3-fluoro-2-cyanopyridine and then further derivatized to give the product.

$^1$H NMR (CDCl$_3$, 400 MHz) δ 10.89 (1H, bs), 8.67 (1H, d, J=4.2 Hz) 7.77 (1H, dd, J=2.8, 8.2 Hz), 7.71 (1H, dd, 5.1, 8.6 Hz), 7.60 (1H, d, J=8.7 Hz), 7.46 (1H, dd, J=4.3, 8.7 Hz), 7.28-7.36 (4H, m), 7.15 (2H, d, J=7.14 Hz), 5.52 (2H, s), 5.00 (2H, d, J=6.2 Hz), 3.23 (3H, s)ppm. ESMS Exact Mass: Measured Mass [M+1]=482.1178, Theoretical Mass [M+1]= 482.1186.

EXAMPLE 22

1-{2-[[(dimethylamino)sulfonyl](methyl)amino]ethyl}-N-[4-fluoro-2-(methylsulfonyl)benzyl]-4-hydroxy-2-oxo-1,2-dihydro-1,5-naphthyridine-3-carboxamide

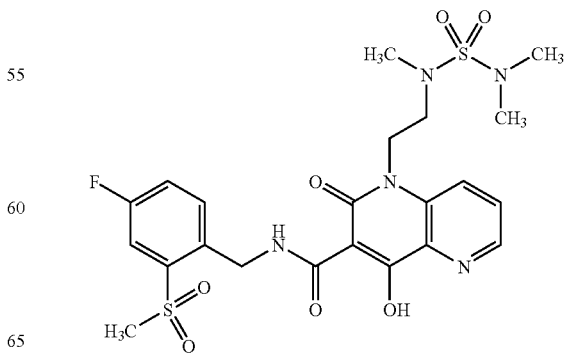

Step 1: Preparation of benzyl 2-[(2-cyanopyridin-3-yl)amino]ethyl(methyl)carbamate

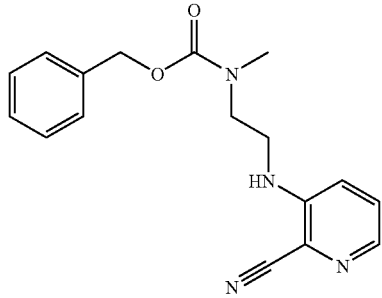

A solution of benzyl 2-(methylamino)ethylcarbamate (prepared as described in example 7, 14 g, 72.1 mmol) in DMSO (20 mL) was reacted with 3-fluoro-2-cyanopyridine (see example 2, 8 g, 65.5 mmol) in a pressure vessel at 85° C. overnight. The resulting mixture was diluted with CHCl3 (100 mL) and added to the top of a silica gel column (150 mm by 7 inches) packed with 20% EtOAc/Hexanes. The column was eluted with a gradient of 20% EtOAc/Hexanes to 100% EtOAc and the clean fractions combined and evaporated to give the product as a yellow oil.

$^1$H NMR (CDCl$_3$, 400 MHz) δ 7.97(1H, bs), 7.4-7.3 (5H, m), 7.15 (1H, m), 7.03 (1H, bs), 6.85 (1H, m), 5.17 (2H, s), 3.55 (2H, m), 3.40 (2H, m), 2.99 (3H, s) ppm.

Step 2: Preparation of methyl 3-{[2-(methylamino)ethyl]amino}pyridine-2-carboxylate

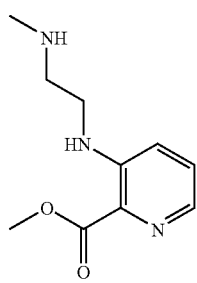

In a manner similar to that described in example 2, benzyl 2-[(2-cyanopyridin-3-yl)amino]ethylcarbamate (11.9 g, 38.3 mmol) was dissolved in MeOH and treated with HCl gas and water to give the ester. The reaction was concentrated, dissolved in MeOH and adsorbed to silica gel. The product was eluted with CHCl3 saturated with NH3, the fractions were collected and evaporated to give the product as a yellow oil that crystallized upon sitting.

$^1$H NMR (CDCl$_3$, 400 MHz) δ 8.0 (1H, dd, J=0.8,4.2 Hz), 7.88 (1H, bs), 7.27 (1H, dd, buried, J=4.2 Hz), 7.11 (1H, d, J=8.4 Hz), 3.96 (3H, s), 3.32 (2H, m), 2.90 (2H, m), 2.49 (3H, s) ppm.

Step 3: Preparation of methyl 3-[(2-{[(benzyloxy)carbonyl]amino}ethyl)amino]pyridine-2-carboxylate

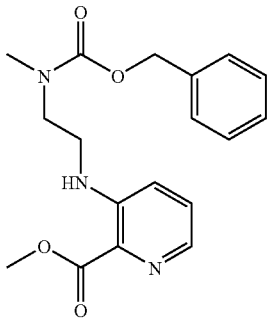

A solution of methyl 3-[(2-aminoethyl)amino]pyridine-2-carboxylate (3.9 g, 18.6 mmol) in CHCl$_3$ (25 mL) was treated with pyridine (3 mL, 37.3 mmol) then 1-{[(benzyloxy)carbonyl]oxy}pyrrolidine-2,5-dione (Aldrich, 5.57 g, 22.3 mmol) for ½ hr. The reaction was quenched with water and extracted three times with CHCl3. The organic layer was dried with Na$_2$SO$_4$, filtered and evaporated to give an oil. The crude was purified on silical gel using an ISCO normal phase system and eluting with a gradient of 50% to 90% EtOAc Hexanes. The clean fractions were combined to give the product as an oil.

$^1$H NMR (CDCl$_3$, 400 MHz) δ 8.0 (1H, bd, J=12.72 Hz), 7.84 (1H, bs), 7.36 (5H, bs), 7.26 (1H, bs), 7.02-6.95 (1H, m), 5.16 (2H, s), 3.94 (3H, s), 3.4-3.28 (4H, m), 3.0 (3H, s) ppm.

Step 4: Preparation of methyl 1-{2-[[(benzyloxy)carbonyl](methyl)amino]ethyl}-4-hydroxy-2-oxo-1,2-dihydro-1,5-naphthyridine-3-carboxylate

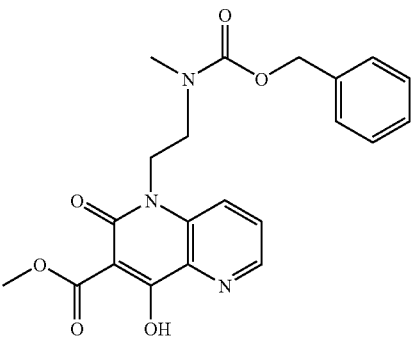

In a manner similar to that described for example 2, methyl 3-[(2-{[(benzyloxy)carbonyl]amino}ethyl)amino]pyridine-2-carboxylate was treated with NaH and methyl 3-chloro-3-oxopropionate. After aqueous workup, the resulting oil was triturated with ether and CH$_2$Cl$_2$ to give the product as an off-white solid. More product was obtained from reverse phase HPLC purification of the mother liquor.

$^1$H NMR (DMSO-d6, 400 MHz) δ 8.23 (1H, m), 7.5 (1H, m), 7.4-7.25 (5H, m), 7.1 (1H, m), 5.06 (1H, s), 4.99 (1H, s), 4.2 (2H, bs), 3.6 (3H, s), 3.38 (2H, bs), 2.86 (3H, s) ppm.

Step 5: Preparation of 4-fluoro-2-(methylthio)benzonitrile.

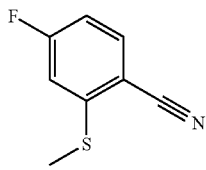

2,4-difluorobenzonitrile (2.0 g, 14.38 mmol) and thiomethoxide (1.02 g, 14.38 mmol) were placed in an oven dried 100 mL round bottom flask fitted with a reflux condenser. Toluene (40 mL) was added and the reaction solution was put under an atmosphere of Argon. The reaction was heated to 90° C. over 48 hours. The crude reaction was cooled and concentrated in vacuo. The residue was taken up in methylene chloride and extracted with water. The organic phase was dried (MgSO$_4$), filtered and concentrated to afford a white solid. The solid was dissolved in a minimal amount of methylene chloride and purified on an ISCO column (110 g silica) with a gradient of 100% to 80% hexanes/20% ethylacetate over 15 min at 45 ml/min, then 20% EtOAc/ 80% Hexanes for 5 min. The collected fractions were evaporated in vacuo to afford the desired material in a 7.5:1 ratio 4-fluoro-2-(methylthio)benzonitrile:2-fluoro-4-(methylthio)benzonitrile. The white solid was carried on to the next step without further purification.

$^1$H NMR (CDCl$_3$, 400 MHz, major regioisomer) δ 7.56 (1H, dd, J=5.58, 8.51 Hz), 6.95 (1H, dd, J=2.38, 9.34 Hz), 6.88 (1H, dt, J=2.38, 8.24 Hz), 2.54 (3H, s) ppm. EI HRMS exact mass calc'd for C$_8$H$_6$FNS 167.0203, found 167.0205.

Step 6: Preparation of 4-fluoro-2-(methylsulfonyl)benzonitrile.

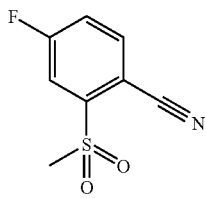

4-fluoro-2-(methylthio)benzonitrile (1.59 g, 9.51 mmol, 7.5:1 mixture of regioisomers from Step 1) was dissolved in methylene chloride (50 mL) and 3-chloroperoxybenzoic acid (60% by weight, 4.6 g, 16 mmol) was added. The reaction was put under an atmosphere of Argon and stirred overnight at ambient temperature. The reaction was quenched with saturated aqueous sodium bicarbonate (2×100 mL). The organic phase still contained some 3-chloroperoxybenzoic acid by LCMS analysis so 1 mL DMSO was added and stirred for 1 hour. The organic phase was then extracted again with saturated aqueous sodium bicarbonate (100 mL), dried (MgSO4), filtered and concentrated to afford the desired material as a 7:1 ratio of 4-fluoro-2-(methylsulfonyl)benzonitrile:2-fluoro-4-(methylsulfonyl)-benzonitrile. Selective crystallization from methanol, filtration and drying in vacuo afforded the desired 4-fluoro-2-(methylsulfonyl)benzonitrile as white crystals.

$^1$H NMR (CDCl$_3$, 400 MHz, major regioisomer) δ 7.93 (1H, dd, J=4.77, 8.51 Hz), 7.90 (1H, dd, J=2.36, 7.70 Hz), 7.45 (1H, ddd, J=2.56, 7.24, 8.47 Hz), 3.28 (3H, s) ppm. EI HRMS exact mass calc'd for C$_8$H$_6$FNSO$_2$ 199.0103, found 199.0103.

Step 7: Preparation of 1-[4-fluoro-2-(methylsulfonyl)phenyl]methanaminium chloride

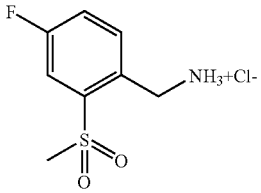

4-fluoro-2-(methylsulfonyl)benzonitrile (5.6 g, 28.11 mmol) was added to a dry Parr bottle. Methanol (50 mL) and conc HCl (10 mL) were added and the reaction solution put under an Argon atmosphere. 10% Pd/C (1 gram) was added and the reaction vessel placed on a Parr hydrogenation apparatus. The reaction was placed under an atmosphere of H$_2$ (50 psi) and shaken overnight. After overnight the ratio of starting material to product was 50:50. The reaction was filtered through celite and concentrated slightly. Conc. HCl (10 mL) and 10% Pd/C (1 gram) were added and the reaction was again put under H$_2$ (50 psi). The reaction was again shaken overnight. The crude reaction was filtered through celite and concentrated to afford the desired material as a white solid.

$^1$H NMR (CDCl$_3$, 400 MHz) δ 7.86 (1H, dd, J=2.74, 8.24 Hz), 7.74 (1H, dd, J=5.03, 8.51 Hz), 7.57 (1H, dt, J=2.75, 8.15 Hz), 4.45 (2H, s), 3.27 (3H, s) ppm. MS calc'd for C$_8$H$_{10}$FNO$_2$S 203 (MH+), found 204. EI HRMS exact mass calc'd for C$_8$H$_{10}$FNO$_2$S 203.0410, found 203.0416. C, H, N calc'd for C$_8$H$_{10}$FNO$_2$S 1.1 HCl % C, 39.49, % H, 4.6, % N, 5.76, found % C, 39.50, % H, 4.34, % N, 5.56.

Step 8: Preparation of benzyl 2-[3-({[4-fluoro-2-(methylsulfonyl)benzyl]amino}carbonyl)-4-hydroxy-2-oxo-1,5-naphthyridin-1(2H)-yl]ethyl(methyl)carbamate

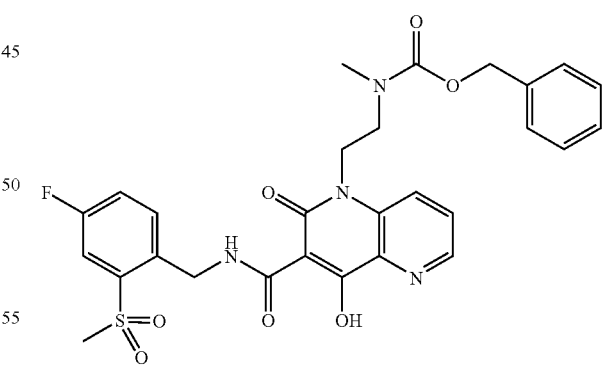

A solution of methyl 1-{2-[[(benzyloxy)carbonyl](methyl)amino]ethyl}-4-hydroxy-2-oxo-1,2-dihydro-1,5-naphthyridine-3-carboxylate (0.5 g, 1.21 mmol) in MeOH (6 mL) was treated with Hunig's base (0.33 mL, 1.82 mmol) and 1-[4-fluoro-2-(methylsulfonyl)phenyl]methanaminium chloride (0.35 g, 1.46 mmol) and heated in a sealed reaction vessel at 80 degrees C. After overnight, an additional 0.5 equivalents of the amine and 1.5 equivalents of Hunig's base was added and the reaction heated until HPLC showed the starting material gone. The reaction was cooled and the solids that percipitated were collected by filtration to give pure product.

$^1$H NMR (DMSO-d6, 400 MHz) δ 11.2 (1H, bs), 8.3 (1H, bd), 7.9 (1H, m), 7.85 (1H, m), 7.65 (2H, m), 7.55(1H, m 7.48 (1H, m), 7.3 (4H, m), 7.1 (1H, m), 5.05 (1H, s), 4.95 (1H, s), 4.8(2H, bs), 4.2 (2H, bs), 3.4 (3H, s), 3.4 (3H, s), 2.88 (2H, bs) ppm.

Step 9: Preparation of N-[4-fluoro-2-(methylsulfonyl)benzyl]-4-hydroxy-1-[2-(methylamino)ethyl]-2-oxo-1,2-dihydro-1,5-naphthyridine-3-carboxamide

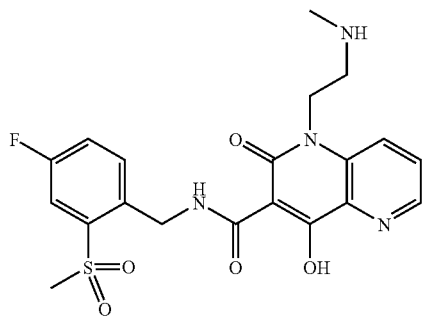

A solution of benzyl 2-[3-({[4-fluoro-2-(methylsulfonyl)benzyl]amino}carbonyl)-4-hydroxy-2-oxo-1,5-naphthyridin-1(2H)-yl]ethyl(methyl)carbamate (0.55 g, 0.94 mmol) in MeOH (10 mL) in a pressure tube was cooled to −78 degrees C. and saturated with HCl gas. The volume in the flask visibly increased. The reaction was allowed to warm to room temperature overnight, then cooled to −78 degrees C. and vented. The reaction was transferred to a round bottom flask and the solvents removed under vacuum. The reaction was suspended in toluene and evaporated to give the product as a solid.

$^1$H NMR (DMSO-d6, 400 MHz) δ 10.7 (1H, m), 9.2-9.1 (1H, m), 8.67 (1H, d, J=4.2 Hz), 8.40 (1H, d, J=8.5 Hz), 7.80 (1H, dd, J=4.3, 8.7 Hz), 7.6-7.2 (2H, m), 7.63 (1H, app t, J=2.7, 8.5 Hz), 4.95 (2H, d, J=5.8 Hz), 4.6 (2H, m), 3.41 (3H, s), 3.16 (2H, bs), 2.56 (3H, bs) ppm.

Step 10: Preparation of 1-{2-[[(dimethylamino)sulfonyl](methyl)amino]ethyl}-N-[4-fluoro-2-(methylsulfonyl)benzyl]-4-hydroxy-2-oxo-1,2-dihydro-1,5-naphthyridine-3-carboxamide.

A solution of N-[4-fluoro-2-(methylsulfonyl)benzyl]-4-hydroxy-1-[2-(methylamino)ethyl]-2-oxo-1,2-dihydro-1,5-naphthyridine-3-carboxamide (0.07 g, 0.16 mmol) in DM (3 mL) was treated with dimethylsulfamoyl chloride (0.44 g, 0.31 mmol) and Hunig's base (0.11 mL, 0.62 mmol) and stirred at room temperature for several hours. Additional dimethylsulfamoyl chloride was added after an hour. The reaction was injected directly onto a reverse phase HPLC column and the compound collected after eluting with a gradient of 95% water/acetonitrile to 5% water acetonitrile. The fractions were combined, evaporated and the crude oil was lyophilized from acetonitrile and water to give the product as a fluffy solid.

$^1$H NMR (CDCl$_3$, 400 MHz) δ 10.77 (1H, m), 8.72 (1H, d, J=4.2 Hz), 8.07 (1H, d, J=8.6 Hz), 7.77 (1H, dd, J=2.7, 8.2 Hz), 7.70 (1H, dd, J=5.1, 13.3 Hz), 7.66 (1H, dd, J=4.3, 8.8 Hz), 7.33 (1H, app dt, J=2.7, 8.0 Hz), 4.98 (2H, d, J=6.2 Hz), 4.48 (2H, m), 3.45 (2H, m), 3.24 (3H, s), 2.94 (3H, s), 2.79 (6H, s) ppm. ESMS Exact Mass: Measured Mass [M+1]=556.1325, Theoretical Mass [M+1]=556.1330.

EXAMPLE 23

N-[4-fluoro-2-(methylsulfonyl)benzyl]-4-hydroxy-1-[2-(4-methylpiperazin-1-yl)-2-oxoethyl]-2-oxo-1,2-dihydro-1,5-naphthyridine-3-carboxamide

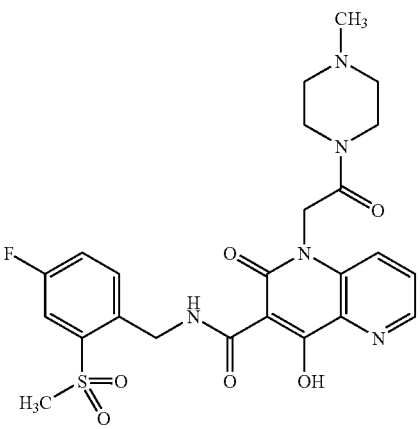

The compounds was prepared in a manner similar to that described for Example 18.

$^1$H NMR (DMSO-d6, 400 MHz) δ 10.6 (1H, bs), 9.88 (1H, bs), 8.65 (1H, d, J=4.2 Hz), 7.94 (1H, d, J=8.97 Hz), 7.8-7.7 (3H, m), 7.64 (1H, m), 5.4 (1H, d, J=16.4 Hz), 5.16 (1H, d, J=16.4 Hz), 4.91 (2H, d, J=6.0 Hz), 4.3 (2H, m), 3.5 (8H, m), 3.2 (1H, m), 3.0 (1H, m), 2.88 (3H, s). ESMS Exact Mass: Measured Mass [M+1]=532.1652, Theoretical Mass [M+1]=532.1661.

EXAMPLE 24

N-[4-fluoro-2-(methylsulfonyl)benzyl]-4-hydroxy-1-(2-morpholin-4-yl-2-oxoethyl)-2-oxo-1,2-dihydro-1,5-naphthyridine-3-carboxamide

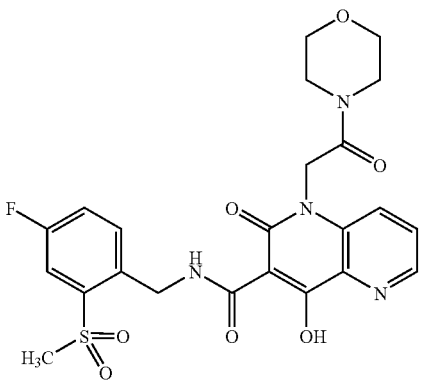

The compounds was prepared in a manner similar to that described for Example 18.

1H NMR (DMSO-d6, 400 MHz) δ 10.68 (1H, m), 8.64 (1H, d, J=4.2 Hz), 7.93 (1H, d, J=8.6 Hz), 7.78-7.59 (4H, m), 5.23 (2H, s), 4.92 (2H, d, J=6.2 Hz), 3.7 (2H, bs), 3.6-3.4 (6H, m), 3.40 (3H, s) ppm. ESMS Exact Mass: Measured Mass [M+1]=519.1338, Theoretical Mass [M+1]=519.1344.

EXAMPLE 25

N-[4-fluoro-2-(methylsulfonyl)benzyl]-1-{2-[[(dimethylamino)carbonyl](methyl)amino]ethyl}-4-hydroxy-2-oxo-1,2-dihydro-1,5-naphthyridine-3-carboxamide

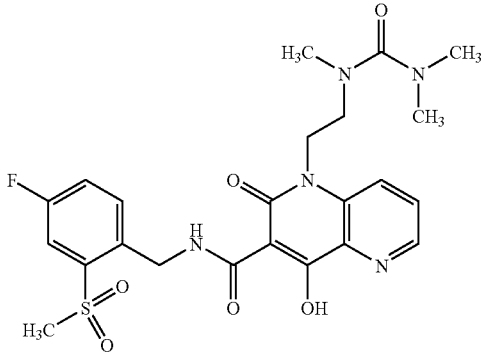

The compound was prepared in a manner similar to that described for Example 22, using N-[4-fluoro-2-(methylsulfonyl)benzyl]-4-hydroxy-1-[2-(methylamino)ethyl]-2-oxo-1,2-dihydro-1,5-naphthyridine-3-carboxamide and N,N-dimethylcarbamoyl chloride.

$^1$H NMR (CDCl$_3$, 400 MHz) δ 10.8 (1H, m), 8.72 (1H, d, J=3.74 Hz) 8.42 (1H, d, J=8.7 Hz), 7.77 (1H, dd, J=2.7, 8.1 Hz), 7.71(2H, m), 7.33 (1H, app t, J=2.7, 8.1 Hz), 4.87 (2H, d, J=6.3 Hz), 4.49 (2H, m), 3.35 (2H, m), 3.25 (3H, s), 3.02 (3H, s), 2.85 (6H, s). ESMS Exact Mass: Measured Mass [M+1]=520.1642, Theoretical Mass [M+1]=520.1661.

EXAMPLE 26

1-Benzyl-N-{4-fluoro-2-[(methylamino)carbonyl]benzyl}-4-hydroxy-2-oxo-1,2-dihydro-1,5-naphthyridine-3-carboxamide

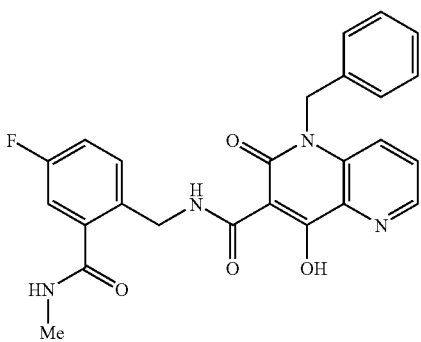

Step 1: Methyl 2-(bromomethyl)-5-fluorobenzoate

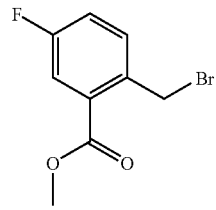

With no precautions to maintain a dry atmosphere, methyl 5-fluoro-2-methylbenzoate (Maybridge, 5 g, 29.7 mmole) was dissolved in CCl4 (50 mL). N-bromosuccinimide (5.82 g, 32.7 mmol) and benzoyl peroxide (0.36 g, 1.48 mmole) were added and the reaction brought to reflux overnight. An additional 0.3 eq of NBS and 0.01 eq of benzoyl peroxide was added and the reaction refluxed for 4 hrs, then cooled, filtered and concentrated. The residue was chromatographed on silica eluting with a gradient of 0-10% EtOAc/Hexanes. The fractions were collected to give the product, which was a mixture of mono and bis-brominated materials, as a clear oil.

$^1$H NMR (CDCl$_3$, 400 MHz, major product peaks) δ 7.67 (1H, dd, J=2.8, 9 Hz), 7.45 (1H, dd, J=5.4, 9 Hz), 7.20 (1H, m), 4.93 (2H, s), 3.95 (3H, s) ppm.

Step 2: Methyl 2-{[bis(tert-butoxycarbonyl)amino]methyl}-5-fluorobenzoate

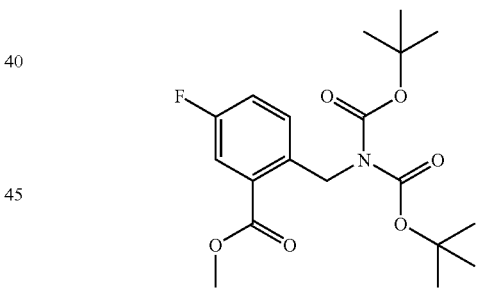

In a dry flask under nitrogen, di-tert-butyl iminodicarboxylate (Aldrich, 3.86 g, 17.8 mmol) was dissolved in dry DMF (5 mL) and treated with NaH (60% dispersion in oil, 0.71 g, 17.8 mmol). After the evolution of gas had ceased, Methyl 2-(bromomethyl)-5-fluorobenzoate (4 g, 16.2 mmole) dissolved in DMF (5 mL) was added. An additional 5 mL of DMF was added to aid stirring. The reaction was stirred for 2 hrs, then partitioned between water and EtOAc. The organic layer was dried with Na2SO4, filtered and concentrated and the residue was purified on silica eluting first with toluene, then with a gradient of 0-5% MeOH/CHCl3. The impure product thus obtained was re-chromatographed on silica eluting with a gradient of 0-30% EtOAc/Hexanes. The product was obtained as a clear oil.

$^1$H NMR (DMSO, 400 MHz,) δ 7.63 (1H, dd, J=2.8, 9.4 Hz), 7.52 (1H, m), 7.20 (1H, dd, J=5.3, 8.7 Hz), 4.98 (2H, s), 3.86 (3H, s), 1.38 (s, 18H) ppm.

Step 3: Preparation of tert-butyl 4-fluoro-2-[(methylamino)carbonyl]benzylcarbamate

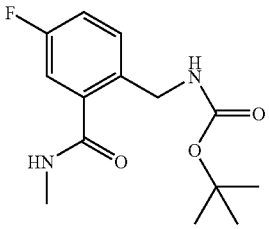

A solution of methyl 2-{[bis(tert-butoxycarbonyl)amino]methyl}-5-fluorobenzoate (5.0 g, 13.04 mmol) in toluene (40 mL) was treated with methyl amine gas at −78° C. until the solution was saturated. The reaction contents were then placed into a steel bomb and heated to 70° C. overnight. After cooling, the reaction was concentrated and then the solids were triturated with ether. The resulting solids were collected by vacuum filtration. As a result of the relatively harsh reaction conditions one of the BOC protecting groups was removed from the molecule.

$^1$H NMR (CDCl$_3$, 400 MHz) δ 7.41 (1H, dd, J=5.6, 8.3 Hz), 7.14-7.06 (2H, m), 6.64 (1H, bs), 5.69 (1H, bs), 4.26 (2H, d, J=6.3 Hz), 2.98 (3H, d, J=4.8 Hz), 1.41 (9H, s) ppm.

Step 4: Preparation of {4-fluoro-2-[(methylamino)carbonyl]phenyl}methanaminium chloride

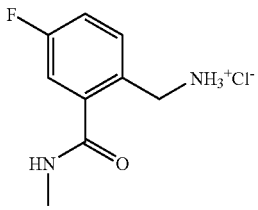

A solution of tert-butyl 4-fluoro-2-[(methylamino)carbonyl]benzylcarbamate (2.59 g, 9.17 mmol) in EtOAc (75 mL) was cooled to −78° C. After cooling solids precipitated out of the solution. HCl gas was added to the suspension until it reached saturation at which time the reaction became homogenous. After adding the HCl gas the dry ice bath was replaced with an ice water bath and the reaction was stirred for 10 minutes at 0° C. The solution was concentrated slowly and then redissolved in EtOAc and this was repeated two more times. The resulting solids were then triturated from EtOAc and fluffy white solids were collected by vacuum filtration.

$^1$H NMR (DMSO, 400 MHz) δ 8.82 (1H, d, J=4.2 Hz), 8.34 (3H, bs), 7.64 (1H, dd, J=5.6, 8.5 Hz), 7.49-7.41 (2H, m), 4.04 (2H, s), 2.80 (3H, d, J=4.5 Hz) ppm.

The above compound ({4-fluoro-2-[(methylamino)carbonyl]phenyl}methanaminium chloride) may also be prepared in other ways, one of which is the following: 4-fluoro-2-iodo-1-methylbenzene (Maybridge) may be brominated as described for step 1 in the above scheme to give 1-(bromomethyl)-4-fluoro-2-iodobenzene, and then treated with di-tert-butyl iminodicarboxylate to give di(tert-butyl) 4-fluoro-2-iodobenzylimidodicarbonate. This iodide can then be carbonylated by heating it under pressure with carbon monoxide, dppf, Pd(OAc)$_2$, an amine base like diisopropylethylamine and a great excess of methylamine in a solvent like DMF to give di(tert-butyl) 4-fluoro-2-[(methylamino)carbonyl]benzylimidodicarbonate containing some mono (tert-butyl) imidodicarbonated material. This mixture can then be treated with HCl gas in a solvent like Ethyl Acetate at cold temperature to remove the (tert-butyl) imidodicarbonate group(s), giving {4-fluoro-2-[(methylamino)carbonyl]phenyl}methanaminium chloride.

Step 5: Preparation of methyl 4-hydroxy-2-oxo-1,2-dihydro-1,5-naphthyridine-3-carboxylate (bis sodium salt)

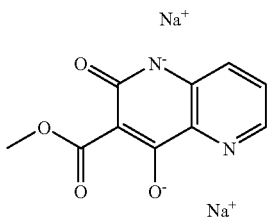

To a solution of methyl 3-[(3-methoxy-3-oxopropanoyl)amino]pyridine-2-carboxylate (7.3 g, 29.9 mmol, prepared as described in example 1) in anhydrous TBF (100 mL) was added solid sodium methoxide (3.9 g, 72.4 mmol) at 0° C. Immediately following the addition of the sodium methoxide, solids crashed out of the solution. The ice bath was then removed and the suspension was stirred for an additional 0.5 hours. The suspension was then filtered through a medium porosity filtration funnel to afford yellow solids.

$^1$NMR (D$_2$O, 400 MHz) δ 8.17 (1H, d, J=4.4 Hz), 7.38 (1H, d, J=8.4 Hz), 7.26 (1H, dd, J=4.4, 8.4 Hz), 3.72 (3H, s) ppm.

Step 6: Preparation of methyl 1-benzyl-4-(benzyloxy)-2-oxo-1,2-dihydro-1,5-naphthyridine-3-carboxylate

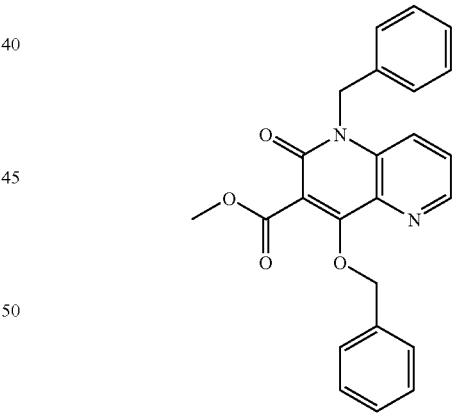

To a solution of the sodium salt of methyl 4-hydroxy-2-oxo-1,2-dihydro-1,5-naphthyridine-3-carboxylate (2.0 g, 7.57 mmol) in water (50 mL) was added a solution of benzyl bromide (3.89 g, 22.72 mmol) in methylene chloride (50 mL). To the biphasic solution was then added tetrabutylammonium bromide (1.2 g, 3.79 mmol) and the reaction was sealed and heated to 50° C. After stirring overnight the reactions was cooled and the two layers were separated. The aqueous layer was extracted one time with methylene chloride and the combined organics were dried over sodium sulfate, filtered and concentrated. The crude mixture was separated by normal phase chromatography using an Isco 120 gram silica gel cartridge with a 50 minute gradient running at 40 mL/min. of 10% to 60% EtOAc/hexanes. The tubes containing the desired product were concentrated and taken on to the next step.

$^1$NMR (CDCl3, 400 MHz) δ 8.55 (1H, m), 7.59 (1H, d, J=8.7 Hz), 7.48 (2H, d, J=7.3 Hz), 7.37-7.16 (9H, m), 5.69 (2H, s), 5.46 (2H, s), 3.87 (3H, s) ppm. MS calc'd for $C_{24}H_{20}N_2O_4$ 400(M), found 401 (MH+).

Step 7: Preparation of 1-benzyl-4-(benzyloxy)-2-oxo-1,2-dihydro-1,5-naphthyridine-3-carboxylic acid

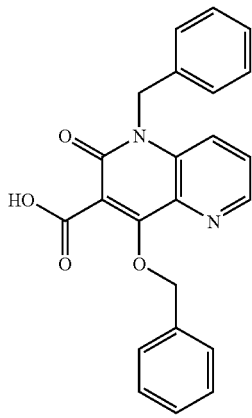

To a solution of methyl 1-benzyl-4-(benzyloxy)-2-oxo-1,2-dihydro-1,5naphthyridine-3-carboxylate (0.65 g, 1.62 mmol) in THF (20 mL) was added sodium hydroxide (16.2 mL, 1 N) and the solution was heated to 80° C. and after 1.5 hours the reaction was completed. The reaction was allowed to cool and then the THF was removed leaving the product in water. The water was acidified with 1N HCl to adjust the pH to 3 and the resulting crude solids were collected by vacuum filtration and taken on as is.

MS calc'd for $C_{23}H_{18}N_2O_4$ 386(M), found 387 (MH+).

Step 8: Preparation of 1-benzyl-4-(benzyloxy)-N-{4-fluoro-2-[(methylamino)carbonyl]benzyl}-2-oxo-1,2-dihydro-1,5-naphthyridine-3-carboxamide

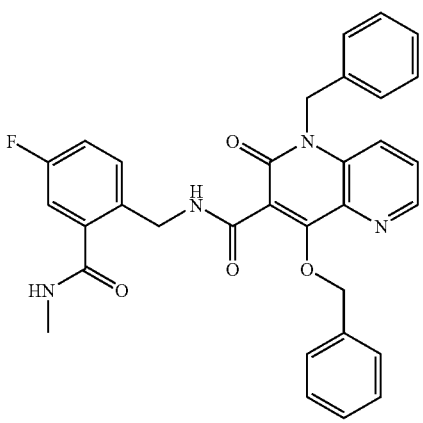

To a solution of 1-benzyl-4-(benzyloxy)-2-oxo-1,2-dihydro-1,5-naphthyridine-3-carboxylic acid (0.15 g, 0.39 mmol) in DMF (4 mL) was added HOAT (0.26 g, 1.94 mmol) and EDC (0.07 g, 0.47 mmol). The solution was stirred for 10 minutes at which time EDC (0.036 g, 0.23 mmol), {4-fluoro-2-[(methylamino)carbonyl]phenyl}methanaminium chloride (0.108 g, 0.47 mmol), and DIEA (0.10 g, 0.78 mmol) were added. The reaction was then stirred at room temperature overnight at which time the solution was purified by preparative reverse phase HPLC eluting with a gradient of 5-95% acetonitrile/water (0.1% TFA). The fractions that contained the desired product were concentrated. Note that during the prep des-O-benzyl product was also obtained. The mixture was taken on to the next step.

$^1$NMR (CDCl3, 400 MHz) δ 8.59 (1H, d, J=3.9 Hz), 7.69 (1H, t, J=5.7 Hz), 7.59 (2H, d, J=8.3 Hz), 7.50 (2H, dd, J=5.5, 8.5 Hz), 7.40 (1H, dd, J=4.4, 8.6 Hz), 7.37-7.28 (6H, m), 7.18-7.12 (4H, m), 7.03 (1H, dt, J=2.7, 8.3 Hz), 5.23 (2H, s), 5.48 (2H, s), 4.59 (2H, d, J=5.8 Hz), 2.94 (3H, d, J=4.6 Hz) ppm. MS calc'd for $C_{32}H_{27}FN_4O_4$ 550(M), found 551 (MH+).

Step 9: Preparation of sodium 1-benzyl-3-[({4-fluoro-2-[(methylamino)carbonyl]benzyl}amino)carbonyl]-2-oxo-1,2-dihydro-1,5-naphthyridin-4-olate To a solution of 1-benzyl-4-(benzyloxy)-N-{4-fluoro-2[(methylamino)carbonyl]benzyl}-2-oxo-1,2-dihydro-1,5-naphthyridine-3-carboxamide (0.06 g, 0.11 mmol) in methylene chloride (3 mL) was added TFA (1 mL) The reaction was stirred for 5 minutes at room temperature and then concentrated. The residue was redissolved in a minimum of DMF and purified by preparative reverse phase BPLC eluting with a gradient of 5-95% acetonitrile/water (0.1% TFA). The fractions that contained the desired product were concentrated. The solids were dissolved in a 50:50 mixture of $CH_3CN$/acetone followed by the addition of 1 N NaOH (0.109 mL). The solution was stirred for 0.5 hours and then concentrated to afford yellow solids.

$^1$NMR (DMSO, 400 MHz) δ 11.20 (1H, d, J=5.5 Hz), 8.68 (1H, d, J=4.2 Hz), 8.28 (1H, d, J=5.8 Hz), 7.51-7.47 (2H, m), 7.23 (1H, dd, J=4.2, 8.4 Hz), 7.29-7.16 (7H, m), 5.38 (2H, bs), 4.53 (2H, d, J=5.8 Hz), 2.78 (3H, d, J=4.4 Hz) ppm. High resolution MS calc'd for $C_{25}H_{21}FN_4O_4$ 461.1620(MH+), found 461.1619 (MH+).

EXAMPLE 27

N-[4-Fluoro-2-(methylsulfonyl)benzyl]-4-hydroxy-2-oxo-1-(2-oxo-2-thiomorpholin-4-ylethyl)-1,2-dihydro-1,5-naphthyridine-3-carboxamide

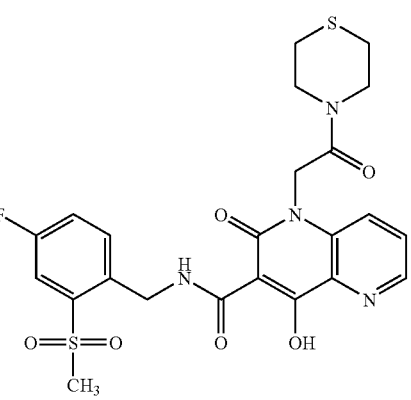

The compound was prepared in a manner similar to that described in Example 18 and lyophilized from dioxane to give the product as an off-white solid.

$^1$H NMR (DMSO, 400 MHz) δ 10.6 (1H, bs), 8.65 (1H, d, J=4.2 Hz), 7.94 (1H, d, J=8.6 Hz), 7.8-7.6 (4H, m), 5.22 (2H, bs), 4.93 (2H, bd, J=5.1 Hz), 3.86 (2H, bs), 3.8-3.6 (2H, bs), 3.57 (3H, s), 2.8 (2H, bs), 2.6 (2H, bs) ppm. MS calc'd for $C_{23}H_{23}FN_4O_6S_2$ 534 (M), found 534.9 (MH+) Low Res MS Electrospray.

EXAMPLE 28

Oral Compositions

As a specific embodiment of an oral composition of a compound of this invention, 50 mg of compound of Example 1 is formulated with sufficient finely divided lactose to provide a total amount of 580 to 590 mg to fill a size 0 hard gelatin capsule. Encapsulated oral compositions containing any one of the compounds of Examples 2-27 can be similarly prepared.

EXAMPLE 29

HIV Integrase Assay: Strand Transfer Catalyzed by Recombinant Integrase

Assays for the strand transfer activity of integrase were conducted in accordance with the method described in Example 193 of WO 02/30930 for recombinant integrase. Representative compounds of the present invention exhibit inhibition of strand transfer activity in this assay. For example, the compounds prepared in Examples 1-27 were tested in the integrase assay and all were found to have $IC_{50}$'s less than 0.5 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 30

Assay for Inhibition of HIV Replication

Assays for the inhibition of acute HIV infection of T-lymphoid cells were conducted in accordance with Vacca, J. P. et al., (1994), Proc. Natl. Acad. Sci. USA 91, 4096. Representative compounds of the present invention exhibit inhibition of I-UV replication in this assay. For example, the compounds prepared in Examples 1-27 were tested in the present assay and all were found to have $IC_{95}$'s less than 5 micromolar.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of Formula (I):

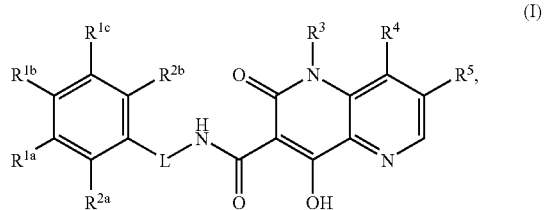

wherein L is a linker connecting the carbon atom of the phenyl ring to the nitrogen of the —NH— moiety, wherein L is
(i) a single bond,
(ii) —($C_{1-6}$ alkyl)-, which is optionally substituted with —C(=O)N($R^aR^b$),
(iii) —($C_{0-3}$ alkyl)-C=C—($C_{1-3}$ alkyl)-, or
(iv) —($C_{0-3}$ alkyl)-C≡C—($C_{1-3}$ alkyl)-;
$R^{1a}$, $R^{1b}$, and $R^{1c}$ are each independently —H, halogen, —$C_{1-6}$ alkyl, or —$C_{1-6}$ haloalkyl;
$R^{2a}$ and $R^{2b}$ are each independently:
(1) —H,
(2) —$C_{1-6}$ alkyl, optionally substituted with one or more substituents each of which is independently halogen, —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^a$, —$OCO_2R^a$, —S(O)$_nR^a$, —$SO_2N(R^aR^b)$, —N($R^a$)C(=O)$R^b$, —N($R^a$)$CO_2R^b$, —N($R^a$)$SO_2R^b$, or —N($R^a$)$SO_2$N($R^aR^b$),
(3) —$C_{1-6}$ alkyl substituted with one substituent which is —$C_{3-8}$ cycloalkyl, aryl, or heteroaryl, wherein:
   (a) the cycloalkyl is optionally substituted with one or more substituents each of which is independently halogen, —OH, —$C_{1-6}$ alkyl, —$C_{1-6}$ alkyl-O—$C_{1-6}$ alkyl, —$C_{1-6}$ haloalkyl, —O—$C_{1-6}$ alkyl, —O—$C_{1-6}$ haloalkyl, or phenyl;
   (b) the aryl is an aromatic carbocyclic ring or an aromatic carbocyclic fused ring system, wherein the aryl is optionally substituted with one or more substituents each of which is independently halogen, —OH, —$C_{1-6}$ alkyl, —$C_{1-6}$ alkyl-O—$C_{1-6}$ alkyl, —$C_{1-6}$ haloalkyl, —O—$C_{1-6}$ alkyl, —O—$C_{1-6}$ haloalkyl, —CN, —$NO_2$, —N($R^aR^b$), —$C_{1-6}$ alkyl-N($R^aR^b$), —C(=O)N($R^aR^b$), —$C_{1-6}$ alkyl-C(=O)N($R^aR^b$), —C(=O)$R^a$, —$C_{1-6}$ alkyl-C(=O)$R^a$, —$CO_2R^a$, —$C_{1-6}$ alkyl-$CO_2R^a$, —$OCO_2R^a$, —$C_{1-6}$ alkyl-$OCO_2R^a$, —S(O)$_nR^a$, —$C_{1-6}$ alkyl-S(O)$_nR^a$, —$SO_2N(R^aR^b)$, —$C_{1-6}$ alkyl-$SO_2N(R^aR^b)$, —N($R^a$)$SO_2R^b$, —$C_{1-6}$ alkyl-N($R^a$)$SO_2R^b$, —N($R^a$)C(=O)$R^b$, —$C_{1-6}$ alkyl-N($R^a$)C(=O)$R^b$, —N($R^a$)$CO_2R^b$, —$C_{1-6}$ alkyl-N($R^a$)$CO_2R^b$, —N($R^a$)$SO_2$N($R^aR^b$), —$C_{1-6}$ alkyl-N($R^a$)$SO_2$N($R^aR^b$), phenyl, —$C_{1-6}$ alkyl-phenyl, —O-phenyl, —$C_{1-6}$ alkyl-O-phenyl, HetA, or —$C_{1-6}$ alkyl-HetA; wherein each HetA is a 5- or 6-membered heteroaromatic ring containing from 1 to 4 heteroatoms independently selected from N, O and S, wherein the heteroaromatic ring is optionally fused with a benzene ring; and wherein each HetA is optionally substituted with one or more substituents each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$; and (c) the heteroaryl is a 5- or 6-membered heteraromatic ring containing from 1 to 4 heteroatoms or a 9- or 10-membered bicyclic heteroaromatic ring system containing from 1 to 6 heteroatoms, wherein the heteroatoms in the heteroaryl are independently selected from N, O and S; and wherein the heteroaryl is optionally substituted with one or more substituents each of which is independently halogen, —OH, —$C_{1-6}$ alkyl, —$C_{1-6}$ alkyl-O—$C_{1-6}$ alkyl, —$C_{1-6}$ haloalkyl, —O—$C_{1-6}$ alkyl, —O—$C_{1-6}$ haloalkyl, —N($R^a R^b$), —$C_{1-6}$ alkyl-N($R^a R^b$), —C(═O)N($R^a R^b$), —$C_{1-6}$ alkyl-C(═O)N($R^a R^b$), —C(═O)$R^a$, —$C_{1-6}$ alkyl-C(═O)$R^a$, —$CO_2 R^a$, —$C_{1-6}$ alkyl-$CO_2 R^a$, —$OCO_2 R^a$, —$C_{1-6}$ alkyl-$OCO_2 R^a$, —S(O)$_n R^a$, —$C_{1-6}$ alkyl-S(O)$_n R^a$, —$SO_2$N($R^a R^b$), —$C_{1-6}$ alkyl$_2 SO_2$N($R^a R^b$), —N($R^a$)$SO_2 R^b$, —$C_{1-6}$ alkyl-N($R^a$)$SO_2 R^b$, —N($R^a$)C(═O)$R^b$, —$C_{1-6}$ alkyl-N($R^a$)C(═O)$R^b$, —N($R^a$)$CO_2 R^b$, —$C_{1-6}$ alkyl-N($R^a$)$CO_2 R^b$, phenyl, —$C_{1-6}$ alkyl-phenyl, or oxo;

(4) —O—$C_{1-6}$ alkyl, optionally substituted with one or more substituents each of which is independently halogen, —OH, —O—$C_{1-6}$ alkyl, —O—$C_{1-6}$ haloalkyl, —S(O)$_n R^a$, —N($R^a$)—$CO_2 R^b$, or —C(═O)N($R^a R^b$), (5) —OH,
(6) halo,
(7) —$NO_2$,
(8) —CN,
(9) —C(═O)$R^a$,
(10) —$CO_2 R^a$,
(11) —S(O)$_n R^a$,
(12) —$SO_2$N($R^a R^b$),
(13) —N($R^a R^b$),
(14) —C(═O)N($R^a R^b$),
(15) —N($R^a$)$SO_2 R^b$,
(16) —OC(═O)N($R^a R^b$),
(17) —N($R^a$)C(═O)N($R^a R^b$),
(18) —N($R^a$)—$C_{1-6}$ alkyl-C(═O)N($R^a R^b$),
(19) —N($R^a$)—C(═O)—$C_{1-6}$ alkyl-N($R^a R^b$),
(20) —N($R^a$)C(═O)—C(═O)N($R^a R^b$),
(21) —$OCO_2 R^a$,
(22) —N($R^a$)—$SO_2$N($R^a R^b$),
(23) —N($R^a$)—$SO_2$—$C_{1-6}$ alkyl-N($R^a R^b$),
(24) —N($R^a$)C(═O)$R^b$,
(25) —N($R^a$)$CO_2 R^b$,
(26) —S—$C_{1-6}$ alkyl-C(═O)N($R^a R^b$), or
(27) —N($SO_2 R^a$)—$C_{1-6}$ alkyl-C(═O)N($R^a R^b$);

$R^3$ is
(1) —H,
(2) —$C_{1-6}$ alkyl, optionally substituted with one or more substituents each of which is independently halogen, —OH, —O—$C_{1-6}$ alkyl, —O—$C_{1-6}$ haloalkyl, —CN, —$NO_2$, —N($R^a R^b$), —C(═O)N($R^a R^b$), —OC(═O)N($R^a R^b$), —N($R^a$)C(═O)N($R^a R^b$), —N($R^a$)—$C_{1-6}$ alkyl-C(═O)N($R^a R^b$), —N($R^a$)—C(═O)—$C_{1-6}$ alkyl-N($R^a R^b$), —N($R^a$)C(═O)—C(═O)N($R^a R^b$), —C(═O)$R^a$, —$CO_2 R^a$, —$OCO_2 R^a$, —S(O)$_n R^a$, —$SO_2$N($R^a R^b$), —N($R^a$)—$SO_2$N($R^a R^b$), —N($R^a$)—$SO_2$—$C_{1-6}$ alkyl-N($R^a R^b$), —N($R^a$)C(═O)$R^b$, —N($R^a$)$CO_2 R^b$, —N($R^a$)$SO_2 R^b$, or -G-$C_{1-6}$ alkyl-C(═O)N($R^a R^b$) wherein G is O or S or N($SO_2 R^a$),
with the proviso that none of the following substituents is attached to the carbon in the —$C_{1-6}$ alkyl group that is attached to the ring nitrogen: —OH, —O—$C_{1-6}$ alkyl, —O—$C_{1-6}$ haloalkyl, —$NO_2$, —N($R^a R^b$), —OC(═O)N($R^a R^b$), —N($R^a$)C(═O)N($R^a R^b$), —N($R^a$)—$C_{1-6}$ alkyl-C(═O)N($R^a R^b$), —N($R^a$)—C(═O)—$C_{1-6}$ alkyl-N($R^a R^b$), —N($R^a$)C(═O)—C(═O)N($R^a R^b$), —$OCO_2 R^a$, —N($R^a$)—$SO_2$N($R^a R^b$), —N($R^a$)—$SO_2$—$C_{1-6}$ alkyl-N($R^a R^b$), —N($R^a$)C(═O)$R^b$, —N($R^a$)$CO_2 R^b$, —N($R^a$)$SO_2 R^b$, or -G-$C_{1-6}$ alkyl-C(═O)N($R^a R^b$) wherein G is O or N($SO_2 R^a$)), (3) —$C_{1-6}$ alkyl substituted with one of:
(i) —$R^k$,
(ii) —S(O)$_n$—$R^k$,
(iii) —S(O)$_n$—$C_{1-6}$ alkyl-$R^k$,
(iv) —C(═O)—$R^k$,
(v) —C(═O)—$C_{1-6}$ alkyl-$R^k$,
(vi) —C(═O)N($R^a$)—$R^k$, or
(vii) —C(═O)N($R^a$)—$C_{1-6}$ alkyl-$R^k$, (4) —$C_{2-6}$ alkyl substituted with one of:
(i) —O—$R^k$,
(ii) —O—$C_{1-6}$ alkyl-$R^k$,
(iii) —N($R^a$)—$R^k$,
(iv) —N($R^a$)—$C_{1-6}$ alkyl-$R^k$,
(v) —N($R^a$)C(═O)—$R^k$,
(vi) —N($R^a$)C(═O)—$C_{1-6}$ alkyl-$R^k$,
with the proviso that the substituent is not attached to the carbon in the —$C_{2-6}$ alkyl group that is attached to the ring nitrogen, (5) —S(O)$_n R^a$,
(6) —$SO_2$N($R^a R^b$),
(7) —$C_{2-6}$ alkenyl, optionally substituted with one substituent which is —C(═O)—N($R^a R^b$) or —$R^k$,
(8) —$C_{2-5}$ alkynyl, optionally substituted with one substituent which is —$CH_2$N($R^a R^b$), —$CH_2$O$R^a$, or —$R^k$,
(9) —$R^k$,
(10) —S(O)$_n$—$C_{1-6}$ alkyl-$R^k$,
(11) —N($R^a$)C(═O)—$R^k$, or
(12) —N($R^a$)C(═O)—$C_{1-6}$ alkyl-$R^k$;

each of $R^4$ and $R^5$ is independently
(1) —H,
(2) —$C_{1-6}$ alkyl, optionally substituted with one or more substituents each of which is independently halogen, —OH, —O—$C_{1-6}$ alkyl, —O—$C_{1-6}$ haloalkyl, —CN, —$NO_2$, —N($R^a R^b$), —C(═O)N($R^a R^b$), —OC(═O)N($R^a R^b$), —N($R^a$)C(═O)N($R^a R^b$), —N($R^a$)—$C_{1-6}$ alkyl-C(═O)N($R^a R^b$), —N($R^a$)—C(═O)—$C_{1-6}$ alkyl-N($R^a R^b$), —N($R^a$)C(═O)—C(═O)N($R^a R^b$), —C(═O)$R^a$, —$CO_2 R^a$, —$OCO_2 R^a$, —S(O)$_n R^a$, —$SO_2$N($R^a R^b$), —N($R^a$)—$SO_2$N($R^a R^b$), —N($R^a$)—$SO_2$—$C_{1-6}$ alkyl-N($R^a R^b$), —N($R^a$)C(═O)$R^b$, —N($R^a$)$CO_2 R^b$, —N($R^a$)$SO_2 R^b$, or -G-$C_{1-6}$ alkyl-C(═O)N($R^a R^b$) wherein G is O or S or N($SO_2 R^a$), (3) —$SO_2$N($R^a R^b$), or
(4) —$C_{1-6}$ alkyl-$R^m$;

each $R^a$ and $R^b$ is independently —H, —$C_{1-6}$ alkyl, or —$C_{3-8}$ cycloalkyl;
$R^k$ is a carbocycle or a heterocycle;
each $R^m$ is independently a carbocycle or a heterocycle;
each carbocycle is independently (i) a $C_3$ to $C_8$ monocyclic, saturated or unsaturated ring, (ii) a $C_7$ to $C_{12}$ bicyclic ring system, or (iii) a $C_{11}$ to $C_{16}$ tricyclic ring system, wherein each ring in (ii) or (iii) is independent of or fused to the other ring or rings and each ring is saturated or unsaturated; wherein the carbocycle is optionally substituted with one or more substituents each of which is independently (1) halogen,
(2) —OH,
(3) —$C_{1-6}$ alkyl, optionally substituted with one or more substituents each of which is independently —OH, —O—$C_{1-6}$ alkyl, —O—$C_{1-6}$ haloalkyl, —CN, —$NO_2$, —N($R^aR^b$), —C(=O)N($R^aR^b$), —C(=O)$R^a$, —$CO_2R^a$, —$OCO_2R^a$, —S(O)$_n R^a$, —$SO_2$N($R^aR^b$), —N($R^a$)$SO_2R^b$, —N($R^a$)C(=O)$R^b$, —N($R^a$)$CO_2R^b$, —N($R^a$)$SO_2R^b$, phenyl, —O-phenyl, or HetB,
(4) —$C_{1-6}$ haloalkyl,
(5) —O—$C_{1-6}$ alkyl,
(6) —O—$C_{1-6}$ haloalkyl,
(7) —CN,
(8) —$NO_2$,
(9) —N($R^aR^b$),
(10) —C(=O)N($R^aR^b$),
(11) —C(=O)$R^a$,
(12) —$CO_2R^a$,
(13) —$OCO_2R^a$,
(14) —S(O)$_n R^a$,
(15) —N($R^a$)$SO_2R^b$,
(16) —$SO_2$N($R^aR^b$),
(17) —N($R^a$)C(=O)$R^b$,
(18) —N($R^a$)$CO_2R^b$,
(19) phenyl,
(20) —O-phenyl, or
(21) HetB,
wherein each HetB is independently a 5- or 6-membered heteroaromatic ring containing from 1 to 4 heteroatoms independently selected from N, O and S, wherein the heteroaromatic ring is optionally fused with a benzene ring; and wherein each HetB is optionally substituted with one or more substituents each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$;

each heterocycle is independently (i) a 4- to 8-membered, saturated or unsaturated monocyclic ring, (ii) a 7- to 12-membered bicyclic ring system, or (iii) an 11 to 16-membered tricyclic ring system; wherein each ring in (ii) or (iii) is independent of or fused to the other ring or rings and each ring is saturated or unsaturated; the monocyclic ring, bicyclic ring system, or tricyclic ring system contains from 1 to 6 heteroatoms independently selected from N, O and S; and wherein any one or more of the nitrogen and sulfur heteroatoms is optionally oxidized, and any one or more of the nitrogen heteroatoms is optionally quaternized; wherein the heterocycle is optionally substituted with one or more substituents each of which is independently
(1) halogen,
(2) —OH,
(3) —$C_{1-6}$ alkyl, optionally substituted with one or more substituents each of which is independently —OH, —O—$C_{1-6}$ alkyl, —CN, —$NO_2$, —N($R^aR^b$), —C(=O)N($R^aR^b$), —C(=O)$R^a$, —$CO_2R^a$, —S(O)$_n$$^a$, —N($R^a$)$SO_2R^b$, —$SO_2$N($R^aR^b$), —N($R^a$)C(=O)$R^b$, —N($R^a$)$CO_2R^b$, phenyl, —O-phenyl, or HetC,
(4) —$C_{1-6}$ haloalkyl,
(5) —O—$C_{1-6}$ alkyl,
(6) —O—$C_{1-6}$ haloalkyl,
(7) —CN,
(8) —$NO_2$,
(9) —N($R^aR^b$),
(10) —C(=O)N($R^aR^b$),
(11) —C(=O)$R^a$,
(12) —$CO_2R^a$,
(13) —$OCO_2R^a$,
(14) —S(O)$_n R^a$,
(15) —N($R^a$)$SO_2R^b$,
(16) —$SO_2$N($R^aR^b$),
(17) —N($R^a$)C(=O)$R^b$,
(18) —N($R^a$)$CO_2R^b$,
(19) phenyl,
(20) —O-phenyl,
(21) HetC, or
(22) oxo;
wherein each HetC is independently a 5- or 6-membered heteroaromatic ring containing from 1 to 4 heteroatoms independently selected from N, O and S, wherein the heteroaromatic ring is optionally fused with a benzene ring; and wherein each HetC is optionally substituted with one or more substituents each of which is independently —$C_{1-6}$ alkyl, —$C_{1-6}$ haloalkyl, —O—$C_{1-6}$ alkyl, —O—$C_{1-6}$ haloalkyl, oxo, or —$CO_2R^a$; and each n is independently an integer equal to 0, 1 or 2;
or a pharmaceutically acceptable salt thereof.

2. The compound according to claim 1, wherein $R^{1a}$ and $R^{1c}$ are both —H; and $R^{1b}$ is fluoro;
or a pharmaceutically acceptable salt thereof.

3. The compound according to claim 1, wherein $R^{2a}$ and $R^{2b}$ are each independently:
(1) —H,
(2) —$C_{1-4}$ alkyl, optionally substituted with 1 or 2 substituents each of which is independently —OH, —O—$C_{1-4}$ alkyl, —O—$CF_3$, —CN, —$NO_2$, —N($R^aR^b$), —C(=O)N($R^aR^b$), —C(=O)$R^a$, —$CO_2R^a$, —$OCO_2R^a$, —S(O)$_n R^a$, —$SO_2$N($R^aR^b$), —N($R^a$)C(=O)$R^b$, —N($R^a$)$CO_2R^b$, or —N($R^a$)$SO_2R^b$,
(3) —$CF_3$,
(4) —$C_{1-4}$ alkyl substituted with one of —$C_{3-6}$ cycloalkyl, aryl, or heteroaryl, wherein:
the cycloalkyl is optionally substituted with 1 or 2 substituents each of which is independently fluoro, chloro, bromo, —OH, —$C_{1-4}$ alkyl, —$(CH_2)_{1-2}$—O—$C_{1-4}$ alkyl, —$CF_3$, —O—$C_{1-4}$ alkyl, —$OCF_3$, or phenyl;
the aryl is phenyl, naphthyl, anthryl, or phenanthryl; wherein the aryl is optionally substituted with from 1 to 3 substituents each of which is independently fluoro, chloro, bromo, —OH, —$C_{1-4}$ alkyl, —$(CH_2)_{1-2}$—O—$C_{1-4}$ alkyl, —$CF_3$, —O—$C_{1-4}$ alkyl, —$OCF_3$, —CN, —$NO_2$, —N($R^aR^b$), —$C_{1-4}$ alkyl-N($R^aR^b$), —C(=O)N($R^aR^b$), —$C_{1-4}$ alkyl-C(=O)N($R^aR^b$), —C(=O)$R^a$, —$C_{1-4}$ alkyl-C(=O)$R^a$, —$CO_2R^a$, —$C_{1-4}$ alkyl-$CO_2R^a$, —$OCO_2R^a$, —$C_{1-4}$ alkyl-$OCO_2R^a$, —S(O)$_n R^a$, —$C_{1-4}$ alkyl-S(O)$_n R^a$, —$SO_2$N($R^aR^b$), —$C_{1-4}$ alkyl-$SO_2$N($R^aR^b$), —N($R^a$)$SO_2R^b$, —$C_{1-4}$ alkyl-N($R^a$)$SO_2R^b$, —N($R^a$)C(=O)$R^b$, —$C_{1-4}$ alkyl-N($R^a$)C(=O)$R^b$, —N($R^a$)$CO_2R^b$, —$C_{1-4}$ alkyl-N($R^a$)$CO_2R^b$, —N($R^a$)$SO_2$N($R^aR^b$), —$C_{1-4}$ alkyl-N($R^a$)$SO_2$N($R^aR^b$), phenyl, —$C_{1-4}$ alkyl-phenyl, —O-phenyl, —$C_{1-4}$ alkyl-O-phenyl, HetA, or —$C_{1-4}$ alkyl-HetA; wherein each HetA is a 5- or 6-membered heteroaromatic ring containing from 1 to 4 heteroatoms independently selected from N, O and S, wherein the heteroaromatic ring is optionally fused with a benzene ring; and wherein each HetA is optionally substituted with from 1 to 4 substituents each of which is independently —$C_{1-4}$ alkyl, —$CF_3$, —O—$C_{1-4}$ alkyl, —$OCF_3$, oxo, or —$CO_2R^a$; and the heteroaryl is a 5- or 6-membered heteroaromatic ring containing from 1 to 4 heteroatoms independently selected from N, O and S; wherein the heteroaryl is optionally substituted with 1 or 2 substituents each of which is independently fluoro, chloro, bromo, —OH, —$C_{1-4}$ alkyl, —$(CH_2)_{1-2}$—O—$C_{1-4}$ alkyl, —$CF_3$, —O—$C_{1-4}$ alkyl, —$OCF_3$, —$N(R^aR^b)$, —$C_{1-4}$ alkyl-$N(R^aR^b)$, —$C(=O)N(R^aR^b)$, —$C_{1-4}$ alkyl-$C(=O)N(R^aR^b)$, —$C(=O)R^a$, —$C_{1-4}$ alkyl-$C(=O)R^a$, —$CO_2R^a$, —$C_{1-4}$ alkyl-$CO_2R^a$, —$OCO_2R^a$, —$C_{1-4}$ alkyl-$OCO_2R^a$, —$S(O)_nR^a$, —$SO_2N(R^aR^b)$, —$C_{1-4}$ alkyl-$S(O)_nR^a$, —$SO_2N(R^aR^b)$, —$N(R^a)SO_2R^b$, —$C_{1-4}$ alkyl-$N(R^a)SO_2R^b$, —$N(R^a)C(=O)R^b$, —$C_{1-4}$ alkyl-$N(R^a)C(=O)R^b$, —$N(R^a)CO_2R^b$, —$C_{1-4}$ alkyl-$N(R^a)CO_2R^b$, phenyl, —$C_{1-4}$ alkyl-phenyl, or oxo;

(5) —O—$C_{1-6}$ alkyl, optionally substituted with 1 or 2 substituents each of which is independently —OH, —O—$C_{1-4}$ alkyl, —$OCF_3$, —$S(O)_nR^a$, or —NH—$CO_2R^a$, or —$C(=O)N(R^aR^b)$, (6) —$OCF_3$, (7) —OH, (8) fluoro, chloro, or bromo, (9) —$NO_2$,

(10) —CN,

(11) —$C(=O)R^a$,

(12) —$CO_2R^a$,

(13) —$S(O)_nR^a$,

(14) —$SO_2N(R^aR^b)$,

(15) —$N(R^aR^b)$,

(16) —$C(=O)N(R^aR^b)$,

(17) —$N(R^a)SO_2R^b$, or

(18) —$N(R^a)C(=O)R^b$;

or a pharmaceutically acceptable salt thereof.

4. The compound according to claim 3, wherein $R^{2a}$ and $R^{2b}$ are each independently:

(1) —H, (2) —$C_{1-4}$ alkyl, (3) —$C_{1-2}$ alkyl substituted with one substituent which is —OH, $OCH_3$, —CN, —$N(R^aR^b)$, —$C(=O)N(R^aR^b)$, —$C(=O)R^a$, —$CO_2R^a$, —$SR^a$, —$SO_2R^a$, —$SO_2N(R^aR^b)$, —$N(R^a)C(=O)R^b$, —$N(R^a)CO_2R^b$, or —$N(R^a)SO_2R^b$, (4) —$CF_3$, (5) —$CH_2$-cyclopropyl, (6) —$CH_2$-phenyl, wherein the phenyl is optionally substituted with from 1 to 3 substituents each of which is independently fluoro, chloro, bromo, —$C_{1-4}$ alkyl, —$CH_2OCH_3$, —$CF_3$, —O—$C_{1-4}$ alkyl, —$OCF_3$, —CN, —$N(R^aR^b)$, —$C(=O)N(R^aR^b)$, —$C(=O)R^a$, —$CO_2R^a$, or —$S(O)_nR^a$;

(7) —$CH_2$-heteroaryl, wherein the heteroaryl is pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, or thiadiazolyl; and wherein the heteroaryl is optionally substituted with 1 or 2 substituents each of which is independently fluoro, chloro, bromo, —$C_{1-4}$ alkyl, —O—$C_{1-4}$ alkyl, or oxo, (8) —O—$C_{1-4}$ alkyl, (9) —$OCF_3$,

(10) —OH

(11) fluoro, chloro, or bromo,

(12) —$NO_2$,

(13) —CN,

(14) —$C(=O)R^a$,

(15) —$CO_2R^a$,

(16) —$S(O)_nR^a$,

(17) —$SO_2N(R^aR^b)$,

(18) —$N(R^aR^b)$,

(19) —$C(=O)N(R^aR^b)$,

(20) —$N(R^a)SO_2R^b$, or

(21) —$N(R^a)C(=O)R^b$;

each $R^a$ and $R^b$ is independently —H or —$C_{1-4}$ alkyl;

or a pharmaceutically acceptable salt thereof.

5. The compound according to claim 4, wherein $R^{2a}$ and $R^{2b}$ are each independently:

(1) —H, (2) —$C_{1-4}$ alkyl, (3) —$CF_3$, (4) fluoro, chloro, or bromo, (5) —$SO_2$—$C_{1-4}$ alkyl, (6) —S—$C_{1-4}$ alkyl, (7) —$SO_2N(-C_{1-4}$ alkyl$)_2$, (8) —$C(=O)N(-C_{1-4}$ alkyl$)_2$, (9) —$NHSO_2$—$C_{1-4}$ alkyl,

(10) —$N(-C_{1-4}$ alkyl$)SO_2$—$C_{1-4}$ alkyl,

(11) —$NHC(=O)$—$C_{1-4}$ alkyl,

(12) —$N(-C_{1-4}$ alkyl$)C(=O)$—$C_{1-4}$ alkyl, or

(13) —$C(=O)NH(-C_{1-4}$ alkyl);

or a pharmaceutically acceptable salt thereof.

6. The compound according to claim 5, wherein one of $R^{2a}$ and $R^{2b}$ is —H, and the other of $R^{2a}$ and $R^{2b}$ is as defined in claim 5;

or a pharmaceutically acceptable salt thereof.

7. The compound according to claim 6, wherein one of $R^{2a}$ and $R^{2b}$ is —H, and the other of $R^{2a}$ and $R^{2b}$ is:

(1) —H, (2) —$SO_2CH_3$, (3) —$SO_2CH_2CH_3$, (4) —S—$CH_3$, (5) —S—$CH_2CH_3$, or (6) —$C(=O)NH(CH_3)$;

or a pharmaceutically acceptable salt thereof.

8. The compound according to claim 1, wherein $R^3$ is:

(1) —H, (2) —$C_{1-4}$ alkyl, optionally substituted with one substituent which is —O—$C_{1-4}$ alkyl, —CN, —$N(R^aR^b)$, —$C(=O)N(R^aR^b)$, —$OC(=O)N(R^aR^b)$, —$N(R^a)C(=O)N(R^aR^b)$, —$N(R^a)C(=O)CH_2N(R^aR^b)$, —$N(R^a)C(=O)$—$C(=O)N(R^aR^b)$, —$C(=O)R^a$, —$CO_2R^a$, —$S(O)_nR^a$, —$SO_2N(R^aR^b)$, —$N(R^a)CO_2R^b$, —$N(R^a)$—$SO_2N(R^aR^b)$, —$N(R^a)$—$SO_2CH_2N(R^aR^b)$, or —$N(R^a)SO_2R^b$, with the proviso that none of the following substituents is attached to the carbon in the —$C_{1-4}$ alkyl group that is attached to the ring nitrogen: —O—$C_{1-4}$ alkyl, —$N(R^aR^b)$, —$OC(=O)N(R^aR^b)$, —$N(R^a)C(=O)N(R^aR^b)$, —$N(R^a)$—$C(=O)$—$CH_2N(R^aR^b)$, —$N(R^a)C(=O)$—$C(=O)N(R^aR^b)$, —$N(R^a)CO_2R^b$, —$N(R^a)$—$SO_2N(R^aR^b)$, —$N(R^a)$—$SO_2$—$CH_2N(R^aR^b)$, or —$N(R^a)SO_2R^b$, (3) —$C_{1-4}$ alkyl-$R^k$, (4) —$C_{1-4}$ alkyl-$C(=O)$—$R^k$, or (5) —$CH_{2-4}$ alkyl-$N(R^a)$—$C(=O)$—$R^k$, with the proviso that the substituent is not attached to the carbon in the —$C_{2-4}$ alkyl group that is attached to the ring nitrogen; wherein $R^k$ is:

(i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl, (ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;
or a pharmaceutically acceptable salt thereof.

9. The compound according to claim 8, wherein $R^3$ is:
(1) —H,
(2) —$C_{1-4}$ alkyl,
(3) —$(CH_2)_{2-3}$—O—$C_{1-4}$ alkyl,
(4) —$(CH_2)_{2-3}$—N(—$C_{1-4}$ alkyl)$_2$,
(5) —$(CH_2)_{1-3}$—C(=O)N(—$C_{1-4}$ alkyl)$_2$,
(6) —$(CH_2)_{2-3}$—OC(=O)N(—$C_{1-4}$ alkyl)$_2$,
(7) —$(CH_2)_{2-3}$—N(—$C_{1-4}$ alkyl)C(=O)N(—$C_{1-4}$ alkyl)$_2$,
(8) —$(CH_2)_{2-3}$—N(—$C_{1-4}$ alkyl)C(=O)—$CH_2$N(—$C_{1-4}$ alkyl)$_2$,
(9) —$(CH_2)_{2-3}$—N(—$C_{1-4}$ alkyl)C(=O)—C(=O)N(—$C_{1-4}$ alkyl)$_2$,
(10) —$(CH_2)_{1-3}$—$CO_2$—$C_{1-4}$ alkyl,
(11) —$(CH_2)_{1-3}$—S(O)$_n$—$C_{1-4}$ alkyl,
(12) —$(CH_2)_{1-3}$—$SO_2$N(—$C_{1-4}$ alkyl)$_2$,
(13) —$(CH_2)_{2-3}$—N(—$C_{1-4}$ alkyl)-$CO_2$—$C_{1-4}$ alkyl,
(14) —$(CH_2)_{2-3}$—N(—$C_{1-4}$ alkyl)-$SO_2$N(—$C_{1-4}$ alkyl)$_2$,
(15) —$(CH_2)_{2-3}$—N(—$C_{1-4}$ alkyl)-$SO_2CH_2$N(—$C_{1-4}$ alkyl)$_2$,
(16) —$(CH_2)_{2-3}$—N(—$C_{1-4}$ alkyl)-$SO_2$—$C_{1-4}$ alkyl,
(17) —$(CH_2)_{1-3}$—$R^k$,
(18) —$(CH_2)_{1-3}$—C(=O)—$R^k$, or
(19) —$(CH_2)_{2-3}$—N(—$C_{1-4}$ alkyl)-C(=O)—$R^k$;
or a pharmaceutically acceptable salt thereof.

10. The compound according to claim 1, wherein each of $R^4$ and $R^5$ is independently:
(1) —H,
(2) —$C_{1-4}$ alkyl, optionally substituted with one substituent which is —CN, —N($R^aR^b$), —C(=O)N($R^aR^b$), —C(=O)$R^a$, —$CO_2R^a$, —S(O)$_nR^a$, —$SO_2$N($R^aR^b$), or —N($R^a$)$SO_2R^b$, or
(3) —$C_{1-4}$ alkyl-$R^m$,
wherein each $R^m$ is independently:
(i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —$C_{1-4}$ alkyl, or —O—$C_{1-4}$ alkyl;
or a pharmaceutically acceptable salt thereof.

11. The compound according to claim 10, wherein $R^4$ and $R^5$ are both —H;
or a pharmaceutically acceptable salt thereof.

12. The compound according to claim 1, wherein L is $CH_2$;
or a pharmaceutically acceptable salt thereof.

13. A compound of Formula (II):

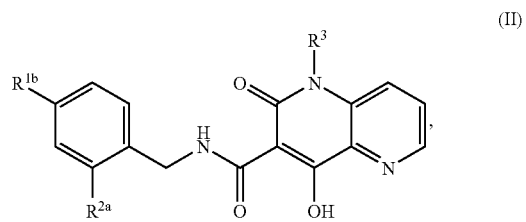

wherein:
$R^{1b}$ is —H, fluoro, chloro, bromo, —$C_{1-4}$ alkyl, or —$CF_3$;
$R^{2a}$ is:
(1) —H,
(2) —$C_{1-4}$ alkyl,
(3) —$CF_3$,
(4) fluoro, chloro, or bromo,
(5) —$SO_2$—$C_{1-4}$ alkyl,
(6) —S—$C_{1-4}$ alkyl,
(7) —$SO_2$N($R^aR^b$),
(8) —N($R^a$)$SO_2$—$C_{1-4}$ alkyl, or
(9) —C(=O)N($R^aR^b$);
$R^3$ is:
(1) —H,
(2) —$C_{1-4}$ alkyl, optionally substituted with one substituent which is —O—$C_{1-4}$ alkyl, —CN, —N($R^aR^b$), —C(=O)N($R^aR^b$), —OC(=O)N($R^aR^b$), —N($R^a$)C(=O)N($R^aR^b$), —N($R^a$)C(=O)$CH_2$N($R^aR^b$), —N($R^a$)C(=O)—C(=O)N($R^aR^b$), —C(=O)$R^a$, —$CO_2R^a$, —S(O)$_nR^a$, —$SO_2$N($R^aR^b$), —N($R^a$)$CO_2R^b$, —N($R^a$)—$SO_2$N($R^aR^b$), —N($R^a$)—$SO_2CH_2$N($R^aR^b$), or —N($R^a$)$SO_2R^b$,
with the proviso that none of the following substituents is attached to the carbon in the —$C_{1-4}$ alkyl group that is attached to the ring nitrogen: —O—$C_{1-4}$ alkyl, —N($R^aR^b$), —OC(=O)N($R^aR^b$), —N($R^a$)C(=O)N($R^aR^b$), —N($R^a$)—C(=O)—$CH_2$N($R^aR^b$), —N($R^a$)C(=O)—C(=O)N($R^aR^b$), —N($R^a$)$CO_2R^b$, —N($R^a$)—$SO_2$N($R^aR^b$), —N($R^a$)—$SO_2$—$CH_2$N($R^aR^b$), or —N($R^a$)$SO_2R^b$,
(3) —$C_{1-4}$ alkyl-$R^k$,
(4) —$C_{1-4}$ alkyl-C(=O)—$R^k$, or
(5) —$C_{2-4}$ alkyl-N($R^a$)—C(=O)—$R^k$, with the proviso that the substituent is not attached to the carbon in the —$C_{2-4}$ alkyl group that is attached to the ring nitrogen;
wherein $R^k$ is:
(i) phenyl, which is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ halo alkyl,
(ii) a 5- or 6-membered saturated heterocyclic ring containing from 1 to 4 heteratoms selected from N, O and S, wherein the saturated heterocyclic ring is optionally substituted with from 1 to 3 substituents each of which is independently —$C_{1-4}$ alkyl or oxo, or
(iii) a 5- or 6-membered heteroaromatic ring containing from 1 to 4 heteroatoms independently selected from N, O and S, wherein the heteroaromatic ring is optionally substituted with from 1 to 3 substituents each of which is independently halogen, —C$_{1-4}$ alkyl, or —O—C$_{1-4}$ alkyl;
each R$^a$ and R$^b$ is independently —H or —C$_{1-4}$ alkyl; and
n is an integer equal to zero, 1 or 2;
or a pharmaceutically acceptable salt thereof.

14. The compound according to claim 13, wherein:
R$^{1b}$ is fluoro, chloro, bromo, methyl, or ethyl;
R$^{2a}$ is:
(1) —H,
(2) methyl or ethyl,
(3) fluoro,
(4) —SO$_2$—C$_{1-4}$ alkyl,
(5) —S—C$_{1-4}$ alkyl,
(6) —SO$_2$N(—C$_{1-4}$ alkyl)$_2$,
(7) —NHSO$_2$—C$_{1-4}$ alkyl,
(8) —N(—C$_{1-4}$ alkyl)SO$_2$—C$_{1-4}$ alkyl, or
(9) —C(=O)NH(—C$_{1-4}$ alkyl);
R$^3$ is:
(1) —H,
(2) —C$_{1-4}$ alkyl,
(3) —(CH$_2$)$_{2-3}$—O—C$_{1-4}$ alkyl,
(4) —(CH$_2$)$_{2-3}$—N(—C$_{1-4}$ alkyl)$_2$,
(5) —(CH$_2$)$_{1-3}$—C(=O)N(—C$_{1-4}$ alkyl)$_2$,
(6) —(CH$_2$)$_{2-3}$—N(—C$_{1-4}$ alkyl)C(=O)N(—C$_{1-4}$ alkyl)$_2$,
(7) —(CH$_2$)$_{2-3}$—N(—C$_{1-4}$ alkyl)C(=O)—C(=O)N(—C$_{1-4}$ alkyl)$_2$,
(8) —(CH$_2$)$_{1-3}$—CO$_2$—C$_{1-4}$ alkyl,
(9) —(CH$_2$)$_{1-3}$—S(O)$_n$—C$_{1-4}$ alkyl,
(10) —(CH$_2$)$_{1-3}$—SO$_2$N(—C$_{1-4}$ alkyl)$_2$,
(11) —(CH$_2$)$_{2-3}$—N(—C$_{1-4}$ alkyl)-SO$_2$N(—C$_{1-4}$ alkyl)$_2$,
(12) —(CH$_2$)$_{2-3}$—N(—C$_{1-4}$ alkyl)-SO$_2$—C$_{1-4}$ alkyl,
(13) —(CH$_2$)$_{1-3}$—R$^k$,
(14) —(CH$_2$)$_{1-3}$—C(=O)—R$^k$, or
(15) —(CH$_2$)$_{2-3}$—N(R$^a$)—C(=O)—R$^k$;
or a pharmaceutically acceptable salt thereof.

15. The compound according to claim 14, wherein:
R$^{1b}$ is fluoro;
R$^{2a}$ is:
(1) —H,
(2) fluoro,
(3) —SO$_2$—C$_{1-4}$ alkyl,
(4) —S—C$_{1-4}$ alkyl,
(5) —SO$_2$N(—C$_{1-4}$ alkyl)$_2$,
(6) —NHSO$_2$—C$_{1-4}$ alkyl,
(7) —N(—C$_{1-4}$ alkyl)SO$_2$—C$_{1-4}$ alkyl, or
(8) —C(=O)NH(—C$_{1-4}$ alkyl);
R$^3$ is:
(1) —H,
(2) —C$_{1-4}$ alkyl,
(3) —(CH$_2$)$_{2-3}$—O—C$_{1-4}$ alkyl,
(4) —(CH$_2$)$_{2-3}$—N(—C$_{1-2}$ alkyl)$_2$,
(5) —(CH$_2$)$_{1-3}$—C(=O)N(—C$_{1-2}$ alkyl)$_2$,
(6) —(CH$_2$)$_{2-3}$—N(—C$_{1-2}$ alkyl)C(=O)N(—C$_{1-2}$ alkyl)$_2$,
(7) —(CH$_2$)$_{2-3}$—N(—C$_{1-2}$ alkyl)C(=O)—C(=O)N(—C$_{1-2}$ alkyl)$_2$,
(8) —(CH$_2$)$_{1-3}$—S(O)$_n$—C$_{1-2}$ alkyl,
(9) —(CH$_2$)$_{1-3}$—SO$_2$N(—C$_{1-2}$ alkyl)$_2$,
(10) —(CH$_2$)$_{2-3}$—N(—C$_{1-2}$ alkyl)-SO$_2$N(—C$_{1-2}$ alkyl)$_2$,
(11) —(CH$_2$)$_{2-3}$—N(—C$_{1-2}$ alkyl)-SO$_2$—C$_{1-2}$ alkyl,
(12) —(CH$_2$)$_{1-3}$—R$^k$, or
(13) —(CH$_2$)$_{1-3}$—C(=O)—R$^k$;
or a pharmaceutically acceptable salt thereof.

16. The compound according to claim 15, wherein R$^k$ is:
(i) phenyl which is optionally substituted with from 1 to 3 substituents each of which is independently fluoro, chloro, bromo, —C$_{1-4}$ alkyl, —CF$_3$, —O—C$_{1-4}$ alkyl, or —OCF$_3$;
(ii) a saturated heterocyclic ring selected from the group consisting of piperidinyl, piperazinyl, pyrrolidinyl, pyrazolidinyl, imidazolidinyl, oxazolidinyl, isoxazolidinyl, morpholinyl, thiomorpholinyl, thiazolidinyl, isothiazolidinyl, tetrahydrothienyl, tetrahydrofuryl, thiazinanyl, thiadiazinanyl, and dioxanyl; wherein the saturated heterocyclic ring is optionally substituted with from 1 to 3 substituents each of which is independently —C$_{1-4}$ alkyl or oxo; or
(iii) a heteroaromatic ring selected from the group consisting of pyridyl, pyrrolyl, pyrazinyl, pyrimidinyl, pyridazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl; wherein the heteroaromatic ring is optionally substituted with from 1 to 3 substituents each of which is independently halogen, —C$_{1-4}$ alkyl, or —O—C$_{1-4}$ alkyl;
or a pharmaceutically acceptable salt thereof.

17. A compound selected from the group consisting of:

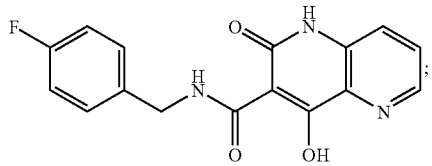

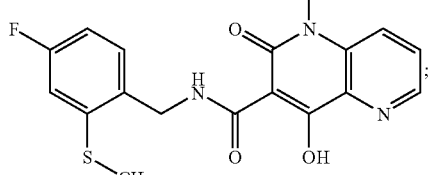

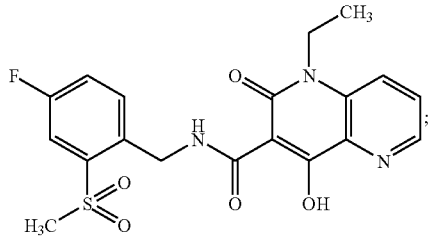

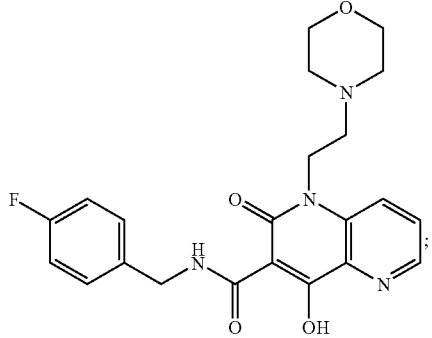

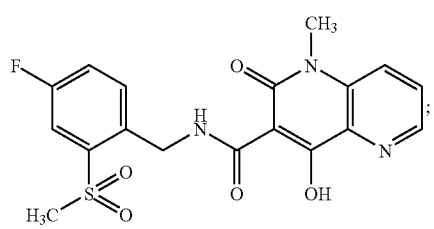
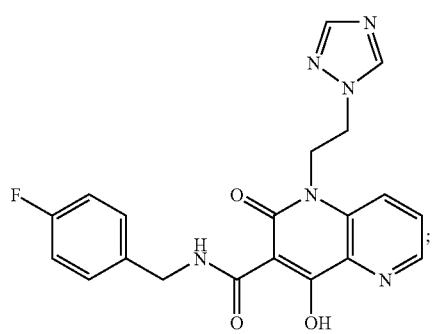
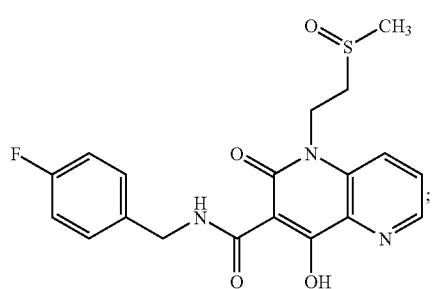
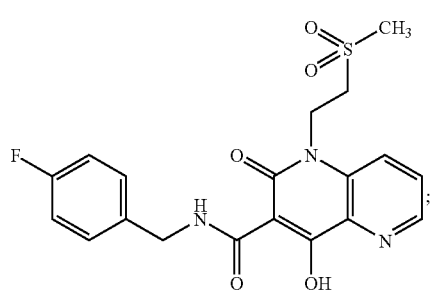
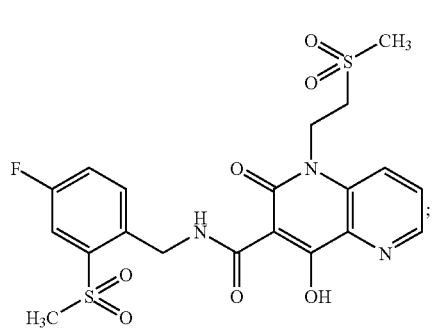
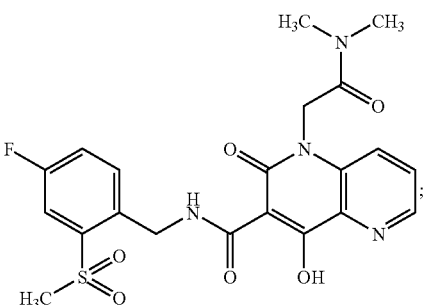
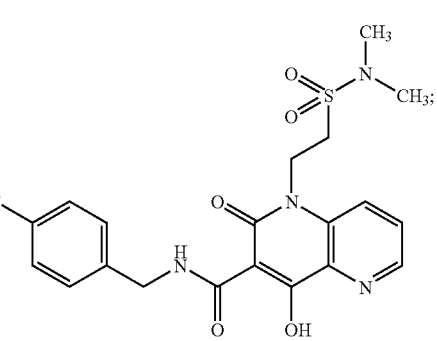
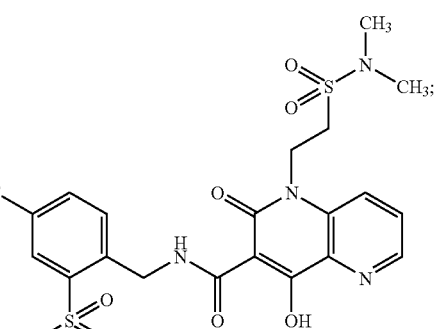
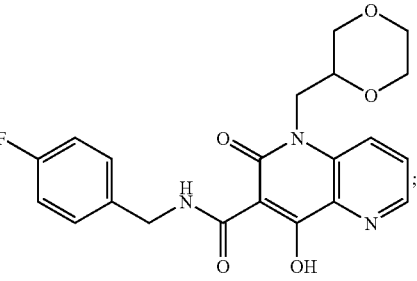
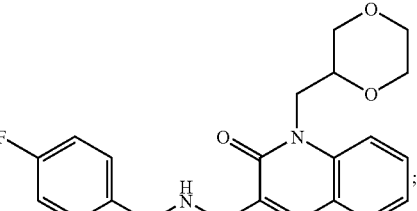
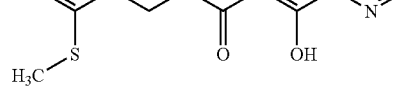

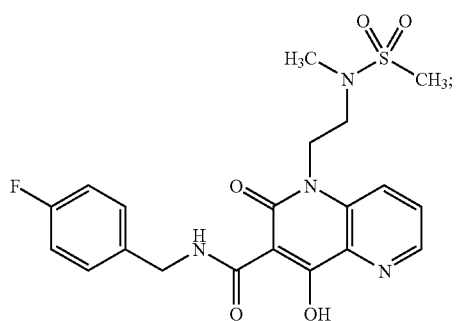
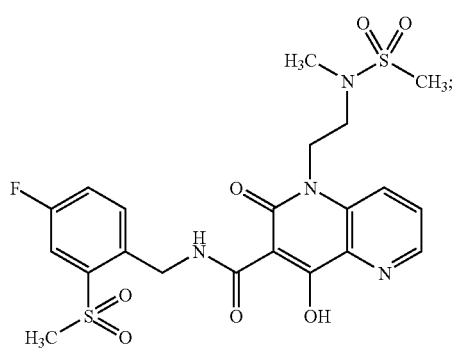
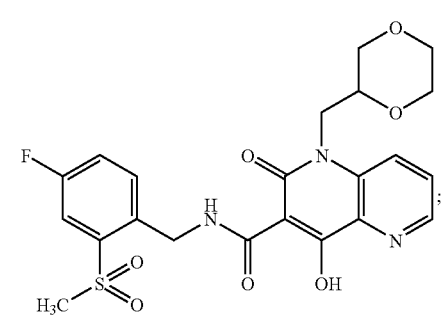
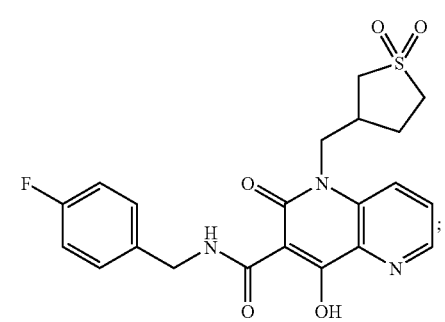
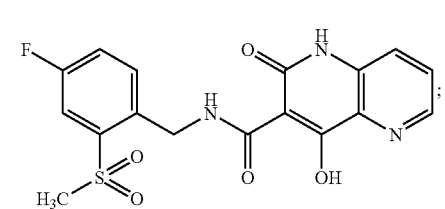
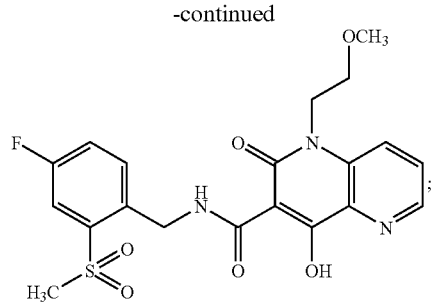
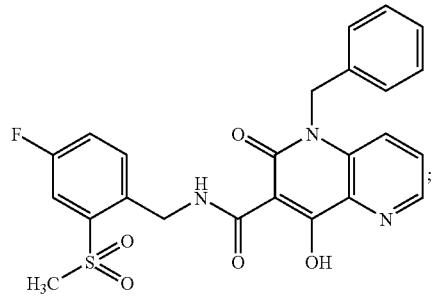
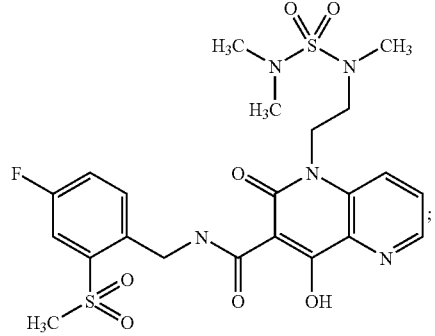
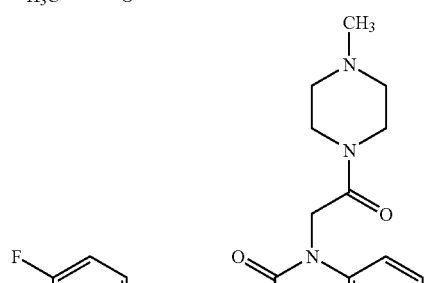
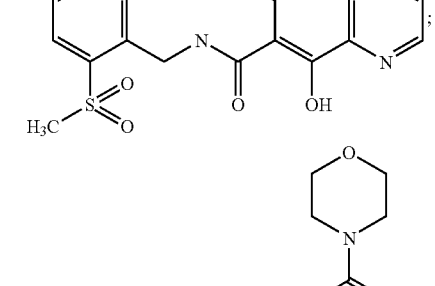
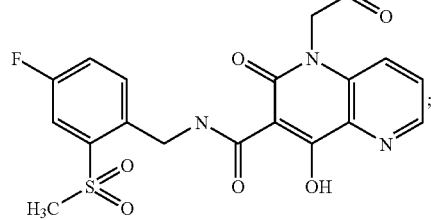

-continued

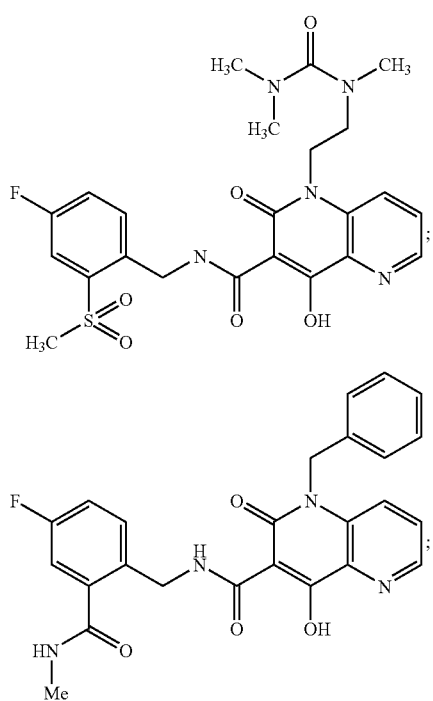

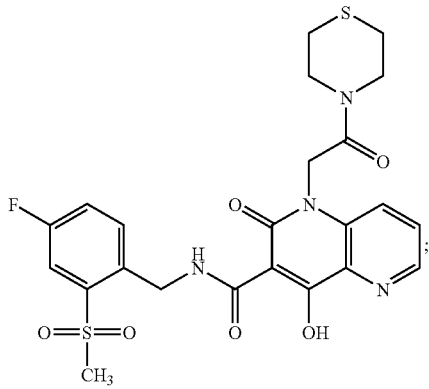

and pharmaceutically acceptable salts thereof.

18. A pharmaceutical composition comprising a therapeutically effective amount of a compound according to claim 1, or a pharmaceutically acceptable salt thereof, and a pharmaceutically acceptable carrier.

19. A method for treating infection by HIV or for treating AIDS in a subject in need thereof which comprises administering to the subject a therapeutically effective amount of the compound according to claim 1, or a pharmaceutically acceptable salt thereof.

* * * * *